United States Patent
To et al.

(10) Patent No.: US 12,290,279 B2
(45) Date of Patent: *May 6, 2025

(54) HYBRID ATHERECTOMY DEVICES

(71) Applicant: AVANTEC VASCULAR CORPORATION, Sunnyvale, CA (US)

(72) Inventors: John To, Sunnyvale, CA (US); Paul Escudero, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 448 days.

This patent is subject to a terminal disclaimer.

(21) Appl. No.: 17/833,967

(22) Filed: Jun. 7, 2022

(65) Prior Publication Data

US 2022/0387071 A1 Dec. 8, 2022

Related U.S. Application Data

(60) Provisional application No. 63/197,970, filed on Jun. 7, 2021.

(51) Int. Cl.
*A61B 17/3207* (2006.01)
*A61B 17/00* (2006.01)
*A61B 17/22* (2006.01)

(52) U.S. Cl.
CPC .......... *A61B 17/320758* (2013.01); *A61B 2017/00685* (2013.01); *A61B 2017/22094* (2013.01)

(58) Field of Classification Search
CPC .......... A61B 17/32; A61B 17/32002; A61B 17/3207; A61B 17/320758;
(Continued)

(56) References Cited

U.S. PATENT DOCUMENTS 3,358,472 A 12/1967 Klipping et al.
4,167,944 A 9/1979 Banko
(Continued)

FOREIGN PATENT DOCUMENTS

DE 20304580 U1 * 9/2004 ............ B23B 51/02
EP 0254414 8/1992
(Continued)

OTHER PUBLICATIONS

English Text DE 20304580 (Year: 2004).*
(Continued)

*Primary Examiner* — Kankindi Rwego
(74) *Attorney, Agent, or Firm* — Brian S. Boyer; SYNDICATED LAW, PC

(57) ABSTRACT

Telescoping, self-driving, and laterally-pushing atherectomy devices are provided, each having a flexible sheath, a cutter with helical flutes, and a drive assembly. The drive assembly can have a flexible driveshaft rotatably translational with the lumen of the flexible sheath, a positive displacement pump to transport cut tissue, and a flexible drive shaft that can be longer than the flexible sheath for a reversible telescoping of the drive assembly from the lumen of the flexible sheath. The positive displacement pump can be a screw pump having a drive screw portion exposed for contact with a vascular lumen for a self-driving of the device through the vascular lumen. A reversibly-expandable, lateral pushing member can be included at the distal end of the flexible sheath for a lateral pushing of the cutter. Improved cutting heads, and methods of making them, are provided for cutting a combination of soft and hard plaque.

8 Claims, 15 Drawing Sheets

(58) Field of Classification Search
CPC ........... A61B 2017/32004; A61B 2017/32008; A61B 2017/320012; A61B 2017/320032; A61B 2017/320052; A61B 17/16; A61B 17/1615; A61B 17/1622; A61B 17/1624; A61B 17/1626; A61B 17/1628; A61B 17/1637; A61B 17/1662; B23B 51/02; B23B 51/04; B23B 2251/082; Y10T 408/898; Y10T 408/895; Y10T 408/909; Y10T 408/9093; Y10T 408/9095; Y10T 408/9097
USPC ........................................................ 606/159
See application file for complete search history.

(56) References Cited

U.S. PATENT DOCUMENTS

| | | |
|---|---|---|
| 4,306,570 A | 12/1981 | Matthews |
| 4,445,509 A | 5/1984 | Auth |
| 4,598,710 A | 7/1986 | Kleinberg et al. |
| 4,598,716 A | 7/1986 | Hileman |
| 4,631,052 A | 12/1986 | Kensey |
| 4,669,469 A | 6/1987 | Gifford et al. |
| 4,690,140 A | 9/1987 | Mecca |
| 4,696,667 A | 9/1987 | Masch |
| 4,732,154 A | 3/1988 | Shiber |
| 4,770,652 A | 9/1988 | Mahurkar |
| 4,781,186 A | 11/1988 | Simpson et al. |
| 4,790,812 A | 12/1988 | Hawkins et al. |
| 4,804,364 A | 2/1989 | Dieras et al. |
| 4,808,153 A | 2/1989 | Parisi |
| 4,844,064 A | 7/1989 | Thimsen |
| 4,857,045 A | 8/1989 | Rydell |
| 4,857,046 A | 8/1989 | Stevens et al. |
| 4,867,157 A | 9/1989 | McGurk-Burleson et al. |
| 4,886,490 A | 12/1989 | Shiber |
| 4,887,599 A | 12/1989 | Muller |
| 4,894,051 A | 1/1990 | Shiber |
| 4,911,148 A | 3/1990 | Sosnowski |
| 4,950,277 A | 8/1990 | Farr |
| 4,994,067 A | 2/1991 | Summers |
| 4,994,087 A | 2/1991 | Konrad et al. |
| 5,041,082 A | 8/1991 | Shiber |
| 5,047,040 A * | 9/1991 | Simpson ............ A61B 17/3207 606/159 |
| 5,074,841 A | 12/1991 | Ademovic |
| 5,100,426 A | 3/1992 | Nixon |
| 5,114,399 A | 5/1992 | Kovalcheck |
| 5,122,134 A | 6/1992 | Borzone et al. |
| 5,231,989 A | 8/1993 | Middleman et al. |
| 5,242,461 A | 9/1993 | Kortenbach et al. |
| 5,267,955 A | 12/1993 | Hanson |
| 5,282,813 A | 2/1994 | Redha |
| 5,282,821 A | 2/1994 | Donahue |
| 5,284,128 A | 2/1994 | Hart |
| 5,304,189 A | 4/1994 | Goldberg et al. |
| 5,312,427 A | 5/1994 | Shturman |
| 5,314,438 A | 5/1994 | Shturman |
| 5,320,635 A | 6/1994 | Smith |
| 5,332,329 A | 7/1994 | Hill et al. |
| 5,334,211 A | 8/1994 | Shiber |
| 5,356,418 A | 10/1994 | Shturman |
| 5,358,472 A | 10/1994 | Vance et al. |
| 5,360,432 A | 11/1994 | Shturman |
| 5,370,609 A | 12/1994 | Drasler et al. |
| 5,372,587 A | 12/1994 | Hammerslag et al. |
| 5,409,454 A | 4/1995 | Fischell et al. |
| 5,417,703 A | 5/1995 | Brown et al. |
| 5,423,799 A | 6/1995 | Shiu |
| 5,429,604 A | 7/1995 | Hammersmark et al. |
| 5,429,617 A | 7/1995 | Hammersmark et al. |
| 5,431,173 A | 7/1995 | Chin et al. |
| 5,456,680 A | 10/1995 | Taylor et al. |
| 5,474,532 A | 12/1995 | Steppe |
| 5,489,291 A | 2/1996 | Wiley |
| 5,501,653 A | 3/1996 | Chin |
| 5,520,609 A | 5/1996 | Moll et al. |
| 5,529,580 A | 6/1996 | Kusunoki et al. |
| 5,540,706 A | 7/1996 | Aust |
| 5,554,163 A | 9/1996 | Shturman |
| 5,556,408 A | 9/1996 | Farhat |
| 5,569,197 A | 10/1996 | Helmus |
| 5,569,275 A | 10/1996 | Kotula |
| 5,584,843 A | 12/1996 | Wulfman |
| 5,618,294 A | 4/1997 | Aust |
| 5,626,562 A | 5/1997 | Castro |
| 5,632,755 A | 5/1997 | Nordgren |
| 5,634,178 A | 5/1997 | Sugiura |
| 5,634,883 A | 6/1997 | Chin |
| 5,643,178 A | 7/1997 | Moll |
| 5,643,251 A | 7/1997 | Hillsman |
| 5,643,297 A | 7/1997 | Nordgren |
| 5,643,298 A | 7/1997 | Nordgren |
| 5,649,941 A | 7/1997 | Lary |
| 5,656,562 A | 8/1997 | Wu |
| 5,665,062 A | 9/1997 | Houser |
| 5,665,098 A | 9/1997 | Kelly |
| 5,669,926 A | 9/1997 | Aust |
| 5,690,634 A | 11/1997 | Muller |
| 5,690,643 A | 11/1997 | Wijay |
| 5,695,506 A | 12/1997 | Pike |
| 5,716,327 A | 2/1998 | Warner |
| 5,725,543 A | 3/1998 | Redha |
| 5,728,129 A | 3/1998 | Summers |
| 5,733,297 A | 3/1998 | Wang |
| 5,743,456 A | 4/1998 | Jones |
| 5,746,758 A | 5/1998 | Nordgren |
| 5,749,885 A | 5/1998 | Sjostrom |
| 5,755,731 A | 5/1998 | Grinberg |
| 5,766,196 A | 6/1998 | Griffiths |
| 5,772,329 A | 6/1998 | Bardon |
| 5,779,721 A | 7/1998 | Nash |
| 5,782,834 A | 7/1998 | Lucey |
| 5,820,592 A | 10/1998 | Hammerslag |
| 5,826,582 A | 10/1998 | Sheehan |
| 5,828,582 A | 10/1998 | Conklen |
| 5,843,103 A | 12/1998 | Wulfman |
| 5,851,208 A | 12/1998 | Trott |
| 5,851,212 A | 12/1998 | Zirps |
| 5,865,082 A | 2/1999 | Cote |
| 5,865,098 A | 2/1999 | Anelli |
| 5,873,882 A | 2/1999 | Straub |
| 5,876,414 A | 3/1999 | Straub |
| 5,882,329 A | 3/1999 | Patterson |
| 5,882,333 A | 3/1999 | Schaer |
| 5,885,098 A | 3/1999 | Witkowski |
| 5,890,643 A | 4/1999 | Razon |
| 5,895,399 A | 4/1999 | Barbut |
| 5,895,508 A | 4/1999 | Halow |
| 5,897,566 A | 4/1999 | Shturman |
| 5,902,263 A | 5/1999 | Patterson |
| 5,902,283 A | 5/1999 | Darouiche |
| 5,902,313 A | 5/1999 | Redha |
| 5,910,150 A | 6/1999 | Saadat |
| 5,941,869 A | 8/1999 | Patterson |
| 5,941,893 A | 8/1999 | Saadat |
| 6,001,112 A | 12/1999 | Taylor |
| 6,015,420 A | 1/2000 | Wulfman |
| 6,027,450 A | 2/2000 | Brown |
| 6,027,514 A | 2/2000 | Stine |
| 6,042,593 A | 3/2000 | Storz |
| 6,048,339 A | 4/2000 | Zirps |
| 6,053,923 A | 4/2000 | Veca |
| 6,066,153 A | 5/2000 | Lev |
| 6,080,170 A | 6/2000 | Nash |
| 6,086,153 A | 7/2000 | Heidmann |
| 6,090,118 A | 7/2000 | McGuckin |
| 6,113,615 A | 9/2000 | Wulfman |
| 6,132,444 A | 10/2000 | Shturman |
| 6,139,557 A | 10/2000 | Passafaro |
| 6,142,955 A | 11/2000 | Farascioni |
| 6,146,395 A | 11/2000 | Kanz |
| 6,152,938 A | 11/2000 | Curry |
| 6,156,046 A | 12/2000 | Passafaro |

(56) References Cited

U.S. PATENT DOCUMENTS

| | | |
|---|---|---|
| 6,165,209 A | 12/2000 | Patterson |
| 6,183,487 B1 | 2/2001 | Barry |
| 6,206,898 B1 | 3/2001 | Honeycutt |
| 6,237,405 B1 | 5/2001 | Leslie |
| 6,238,405 B1 | 5/2001 | Findlay |
| 6,241,744 B1 | 6/2001 | Imran |
| 6,258,098 B1 | 7/2001 | Taylor |
| 6,258,109 B1 | 7/2001 | Barry |
| 6,264,630 B1 | 7/2001 | Mickley |
| 6,284,830 B1 | 9/2001 | Gottschalk |
| 6,299,622 B1 | 10/2001 | Snow |
| 6,319,242 B1 | 11/2001 | Patterson |
| 6,325,067 B1 | 12/2001 | Sterman et al. |
| 6,355,027 B1 | 3/2002 | Le |
| 6,371,928 B1 | 4/2002 | Mcfann |
| 6,406,422 B1 | 6/2002 | Landesberg |
| 6,406,442 B1 | 6/2002 | Mcfann |
| 6,451,036 B1 | 9/2002 | Heitzmann |
| 6,454,779 B1 | 9/2002 | Taylor |
| 6,482,215 B1 | 11/2002 | Shiber |
| 6,482,217 B1 | 11/2002 | Pintor |
| 6,494,890 B1 | 12/2002 | Shturman |
| 6,497,711 B1 | 12/2002 | Plaia |
| 6,610,077 B1 | 3/2003 | Hancock et al. |
| 6,554,846 B2 | 4/2003 | Hamilton |
| 6,554,848 B2 | 4/2003 | Boylan |
| 6,562,049 B1 | 5/2003 | Norlander |
| 6,565,195 B2 | 5/2003 | Blair |
| 6,565,588 B1 | 5/2003 | Clement |
| 6,572,630 B1 | 6/2003 | McGucin |
| 6,578,851 B1 | 6/2003 | Bryant |
| 6,579,298 B1 | 6/2003 | Wyzgala |
| 6,579,299 B2 | 6/2003 | McGuckin |
| 6,596,005 B1 | 7/2003 | Kanz |
| 6,602,264 B1 | 8/2003 | McGuckin |
| 6,620,148 B1 | 9/2003 | Tsugita |
| 6,623,495 B2 | 9/2003 | Findlay |
| 6,629,953 B1 | 10/2003 | Boyd |
| 6,638,233 B2 | 10/2003 | Corvi |
| 6,638,288 B1 | 10/2003 | Shturman |
| RE38,335 E | 11/2003 | Aust |
| 6,652,548 B2 | 11/2003 | Evans et al. |
| 6,656,195 B2 | 12/2003 | Peters |
| 6,658,195 B1 | 12/2003 | Senshu |
| 6,666,854 B1 | 12/2003 | Lange |
| 6,666,874 B2 | 12/2003 | Heitzmann |
| 6,682,545 B1 | 1/2004 | Kester |
| 6,702,830 B1 | 3/2004 | Demarais |
| 6,746,422 B1 | 6/2004 | Noriega |
| 6,758,851 B2 | 7/2004 | Shiber |
| 6,790,215 B2 | 9/2004 | Findlay |
| 6,800,085 B2 | 10/2004 | Selmon |
| 6,802,284 B2 | 10/2004 | Hironaka |
| 6,808,531 B2 | 10/2004 | Lafontaine |
| 6,818,001 B2 | 11/2004 | Wulfman et al. |
| 6,818,002 B2 | 11/2004 | Shiber |
| 6,830,577 B2 | 12/2004 | Nash |
| 6,843,797 B2 | 1/2005 | Nash |
| 6,860,235 B2 | 3/2005 | Anderson |
| 6,866,854 B1 | 3/2005 | Chang |
| 6,868,854 B2 | 3/2005 | Kempe |
| 6,876,414 B2 | 4/2005 | Hara |
| 6,899,704 B2 | 5/2005 | Sterman et al. |
| 6,936,056 B2 | 8/2005 | Nash |
| 6,991,409 B2 | 1/2006 | Noland et al. |
| 6,997,934 B2 | 2/2006 | Snow |
| 7,008,375 B2 | 3/2006 | Weisel |
| 7,025,751 B2 | 4/2006 | Silva |
| 7,033,357 B2 | 4/2006 | Baxter |
| 7,037,316 B2 | 5/2006 | McGuckin |
| RE39,152 E | 6/2006 | Aust |
| 7,122,017 B2 | 10/2006 | Moutafis et al. |
| 7,169,161 B2 | 1/2007 | Bonnette et al. |
| 7,172,610 B2 | 2/2007 | Heitzmann |
| 7,172,810 B2 | 2/2007 | Hashimoto |
| 7,179,269 B2 | 2/2007 | Welch et al. |
| 7,235,088 B2 | 6/2007 | Pintor |
| 7,316,697 B2 | 1/2008 | Shiber |
| 7,344,546 B2 | 3/2008 | Wulfman |
| 7,344,548 B2 | 3/2008 | Toyota |
| 7,381,198 B2 | 6/2008 | Noriega |
| 7,399,307 B2 | 7/2008 | Evans |
| 7,479,147 B2 | 1/2009 | Honeycutt |
| 7,501,114 B2 | 3/2009 | Sehgal et al. |
| 7,534,249 B2 | 5/2009 | Nash |
| 7,645,290 B2 | 1/2010 | Lucas |
| 7,655,016 B2 | 2/2010 | Demarais et al. |
| 7,666,161 B2 | 2/2010 | Nash |
| 7,670,597 B2 | 3/2010 | Sehgal et al. |
| 7,734,332 B2 | 6/2010 | Sher |
| 7,771,445 B2 | 8/2010 | Heitzmann |
| 7,875,018 B2 | 1/2011 | Tockman |
| 7,879,022 B2 | 2/2011 | Bonnette |
| 7,892,230 B2 | 2/2011 | Woloszko |
| 7,955,345 B2 | 6/2011 | Kucharczyk et al. |
| 7,981,128 B2 | 7/2011 | To |
| 8,007,500 B2 | 8/2011 | Lin |
| 8,007,506 B2 | 8/2011 | To |
| 8,015,420 B2 | 9/2011 | Cherian |
| 8,052,704 B2 | 11/2011 | Olson |
| 8,057,395 B2 | 11/2011 | Lenker et al. |
| 8,057,497 B1 | 11/2011 | Raju et al. |
| 8,070,762 B2 | 12/2011 | Escudero et al. |
| 8,070,791 B2 | 12/2011 | Ferrera et al. |
| 8,197,493 B2 | 6/2012 | Ferrera et al. |
| 8,226,679 B2 | 7/2012 | Johnson et al. |
| 8,236,016 B2 | 8/2012 | To et al. |
| 8,252,010 B1 | 8/2012 | Raju et al. |
| 8,298,244 B2 | 10/2012 | Garcia et al. |
| 8,337,516 B2 | 12/2012 | Escudero |
| 8,361,094 B2 | 1/2013 | To et al. |
| 8,469,979 B2 | 6/2013 | Olson |
| 8,475,483 B2 | 7/2013 | Schmitz et al. |
| 8,517,994 B2 | 8/2013 | Li |
| 8,535,662 B2 | 9/2013 | Chen et al. |
| 8,545,447 B2 | 10/2013 | Demarais |
| 8,568,432 B2 | 10/2013 | Straub |
| 8,572,630 B2 | 10/2013 | Woundy |
| 8,574,262 B2 | 11/2013 | Ferrera et al. |
| 8,579,926 B2 | 11/2013 | Pintor |
| 8,585,726 B2 | 11/2013 | Yoon |
| 8,613,721 B2 | 12/2013 | Wulfman et al. |
| 8,622,992 B2 | 1/2014 | Baxter et al. |
| 8,628,549 B2 | 1/2014 | To et al. |
| 8,628,790 B2 | 1/2014 | To et al. |
| 8,632,560 B2 | 1/2014 | Pal et al. |
| 8,895,891 B2 | 1/2014 | Janardhan et al. |
| 8,647,355 B2 | 2/2014 | Escudero |
| 8,803,030 B1 | 3/2014 | Janardhan et al. |
| 8,859,934 B1 | 3/2014 | Janardhan et al. |
| 8,866,049 B1 | 3/2014 | Janardhan et al. |
| 8,715,150 B2 | 5/2014 | Creighton |
| 8,721,676 B1 | 5/2014 | Janardhan et al. |
| 8,747,350 B2 | 6/2014 | Chin |
| 8,777,976 B2 | 7/2014 | Brady et al. |
| 8,783,151 B1 | 7/2014 | Janardhan et al. |
| 8,784,434 B2 | 7/2014 | Rosenbluth et al. |
| 8,795,278 B2 | 8/2014 | Schmitz et al. |
| 8,795,306 B2 | 8/2014 | Smith et al. |
| 8,845,675 B2 | 9/2014 | Johnson et al. |
| 8,845,678 B1 | 9/2014 | Janardhan et al. |
| 8,852,205 B2 | 10/2014 | Brady et al. |
| 8,852,227 B1 | 10/2014 | Janardhan et al. |
| 8,872,068 B1 | 10/2014 | Janardhan et al. |
| 8,876,414 B2 | 11/2014 | Taniguchi |
| 8,881,849 B2 | 11/2014 | Shen et al. |
| 8,888,801 B2 | 11/2014 | To et al. |
| 8,926,491 B2 | 1/2015 | Creighton |
| 8,926,680 B2 | 1/2015 | Ferrera et al. |
| 8,932,208 B2 | 1/2015 | Kendale et al. |
| 8,932,321 B1 | 1/2015 | Janardhan et al. |
| 8,951,201 B2 | 2/2015 | Mesallum |
| 8,979,793 B2 | 3/2015 | Hofmann |
| 9,005,649 B2 | 4/2015 | Ho et al. |

(56) References Cited

U.S. PATENT DOCUMENTS

| | | |
|---|---|---|
| 9,050,127 B2 | 6/2015 | Bonnette et al. |
| 9,095,371 B2 | 8/2015 | Escudero et al. |
| 9,107,590 B2 | 8/2015 | Hansmann et al. |
| 9,179,931 B2 | 11/2015 | Janardhan et al. |
| 9,179,995 B2 | 11/2015 | Janardhan et al. |
| 9,198,679 B2 | 12/2015 | To et al. |
| 9,198,687 B2 | 12/2015 | Fulkerson et al. |
| 9,204,893 B2 | 12/2015 | Rizk et al. |
| 9,220,522 B2 | 12/2015 | Fulkerson et al. |
| 9,220,530 B2 | 12/2015 | Moberg |
| 9,238,122 B2 | 1/2016 | Malhi et al. |
| 9,254,144 B2 | 2/2016 | Nguyen et al. |
| 9,498,247 B2 | 3/2016 | Patel et al. |
| 9,308,016 B2 | 4/2016 | Escudero et al. |
| 9,314,263 B2 | 4/2016 | Escudero et al. |
| 9,345,511 B2 | 5/2016 | Smith |
| 9,393,035 B2 | 7/2016 | Yu |
| 9,445,828 B2 | 9/2016 | Turjman et al. |
| 9,492,192 B2 | 11/2016 | To et al. |
| 9,492,193 B2 | 11/2016 | To et al. |
| 9,498,600 B2 | 11/2016 | Werbickas et al. |
| 9,526,863 B2 | 12/2016 | Baxter et al. |
| 9,526,865 B2 | 12/2016 | Quick et al. |
| 9,604,291 B2 | 3/2017 | Kountanya et al. |
| 9,656,008 B2 | 5/2017 | Wulfman et al. |
| 9,668,767 B2 | 6/2017 | To et al. |
| 9,675,376 B2 | 6/2017 | To et al. |
| 9,700,332 B2 | 7/2017 | Marchand et al. |
| 9,717,520 B2 | 8/2017 | Zeroni et al. |
| 9,737,318 B2 | 8/2017 | Monstadt et al. |
| 9,770,258 B2 | 9/2017 | Smith et al. |
| 9,808,277 B2 | 11/2017 | Nash et al. |
| 9,855,071 B2 | 1/2018 | Shaltis |
| 9,883,873 B2 | 2/2018 | Kulas et al. |
| 9,931,166 B2 | 4/2018 | Sauro et al. |
| 9,968,371 B2 | 5/2018 | Todd et al. |
| 9,976,356 B2 | 5/2018 | Burhan et al. |
| 9,993,325 B2 | 6/2018 | Ren et al. |
| 10,004,531 B2 | 6/2018 | Rosenbluth |
| 10,016,211 B2 | 7/2018 | Ferrera et al. |
| 10,022,145 B2 | 7/2018 | Simpson et al. |
| 10,028,759 B2 | 7/2018 | Wallace et al. |
| 10,028,767 B2 | 7/2018 | Germain et al. |
| 10,045,790 B2 | 8/2018 | Cox et al. |
| 10,098,651 B2 | 10/2018 | Marchand et al. |
| 10,154,853 B2 | 12/2018 | To et al. |
| 10,154,854 B2 | 12/2018 | To et al. |
| 10,172,638 B2 | 1/2019 | Palme et al. |
| 10,226,275 B2 | 3/2019 | Escudero et al. |
| 10,226,277 B2 | 3/2019 | Smith et al. |
| 10,238,406 B2 | 3/2019 | Cox et al. |
| 10,456,236 B2 | 3/2019 | Nguyen et al. |
| 10,251,667 B2 | 4/2019 | Cohen et al. |
| 10,258,358 B2 | 4/2019 | Ulm, III |
| 10,258,409 B2 | 4/2019 | Ben-Oren et al. |
| 10,420,572 B2 | 4/2019 | Ulm, III |
| 10,278,719 B2 | 5/2019 | Ulm, III |
| 10,292,677 B2 | 5/2019 | Johnson et al. |
| 10,292,722 B2 | 5/2019 | Brady et al. |
| 10,292,803 B2 | 5/2019 | Monstadt et al. |
| 10,299,811 B2 | 5/2019 | Brady et al. |
| 10,307,175 B2 | 6/2019 | McGuckin et al. |
| 10,321,925 B2 | 6/2019 | Ulm, III |
| 10,335,260 B2 | 7/2019 | Janardhan et al. |
| 10,342,655 B2 | 7/2019 | Janardhan et al. |
| 10,349,974 B2 | 7/2019 | Patel et al. |
| 10,357,275 B2 | 7/2019 | Majercak et al. |
| 10,376,275 B2 | 8/2019 | Nguyen et al. |
| 10,376,678 B2 | 8/2019 | Levine |
| 10,383,751 B2 | 8/2019 | Ferrera et al. |
| 10,413,310 B2 | 9/2019 | Ferrera et al. |
| 10,426,512 B2 | 10/2019 | Avneri et al. |
| 10,441,311 B2 | 10/2019 | Smith et al. |
| 10,449,269 B2 | 10/2019 | Fahmy et al. |
| 10,463,389 B2 | 11/2019 | McGuckin et al. |
| 10,470,797 B1 | 11/2019 | Rai et al. |
| 10,492,822 B2 | 12/2019 | Chen et al. |
| 10,507,036 B2 | 12/2019 | Schuman et al. |
| 10,512,479 B2 | 12/2019 | Nguyen et al. |
| 10,524,824 B2 | 1/2020 | Rottenberg et al. |
| 10,531,883 B1 | 1/2020 | Deville et al. |
| 10,555,752 B2 | 2/2020 | Robertson et al. |
| 10,555,753 B2 | 2/2020 | Moberg et al. |
| 10,568,655 B2 | 2/2020 | Simpson et al. |
| 10,569,049 B2 | 2/2020 | Garrison et al. |
| 10,588,649 B2 | 3/2020 | Brady et al. |
| 10,588,656 B2 | 3/2020 | Trosper et al. |
| 10,595,818 B2 | 3/2020 | Levine |
| 10,603,467 B2 | 3/2020 | Alvarez et al. |
| 10,624,659 B2 | 4/2020 | Gamba et al. |
| 10,646,247 B2 | 5/2020 | Wilson et al. |
| 10,667,833 B2 | 6/2020 | Vale et al. |
| 10,682,152 B2 | 6/2020 | Vale et al. |
| 10,702,367 B2 | 7/2020 | Sachar et al. |
| 10,722,253 B2 | 7/2020 | Deville et al. |
| 10,743,894 B2 | 8/2020 | Brady et al. |
| 10,743,895 B2 | 8/2020 | Losordo et al. |
| 10,751,159 B2 | 8/2020 | Janardhan et al. |
| 10,765,446 B2 | 9/2020 | Higgins et al. |
| 10,774,596 B2 | 9/2020 | Zhang et al. |
| 10,779,843 B2 | 9/2020 | Wallace et al. |
| 10,799,331 B2 | 10/2020 | Hauser et al. |
| 10,835,268 B2 | 11/2020 | Wallace et al. |
| 10,835,271 B2 | 11/2020 | Ma |
| 10,842,498 B2 | 11/2020 | Vale et al. |
| 10,842,513 B2 | 11/2020 | Greenhalgh et al. |
| 10,856,894 B2 | 12/2020 | Wallace et al. |
| 10,863,999 B2 | 12/2020 | Wallace et al. |
| 10,888,342 B2 | 1/2021 | Wallace et al. |
| 10,888,343 B2 | 1/2021 | Wallace et al. |
| 10,932,799 B2 | 3/2021 | Sirivong |
| 10,939,934 B2 | 3/2021 | Lockard et al. |
| 10,952,760 B2 | 3/2021 | Brady et al. |
| 10,960,178 B2 | 3/2021 | Savastano et al. |
| 11,197,684 B1 | 3/2021 | Ngo et al. |
| 11,000,682 B2 | 5/2021 | Merritt et al. |
| 11,026,709 B2 | 6/2021 | Greenhalgh et al. |
| 11,058,451 B2 | 7/2021 | Marchand et al. |
| 11,065,018 B2 | 7/2021 | Buck et al. |
| 11,071,733 B1 | 7/2021 | Zaidi et al. |
| 11,076,808 B2 | 8/2021 | Levine |
| 11,077,188 B2 | 8/2021 | Kauvar et al. |
| 11,103,265 B2 | 8/2021 | Wallace et al. |
| 11,154,314 B2 | 10/2021 | Quick |
| 11,160,572 B2 | 11/2021 | Ulm, III |
| 11,191,558 B2 | 12/2021 | Nguyen et al. |
| 11,197,771 B2 | 12/2021 | Ferrera et al. |
| 11,207,096 B2 | 12/2021 | To et al. |
| 11,224,449 B2 | 1/2022 | Chou et al. |
| 11,229,445 B2 | 1/2022 | Ogle |
| 11,246,965 B2 | 2/2022 | Chen et al. |
| 11,253,291 B2 | 2/2022 | Wallace et al. |
| 11,259,824 B2 | 3/2022 | Brady et al. |
| 11,259,835 B2 | 3/2022 | Smith et al. |
| 11,291,463 B2 | 4/2022 | Atchaneeyasakul et al. |
| 11,304,723 B1 | 4/2022 | To et al. |
| 11,317,940 B2 | 5/2022 | Smith et al. |
| 11,337,714 B2 | 5/2022 | Ferrera et al. |
| 11,369,405 B2 | 6/2022 | Vardi et al. |
| 11,376,028 B1 | 7/2022 | Saadat et al. |
| 11,382,652 B2 | 7/2022 | Wasdyke et al. |
| 11,383,068 B2 | 7/2022 | Tran et al. |
| 11,395,675 B2 | 7/2022 | Echarri et al. |
| 11,399,711 B2 | 8/2022 | Cooper et al. |
| 11,406,403 B2 | 8/2022 | Casey et al. |
| 11,406,404 B2 | 8/2022 | Griffin |
| 11,433,218 B2 | 9/2022 | Quick et al. |
| 11,446,045 B2 | 9/2022 | Vale et al. |
| 11,458,286 B2 | 10/2022 | Bajema et al. |
| 11,471,183 B1 | 10/2022 | Deaton et al. |
| 11,478,262 B2 | 10/2022 | Ngo et al. |
| 11,497,512 B2 | 11/2022 | Wallace et al. |
| 11,497,514 B2 | 11/2022 | Greenhalgh et al. |
| 11,497,521 B2 | 11/2022 | Mallaby |

(56) References Cited

U.S. PATENT DOCUMENTS

| | | |
|---|---|---|
| 11,529,157 B2 | 12/2022 | Brady et al. |
| 11,529,158 B2 | 12/2022 | Hauser |
| 11,529,331 B2 | 12/2022 | Zeligs et al. |
| 11,534,593 B2 | 12/2022 | Franano et al. |
| 11,547,415 B2 | 1/2023 | Chou et al. |
| 11,553,935 B2 | 1/2023 | Buck et al. |
| 11,553,942 B2 | 1/2023 | Bonnette et al. |
| 11,559,382 B2 | 1/2023 | Merritt et al. |
| 11,576,724 B2 | 2/2023 | Ben-Oren et al. |
| 11,596,438 B2 | 3/2023 | Walzman |
| 11,596,769 B2 | 3/2023 | Walzman |
| 11,617,592 B2 | 4/2023 | Nayak et al. |
| 11,627,973 B2 | 4/2023 | Wallace et al. |
| 11,628,282 B2 | 4/2023 | Casey |
| 11,633,201 B2 | 4/2023 | Girdhar et al. |
| 11,642,145 B2 | 5/2023 | Vale et al. |
| 11,666,350 B2 | 6/2023 | Nguyen et al. |
| 11,712,256 B2 | 8/2023 | Vale et al. |
| 11,730,924 B2 | 8/2023 | Saadat et al. |
| 11,730,925 B2 | 8/2023 | Saadat et al. |
| 11,737,770 B2 | 8/2023 | Fitz et al. |
| 11,737,771 B2 | 8/2023 | Whelan |
| 11,751,893 B2 | 9/2023 | Bowman et al. |
| 11,751,900 B2 | 9/2023 | Vetter et al. |
| 11,771,450 B2 | 10/2023 | Wallace et al. |
| 11,771,875 B2 | 10/2023 | Malek et al. |
| 11,779,364 B2 | 10/2023 | Casey et al. |
| 11,779,406 B2 | 10/2023 | Sganga et al. |
| 11,786,269 B2 | 10/2023 | Escudero et al. |
| 11,786,699 B2 | 10/2023 | Ogle et al. |
| 11,793,400 B2 | 10/2023 | Patel |
| 11,793,531 B2 | 10/2023 | Nguyen et al. |
| 11,793,542 B2 | 10/2023 | Pons |
| 11,801,114 B2 | 10/2023 | Lang |
| 11,812,980 B2 | 11/2023 | Wallace et al. |
| 11,819,228 B2 | 11/2023 | Buck et al. |
| 11,864,779 B2 | 1/2024 | Dinh |
| 12,089,867 B2 * | 9/2024 | To ............ A61B 17/320725 |
| 2001/0005909 A | 1/2001 | Findlay |
| 2001/0004700 A1 | 6/2001 | Honeycutt |
| 2002/0004680 A1 | 1/2002 | Plaia |
| 2002/0007190 A1 | 1/2002 | Wulfman |
| 2002/0198550 A1 | 1/2002 | Nash |
| 2002/0029057 A1 | 3/2002 | McGuckin |
| 2002/0169487 A1 | 3/2002 | Graindorge |
| 2002/0077642 A1 | 6/2002 | Patel |
| 2002/0077842 A1 | 6/2002 | Charisius |
| 2002/0168467 A1 | 7/2002 | Puech |
| 2002/0107479 A1 | 8/2002 | Bates |
| 2002/0151918 A1 | 10/2002 | Lafontaine |
| 2002/0169467 A1 | 11/2002 | Heitzmann |
| 2003/0018346 A1 | 1/2003 | Follmer |
| 2003/0100911 A1 | 1/2003 | Nash |
| 2003/0114869 A1 | 1/2003 | Nash |
| 2003/0078606 A1 | 4/2003 | Lafontaine |
| 2003/0125758 A1 | 7/2003 | Simpson |
| 2003/0139751 A1 | 7/2003 | Evans |
| 2003/0139802 A1 | 7/2003 | Wulfman |
| 2004/0006358 A1 | 1/2004 | Wulfman |
| 2004/0181249 A1 | 1/2004 | Torrance |
| 2004/0199051 A1 | 3/2004 | Weisel |
| 2004/0220519 A1 | 3/2004 | Wulfman |
| 2004/0230212 A1 | 3/2004 | Wulfman |
| 2004/0230213 A1 | 3/2004 | Wulfman |
| 2004/0235611 A1 | 3/2004 | Nistal |
| 2004/0236312 A1 | 3/2004 | Nistal |
| 2004/0238312 A1 | 3/2004 | Sudau |
| 2004/0243162 A1 | 3/2004 | Wulfman |
| 2004/0202772 A1 | 4/2004 | Matsuda |
| 2004/0087988 A1 | 5/2004 | Heitzmann |
| 2004/0097995 A1 | 5/2004 | Nash |
| 2004/0102772 A1 | 5/2004 | Baxter |
| 2004/0103516 A1 | 6/2004 | Bolduc |
| 2004/0147934 A1 | 7/2004 | Kiester |
| 2004/0167533 A1 | 8/2004 | Wilson |
| 2004/0167553 A1 | 8/2004 | Simpson |
| 2004/0167554 A1 | 8/2004 | Simpson |
| 2005/0004585 A1 | 1/2005 | Hall |
| 2005/0020327 A1 | 1/2005 | Chung |
| 2005/0020974 A1 | 1/2005 | Noriega |
| 2005/0059990 A1 | 3/2005 | Ayala |
| 2005/0149084 A1 | 3/2005 | Kanz |
| 2005/0222519 A1 | 4/2005 | Simpson |
| 2005/0113853 A1 | 5/2005 | Noriega |
| 2005/0177068 A1 | 8/2005 | Simpson |
| 2005/0197661 A1 | 9/2005 | Carrison et al. |
| 2005/0197861 A1 | 9/2005 | Omori |
| 2005/0240146 A1 | 10/2005 | Nash |
| 2006/0020327 A1 | 1/2006 | Lashinski |
| 2006/0239982 A1 | 1/2006 | Simpson |
| 2006/0074442 A1 | 4/2006 | Noriega |
| 2006/0241564 A1 | 4/2006 | Corcoran |
| 2006/0229646 A1 | 10/2006 | Sparks |
| 2007/0282303 A1 | 5/2007 | Nash |
| 2007/0282358 A1 | 5/2007 | Remiszewski |
| 2007/0135733 A1 | 6/2007 | Soukup |
| 2007/0282350 A1 | 6/2007 | Hernest |
| 2007/0225739 A1 | 9/2007 | Pintor |
| 2007/0250000 A1 | 10/2007 | Magnin |
| 2008/0004643 A1 | 1/2008 | To |
| 2008/0004644 A1 | 1/2008 | To |
| 2008/0004645 A1 | 1/2008 | To |
| 2008/0004646 A1 | 1/2008 | To |
| 2008/0004647 A1 | 1/2008 | To |
| 2008/0045986 A1 | 2/2008 | To |
| 2008/0234715 A1 | 3/2008 | Pesce |
| 2008/0249364 A1 | 4/2008 | Korner |
| 2008/0103516 A1 | 5/2008 | Wulfman |
| 2008/0140101 A1 | 6/2008 | Carley |
| 2009/0018565 A1 | 1/2009 | To et al. |
| 2009/0018566 A1 | 1/2009 | Escudero |
| 2009/0018567 A1 | 1/2009 | Escudero |
| 2009/0024085 A1 | 1/2009 | To |
| 2009/0043330 A1 | 2/2009 | To |
| 2009/0043380 A1 | 2/2009 | Blaha et al. |
| 2009/0234378 A1 | 9/2009 | Escudero |
| 2010/0010492 A1 | 1/2010 | Lockard |
| 2010/0049225 A1 | 2/2010 | To |
| 2010/0174302 A1 | 3/2010 | Heitzmann |
| 2010/0119578 A1 | 5/2010 | To et al. |
| 2010/0324567 A1 | 6/2010 | Root |
| 2010/0324576 A1 | 8/2010 | Pintor |
| 2011/0040315 A1 | 2/2011 | To |
| 2011/0152906 A1 | 2/2011 | Escudero |
| 2011/0152907 A1 | 2/2011 | Escudero |
| 2011/0112563 A1 | 5/2011 | To |
| 2011/0270289 A1 | 7/2011 | To |
| 2011/0301626 A1 | 8/2011 | To |
| 2012/0083810 A1 | 4/2012 | Escudero |
| 2013/0158578 A1 | 3/2013 | Ghodke |
| 2013/0085515 A1 | 4/2013 | To |
| 2013/0090674 A1 | 4/2013 | Escudero |
| 2013/0096587 A1 | 4/2013 | Smith |
| 2013/0103062 A1 | 4/2013 | To |
| 2013/0103063 A1 | 4/2013 | Escudero |
| 2013/0296901 A1 | 11/2013 | Olson |
| 2014/0039532 A1 | 2/2014 | Vrba |
| 2014/0058423 A1 | 2/2014 | Smith |
| 2014/0107680 A1 | 4/2014 | Escudero |
| 2015/0224585 A1 | 1/2015 | Kuroda |
| 2015/0150587 A1 * | 6/2015 | Smith ............ A61B 17/320758 606/159 |
| 2017/0273698 A1 | 2/2017 | McGuckin et al. |
| 2018/0193056 A1 | 7/2018 | Colyer et al. |
| 2020/0029801 A1 | 1/2020 | Tachibana et al. |
| 2020/0029998 A1 | 1/2020 | Ogle et al. |
| 2020/0060718 A1 | 2/2020 | Patel et al. |
| 2020/0129202 A1 | 4/2020 | Schoenle et al. |
| 2020/0315654 A1 | 10/2020 | Patel et al. |
| 2020/0352552 A1 | 11/2020 | Rousso et al. |
| 2021/0186541 A1 | 6/2021 | Thress |
| 2021/0378694 A1 | 12/2021 | Thress et al. |
| 2022/0039815 A1 | 2/2022 | Thress et al. |
| 2022/0192698 A1 | 3/2022 | To et al. |

(56) References Cited

U.S. PATENT DOCUMENTS

| | | |
|---|---|---|
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2023/0218310 A1 | 7/2023 | Scheinblum et al. |
| 2023/0241302 A1 | 8/2023 | Merritt et al. |
| 2023/0248380 A1 | 8/2023 | Long et al. |
| 2023/0310751 A1 | 10/2023 | Merritt et al. |
| 2023/0355938 A1 | 11/2023 | Merritt et al. |
| 2023/0389932 A1 | 12/2023 | Ozenne et al. |
| 2024/0081857 A1 | 3/2024 | Luong et al. |
| 2024/0082540 A1 | 3/2024 | Brodt et al. |
| 2024/0157041 A1 | 5/2024 | Zikry et al. |

FOREIGN PATENT DOCUMENTS

| | | |
|---|---|---|
| EP | 0817594 | 3/1996 |
| EP | 0817595 | 3/1996 |
| EP | 0950456 A1 | 10/1999 |
| EP | 1158910 | 1/2000 |
| EP | 1176915 | 2/2002 |
| EP | 1178315 | 2/2002 |
| EP | 1315460 | 6/2003 |
| EP | 1603486 B1 | 6/2006 |
| EP | 1722694 | 11/2006 |
| EP | 1870044 | 12/2007 |
| EP | 1617893 A4 | 8/2008 |
| EP | 2579791 B1 | 6/2010 |
| EP | 2462881 | 6/2012 |
| EP | 2617372 B1 | 7/2013 |
| EP | 2641551 | 9/2013 |
| EP | 2424608 B1 | 3/2014 |
| EP | 2211732 B1 | 5/2018 |
| EP | 2164409 B1 | 8/2018 |
| EP | 3027126 B1 | 10/2019 |
| EP | 2931151 B1 | 11/2019 |
| JP | H0380872 | 4/1991 |
| JP | 2006511256 | 4/2006 |
| JP | 2011136180 A | 7/2011 |
| JP | 2013531542 A | 8/2013 |
| JP | 6266108 B2 | 1/2018 |
| JP | 6356604 B2 | 7/2018 |
| WO | WO 1992/001423 | 2/1992 |
| WO | WO 1992/014506 | 9/1992 |
| WO | WO 1994/024946 | 11/1994 |
| WO | WO 1995/021576 | 8/1995 |
| WO | WO 1996/029941 | 10/1996 |
| WO | WO 1996/029942 | 10/1996 |
| WO | WO 1999/023958 | 5/1999 |
| WO | WO 1999/035977 | 7/1999 |
| WO | WO 2000/054659 | 9/2000 |
| WO | WO 2000/054859 | 9/2000 |
| WO | WO 2001/064115 | 9/2001 |
| WO | WO 2001/074255 | 10/2001 |
| WO | WO 2001/076680 | 10/2001 |
| WO | WO 2005/084562 | 9/2005 |
| WO | WO 2005/123169 | 12/2005 |
| WO | WO 2006/028886 | 3/2006 |
| WO | WO 2007/010389 | 1/2007 |
| WO | WO 2008/005888 | 1/2008 |
| WO | WO 2008/005891 | 1/2008 |
| WO | WO 2009/005779 | 1/2009 |
| WO | WO 2009/054968 | 4/2009 |
| WO | WO 2009/126309 | 10/2009 |
| WO | WO 2009/144580 | 12/2009 |
| WO | WO 2010/050391 | 5/2010 |
| WO | WO 2010/054121 | 5/2010 |
| WO | WO 2011/044533 | 4/2011 |
| WO | WO 2013/056262 | 4/2013 |
| WO | WO 2013/172970 | 11/2013 |
| WO | WO 2015/017114 | 2/2015 |
| WO | WO 2016/001932 | 1/2016 |
| WO | WO 2020/234203 | 11/2020 |
| WO | PCT/US22/32428 | 6/2022 |
| WO | PCT/US2024/042773 | 8/2024 |

OTHER PUBLICATIONS

U.S. Appl. No. 63/126,847 (priority for U.S. Appl. No. 17/518,294, cited herein) To, et al.—owned by Applicant, filed Dec. 17, 2020.
U.S. Appl. No. 63/197,970 (priority for U.S. Appl. No. 17/518,294, cited herein) To, et al.—owned by Applicant, filed Jun. 7, 2021.
Written opinion and search report for PCT/US22/32428, To—owned by Applicant, Jun. 7, 2022.
Ikeno et al. Initial Experience with the Novel 6 F r-Compatible System for Debulking De Novo Coronary Arterial Lesions. Catheterization and Cardiovascular Interventions 62:308-17. (2004).
Kanjwal et al. Peripheral Arterial Disease—A Silent Killer. JK-Practitioner 11(4):225-32 (2004).
Nakamura et al. Efficacy and Feasibility of Helixcision for Debulking Neointimal Hyperplasia for In-Stent Restenosis. Catheterization and Cardiovascular Interventions 57:460-66 (2002).
U.S. Appl. No. 18/805,071, To, et al.—owned by Applicant, filed Mar. 11, 2022.
U.S. Appl. No. 18/807,575, To, et al.—owned by Applicant, filed Aug. 16, 2023.
U.S. Appl. No. 63/520,029, To, et al.—owned by Applicant, filed Aug. 16, 2023.
Extended European Search Report for EP 22820858, Mar. 27, 2024, To—owned by Applicant.
Caranfa, J.T., et al. Mechanical endovascular therapy for acute ischemic stroke: An indirect treatment comparison between Solitaire and Penumbra thrombectomy devices. PLoS ONE 13(3): e0191657 (2018) https://doi.org/10.1371/journal.pone.0191657.
U.S. Appl. No. 19/000,952, To, et al.—owned by Applicant, filed Aug. 16, 2023.
Written opinion and search report for PCT/US2024/042773, To, et al.—owned by Applicant, Aug. 16, 2024.

\* cited by examiner

PRIOR ART

HYBRID ATHERECTOMY DEVICES

CROSS REFERENCES TO RELATED APPLICATIONS

This application claims priority to U.S. Provisional Application No. 63/197,970, filed Jun. 7, 2021, which is hereby incorporated herein by reference in its entirety.

BACKGROUND

Field of the Invention

The teachings herein are directed generally to medical devices and methods, including devices and methods for performing atherectomies through both soft and hard vascular plaque.

Description of the Related Art

An atherectomy is a minimally invasive procedure for removing atherosclerosis from blood vessels within the body and is an alternative to angioplasty in the treatment of narrowing arteries. Common applications include peripheral arterial disease and coronary artery disease. Unlike angioplasty and stents, which push plaque into the vessel wall, the atherectomy procedure cuts plaque away from the wall of a blood vessel. While atherectomies are usually used to remove plaque from arteries, they can also be used in veins and vascular bypass grafts, for example.

Atherectomies can offer improvements over balloon dilatation and stent placement, which are considered traditional interventional surgical methods of treating atherosclerosis. In balloon dilatation, a collapsed balloon is inserted into a blood vessel and inflated to push plaque against the vessel wall, and the stent can be placed to hold the plaque as a scaffolding in order to try and maintain the integrity of the lumen of the vessel. However, such traditional treatments can stretch the artery and induce scar tissue formation, while the placement of a stent may also cut arterial tissue and induce scar tissue formation. The scar tissue formation can lead to restenosis of the artery. Moreover, the dilatation with the balloon can also rip the vessel wall. Because atherectomies enlarge the lumen by removing plaque rather than stretching the vessel, risk of suffering vessel injuries, such as dissections that can lead to increased restenosis, is reduced.

Unfortunately, the art suffers performance limitations in state-of-the-art atherectomy devices. For example, current devices with rotating cutters cannot handle the variety of soft, fibrous and calcific plaque effectively, either not cutting all types of plaque or breaking up the plaque into large pieces that remain in the arterial bed as emboli that can clog blood vessels downstream. As plaque is a tissue made of fat, cholesterol, calcium, fibrous connective tissue and other substances found in the body, it can be highly variable and classified mainly into four different types of tissue: calcified and hard, necrotic and soft, fibrotic, and a combination thereof. Calcified plaque can be hard as a bone; fatty plaque is typically soft; and fibrotic plaque is typically viscoelastic, stretchy yet firm, and thus difficult to cut. Some state-of-the-art devices have burrs that can grind-away hard plaque but can't cut soft or viscoelastic plaque. Worse yet, they can loosen debris that can become dangerous emboli. Some state-of-the-art devices have a sharp cutter that can be deflected against one side of the vessel to do eccentric cutting, which is desirable, but the amount of deflection can't be effectively controlled. And, some state-of-the-art devices have a "nose cone" that prevents the cutter from cutting through lesion that doesn't allow enough progression of the device to reach the cutter blades.

Most importantly, however, is that patients having "tight" or "tough" lesions are currently unable to receive treatments with balloons, stents, or atherectomy devices. Such lesions are occlusions that leave only a very small luminal opening, or no opening, making it difficult-to-impossible to achieve passage of a guidewire, much less passage of a balloon or stent on the guidewire. For example, a luminal opening that is only 0.5 mm may allow passage of a guidewire, perhaps, but the smallest stents may be 1.0 mm, and the smallest balloon may be 0.75 mm, neither of which can pass through a tough, small lesion for the treatment. And, as noted above, current atherectomy devices have a difficult time cutting away the plaque, even if the guidewire might be able to pass through the luminal opening. In situations having a total occlusion, the problem is exacerbated.

As such, one of skill will appreciate an atherectomy device that (i) can effectively cut and remove the 4 different types of plaque tissue, namely calcified and hard, necrotic and soft, fibrotic, and a combination thereof; (ii) can render a concentric vessel lumen with minimal plaque burden; (iii) can safely self-collect and remove plaque particles to avoid release of emboli; and, (iv) can effectively treat a blood vessel with a reduced risk of suffering vessel injuries that can lead to increased restenosis. In addition, the skilled artisan will certainly appreciate having an atherectomy device that (v) can handle these tight or tough lesions. In some embodiments, the atherectomy cutters and devices taught herein can be referred to as "hybrid" cutters and devices, due to their ability to cut through a combination of the soft and hard plaque, a function that will highly be appreciated by the skilled artisan.

SUMMARY

Atherectomy devices, and methods of using them are provided, namely devices and methods that (i) can effectively cut and remove the 4 different types of plaque tissue, namely calcified and hard, necrotic and soft, fibrotic, and a combination thereof; (ii) can render a concentric vessel lumen with minimal plaque burden; (iii) can safely self-collect and remove plaque particles to avoid release of emboli; (iv) can effectively treat a blood vessel with a reduced risk of suffering vessel injuries that can lead to increased restenosis; and, importantly, (v) can also handle tight or tough lesions having little to no luminal opening in the lesion. The atherectomy devices taught herein can be telescoping, self-driving, lateral pushing, or a combination thereof.

In some embodiments, the atherectomy device is a telescoping atherectomy device. In these embodiments, the device can have a distal end, a proximal end, a long axis, and a guidewire lumen passing through the device in the direction of the long axis. The device can include a flexible sheath having an outer diameter and a sheath lumen; a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a positive displacement pump that begins pumping at the distal end of the drive shaft and adjacent to the helical flutes at the proximal end of the cutter. And, in these embodiments, the cleared diameter of the cutter can be greater than the outer diameter of the flexible drive shaft; the flexible drive shaft can be longer than the flexible sheath to enable a reversible telescoping of the drive assembly from the lumen of the flexible sheath at the distal end of the flexible sheath; and, the guidewire lumen can include the cutter lumen and the driveshaft lumen.

In some embodiments, the cleared diameter of the cutter can be greater than the outer diameter of the flexible sheath. And, in some embodiments, the positive displacement pump can be a screw pump attached to the outer surface of the drive shaft, the distal end of the screw pump being adjacent to the helical flutes at the proximal end of the cutter.

In some embodiments, the telescoping atherectomy device can be self-driving. For example, the screw pump can extend beyond the flexible sheath and can be exposed for contact with a vascular lumen during use of the atherectomy device within the vascular lumen. In some embodiments, the screw pump can be a right hand screw when the cutter is rotated in the right-hand direction; and, in some embodiments, the screw pump can be a left hand screw when the cutter is rotated in the left-hand direction.

In some embodiments, the telescoping atherectomy device can further comprise a reversibly-expandable, lateral pushing member at the distal end of the flexible sheath. In some embodiments, the telescoping atherectomy device can further comprise a reversibly-expandable, lateral pushing member at the distal end of the flexible sheath, the lateral pushing member having a proximal end, a distal end, a collapsed state, and an expanded state, the proximal end having an operable connection with the flexible sheath, and the distal end having an operable connection with the cutter. The operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. Moreover, the operable connection with the cutter can be configured as a rotatably translatable connection to facilitate a rotation of the cutter and the flexible drive shaft without rotating the lateral pushing member during operation of the atherectomy device.

In some embodiments, the atherectomy device is a self-driving atherectomy device. In these embodiments, the device can have a distal end, a proximal end, a long axis, and a guidewire lumen passing through the device in the direction of the long axis. The device can include a flexible sheath having an outer diameter and a sheath lumen; a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a screw pump attached to the outer surface of the drive shaft and adjacent to the helical flutes at the proximal end of the cutter, the screw pump including a drive screw portion. In some embodiments, the drive screw portion can extend beyond the flexible sheath and can be exposed for contact with a vascular lumen during use of the atherectomy device within the vascular lumen. In some embodiments, the drive screw portion can be a right hand screw when the cutter is rotated in the right-hand direction; and, in some embodiments, the drive screw portion can be a left hand screw when the cutter is rotated in the left-hand direction. And, in these embodiments, the cleared diameter of the cutter can be greater than the outer diameter of the flexible drive shaft; and, the guidewire lumen can include the cutter lumen and the driveshaft lumen.

In some embodiments, the cleared diameter of the cutter of the self-driving atherectomy device can be greater than the outer diameter of the flexible sheath. And, in some embodiments, the drive screw portion can be the distal portion of the screw pump.

In some embodiments, the flexible drive shaft of the self-driving atherectomy device can be longer than the flexible sheath to enable a reversible telescoping of the drive assembly from the lumen of the flexible sheath at the distal end of the flexible sheath.

In some embodiments, the self-driving atherectomy device can further comprise a reversibly-expandable, lateral pushing member at the distal end of the flexible sheath. In some embodiments, the lateral pushing member can have a proximal end, a distal end, a collapsed state, and an expanded state, the proximal end having an operable connection with the flexible sheath, and the distal end having an operable connection with the cutter. The operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. Moreover, in some embodiments, the operable connection with the cutter can be configured as a rotatably translatable connection to facilitate a rotation of the cutter and the flexible drive shaft without rotating the lateral pushing member during operation of the atherectomy device.

In some embodiments, the atherectomy device is a lateral pushing atherectomy device. In these embodiments, the device can have a distal end, a proximal end, a long axis, and a guidewire lumen passing through the device in the direction of the long axis. The device can include a flexible sheath having an outer diameter and a sheath lumen. a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a positive displacement pump that begins pumping at the distal end of the drive shaft and adjacent to the helical flutes at the proximal end of the cutter. And, the lateral pushing atherectomy device can also have a reversibly-expandable, lateral pushing member at the distal end of the flexible sheath. In these embodiments, the cleared diameter of the cutter can be greater than the outer diameter of the flexible drive shaft; and, the guidewire lumen can include the cutter lumen and the driveshaft lumen.

In some embodiments, the cleared diameter of the cutter can be greater than the outer diameter of the flexible sheath.

In some embodiments, the lateral pushing member can have a proximal end, a distal end, a collapsed state, and an expanded state, the proximal end having an operable connection with the flexible sheath, and the distal end having an operable connection with the cutter. In some embodiments, the operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. And, in some embodiments, the operable connection with the cutter can be configured as a rotatably translatable connection to facilitate a rotation of the cutter and the flexible drive shaft without rotating the lateral pushing member during operation of the atherectomy device.

In some embodiments, the flexible drive shaft of the laterally pushing atherectomy device can be longer than the flexible sheath to enable a reversible telescoping of the drive assembly from the lumen of the flexible sheath at the distal end of the flexible sheath. And, in some embodiments, the laterally pushing atherectomy device can comprise a drive screw attached to the outer surface of the distal end of the drive shaft and adjacent to the screw pump at the distal end of the screw pump. The drive screw can extend beyond the flexible sheath and can be exposed for contact with a vascular lumen during use of the atherectomy device within the vascular lumen. In some embodiments, the drive screw can be a right hand screw when the cutter is rotated in the right-hand direction; and, in some embodiments, the drive screw can be a left hand screw when the cutter is rotated in the left-hand direction.

Systems are also provided. In some embodiments, any of the atherectomy devices taught herein can be a system comprising the atherectomy device and a guidewire.

Methods of performing an atherectomy in a subject using any of the atherectomy devices taught herein are provided. In some embodiments, the methods can include creating a point of entry in a vascular lumen of the subject; inserting the atherectomy device into the vascular lumen; telescoping the flexible drive shaft; cutting a plaque from the vascular lumen with the cutter of the atherectomy device; discharging the cut plaque from the vascular lumen with the positive displacement pump; and, removing the atherectomy device from the vascular lumen of the subject.

In some embodiments, the methods can include creating a point of entry in a vascular lumen of the subject; inserting the atherectomy device into the vascular lumen; driving the atherectomy device through the vascular lumen with the exposed drive screw; cutting a plaque from the vascular lumen with the cutter of the atherectomy device; discharging the cut plaque from the vascular lumen with the positive displacement pump; and, removing the atherectomy device from the vascular lumen of the subject.

Likewise, in some embodiments, the methods can include creating a point of entry in a vascular lumen of the subject; inserting the atherectomy device into the vascular lumen; pushing the distal portion of the atherectomy device laterally in the vascular lumen, the pushing including expanding the lateral pushing member; cutting a plaque from the vascular lumen with the cutter of the atherectomy device; discharging the cut plaque from the vascular lumen with the positive displacement pump; and, removing the atherectomy device from the vascular lumen of the subject.

In some embodiments, a hybrid atherectomy cutter for cutting a combination of soft and hard plaque is provided. The cutter can include a proximal end, a distal end, and a longitudinal axis, as well as a cutting length defined by the distance from the proximal end to the distal end along the longitudinal axis. The cutter can have a radius at the distal end, the radius having an inner inflection point and an outer inflection point; and, in some embodiments, the cutter can have a first primary cutting edge and a second primary cutting edge, the first primary cutting edge and the second primary cutting edge extending helically from the distal end to the proximal end and along the radius. The cutter can have a first helical flute and a second helical flute, each of the first helical flute and the second helical flute having a helix angle and forming a helical channel that is open at the distal end and the proximal end. The cutter can also have a cutting diameter, the cutting diameter being the maximum distance between the first primary cutting edge and the second primary cutting edge measured normal to the longitudinal axis. The cutter can also have a core having a core diameter, a distal end, and a proximal end; wherein, the distal end of the core is configured with a first plurality of secondary facets that form a first secondary cutting edge at the distal end of the first helical flute; and, a second plurality of secondary facets that form a second secondary cutting edge at the distal end of the second helical flute. And, the cutter can have a lumen configured for passage of a guidewire. Such cutters having the desired function of effectively cutting both soft and hard plaque in blood vessels.

One of skill will appreciate that the radius at the distal end of the cutter can have any desired shape. In some embodiments, the radius is a ball nose radius. In some embodiments, the radius is a corner radius. And, in some embodiments, the radius equals half the diameter of the cutter.

One of skill will appreciate that each of the flutes is helical in shape and can have a helix of any desired angle, such that a combination of flutes can have the same helix angle or have combination of helix angles. Moreover, the flutes of a cutter can have the same angle or a different angle when compared to the other flute or flutes where, for example, one of skill may choose a cutter of this configuration for a smoother cut. And, in some embodiments, the flute angle can be constant or variable where, for example, one of skill may choose the "variable helix", or variable flute angle between flutes, for materials that may be more resistant to cutting, and perhaps increase the efficiency of the cutting. A helix angle of greater than 45° is considered to be a "high angle" and will be more efficient at removing material from the cutting site and leave a smoother cut surface while reducing tissue packing and re-cutting of tissue; whereas, a helix angle of less than 40° is considered to be a "low angle" and may remove larger pieces of material for a given cutting time and leave a rougher cut surface while, perhaps, creating packing and recutting of tissue in some applications. In some embodiments, a flute can have a high helix angle; and, in some embodiments, a flute can have a low helix angle.

One of skill will recognize that the cutters include secondary facets that are created to produce secondary cutting edges. In some embodiments, the distal end of the core can be configured with a first plurality of secondary facets that form a first secondary cutting edge at the distal end of the first helical flute; and, in some embodiments, the distal end of the core can be configured with a second plurality of secondary facets that form a second secondary cutting edge at the distal end of the second helical flute.

The embodiments also include cutters having primary facets to improve cutting of tissue with the primary cutting edges. In some embodiments, the distal end of the core further comprises a plurality of first primary facets at the distal end of the first primary cutting edge; and, in some embodiments, the distal end of the core further comprises a plurality of second primary facets at the distal end of the second primary cutting edge. In some embodiments, the plurality of the first primary facets can be configured to extend the reach of the first primary cutting edge; and, likewise, the plurality of the second primary facets can be configured to extend the reach of the second primary cutting edge.

In some embodiments, the cutters can have a third primary cutting edge extending helically from the distal end to the proximal end and along the radius; and, a third helical flute having a helix angle and forming a helical channel that is open at the distal end and the proximal end. In some embodiments, the core can be further configured with a third plurality of secondary facets that form a third secondary cutting edge at the distal end of the third helical flute. Likewise, the core can be further configured with a third plurality of primary facets at the distal end of the third primary cutting edge, the third plurality of primary facets configured to extend the distal reach of the third primary cutting edge.

In some embodiments, the cutters can have a third primary cutting edge extending helically from the distal end to the proximal end and along the radius; a fourth primary cutting edge extending helically from the distal end to the proximal end and along the radius; a third helical flute having a helix angle and forming a helical channel that is open at the distal end and the proximal end; and, a fourth helical flute having a helix angle and forming a helical channel that is open at the distal end and the proximal end. In some embodiments, the core can be further configured with a third plurality of secondary facets that form a third secondary cutting edge at the distal end of the third helical flute; and, a fourth plurality of secondary facets that form a fourth secondary cutting edge at the distal end of the third helical flute. Likewise, the core can be further configured with a third plurality of primary facets at the distal end of the third primary cutting edge, the third plurality of primary facets configured to extend the distal reach of the third primary cutting edge; and, a fourth plurality of primary facets at the distal end of the fourth primary cutting edge, the fourth plurality of primary facets configured to extend the distal reach of the fourth primary cutting edge.

One of skill will appreciate that any of the atherectomy devices taught herein can include any of the cutters taught herein. In some embodiments, the atherectomy devices includes a cutter taught herein, the cutter having a cleared diameter; a distal end, a proximal end, a long axis, and a guidewire lumen passing through the device in the direction of the long axis; a flexible sheath having an outer diameter and a sheath lumen; a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath, the drive assembly also having a positive displacement pump that begins pumping at the distal end of the drive shaft and adjacent to the helical flutes at the proximal end of the cutter. In these embodiments, the cleared diameter of the cutter can be greater than the outer diameter of the flexible sheath; the flexible drive shaft can be longer than the flexible sheath to enable a reversible telescoping of the drive assembly from the lumen of the flexible sheath at the distal end of the flexible sheath; and, the guidewire lumen can include the cutter lumen and the driveshaft lumen.

In some embodiments, the atherectomy devices includes a cutter taught herein, the cutter having a cleared diameter; a distal end, a proximal end, a long axis, and a guidewire lumen passing through the device in the direction of the long axis; a flexible sheath having an outer diameter and a sheath lumen; a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath, the drive assembly also having a screw pump attached to the outer surface of the drive shaft and adjacent to the helical flutes at the proximal end of the cutter, the screw pump including a drive screw portion; wherein, the drive screw portion extends beyond the flexible sheath and is exposed for contact with a vascular lumen during use of the atherectomy device within the vascular lumen; and, is either a right hand screw when the cutter is rotated in the right-hand direction; or, a left hand screw when the cutter is rotated in the left-hand direction. In these embodiments, the cleared diameter of the cutter can be greater than the outer diameter of the flexible drive shaft; and, the guidewire lumen can include the cutter lumen and the driveshaft lumen.

In some embodiments, the atherectomy devices includes a cutter taught herein, the cutter having a cleared diameter; a distal end, a proximal end, a long axis, and a guidewire lumen passing through the device in the direction of the long axis; a flexible sheath having an outer diameter and a sheath lumen; a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath, the drive assembly also having a positive displacement pump that begins pumping at the distal end of the drive shaft and adjacent to the helical flutes at the proximal end of the cutter. And, the atherectomy device can also have a reversibly-expandable, lateral pushing member at the distal end of the flexible sheath, the lateral pushing member having a proximal end, a distal end, a collapsed state, and an expanded state, the proximal end having an operable connection with the flexible sheath, and the distal end having an operable connection with the cutter. In these embodiments, the cleared diameter of the cutter can be greater than the outer diameter of the flexible sheath; the guidewire lumen can include the cutter lumen and the driveshaft lumen. Moreover, the operable connection with the flexible sheath and the operable connection with the cutter can be each configured to receive an axial force (i) applied along the axis of the flexible drive shaft from the cutter to the flexible sheath and (ii) transferred through the lateral pushing member during the collapse and the expansion of the lateral pushing member with a reversible telescoping of the flexible drive shaft from the flexible sheath; and, the operable connection with the cutter can be configured as a rotatably translatable connection to facilitate a rotation of the cutter and the flexible drive shaft without rotating the lateral pushing member during operation of the atherectomy device.

One of skill will also appreciate that any of the methods of performing an atherectomy can include using any of the atherectomy devices taught herein with any of the cutters taught herein. Regardless of the atherectomy device used, the methods can include creating a point of entry in a vascular lumen of the subject; inserting the atherectomy device into the vascular lumen; telescoping the flexible drive shaft; cutting a plaque from the vascular lumen with the cutter of the atherectomy device; discharging the cut plaque from the vascular lumen with the positive displacement pump; and, removing the atherectomy device from the vascular lumen of the subject.

DETAILED DESCRIPTION

Atherectomy devices, and methods of using them are provided, namely devices and methods that (i) can effectively cut and remove the 4 different types of plaque tissue, namely calcified and hard, necrotic and soft, fibrotic, and a combination thereof, including fibrocalcific tissue; (ii) can render a concentric vessel lumen with minimal plaque burden; (iii) can safely self-collect and remove plaque particles to avoid release of emboli; (iv) can effectively treat a blood vessel with a reduced risk of suffering vessel injuries that can lead to increased restenosis. And, importantly, one of skill will certainly appreciate an atherectomy device that, surprisingly, (v) can also handle tight or tough lesions having little to no luminal opening in the lesion. In some embodiments, the atherectomy cutters and devices taught herein can be referred to as "hybrid" cutters and devices, due to their ability to cut through a combination of the soft and hard plaque, a function that will highly be appreciated by the skilled artisan. The atherectomy devices taught herein can be telescoping, self-driving, lateral pushing, or a combination thereof. The devices provided herein can, for example, render a concentric lumen with minimal plaque burden (<30% vessel diameter) while avoiding damage to vessel wall and minimizing embolization.

Figure 1A:
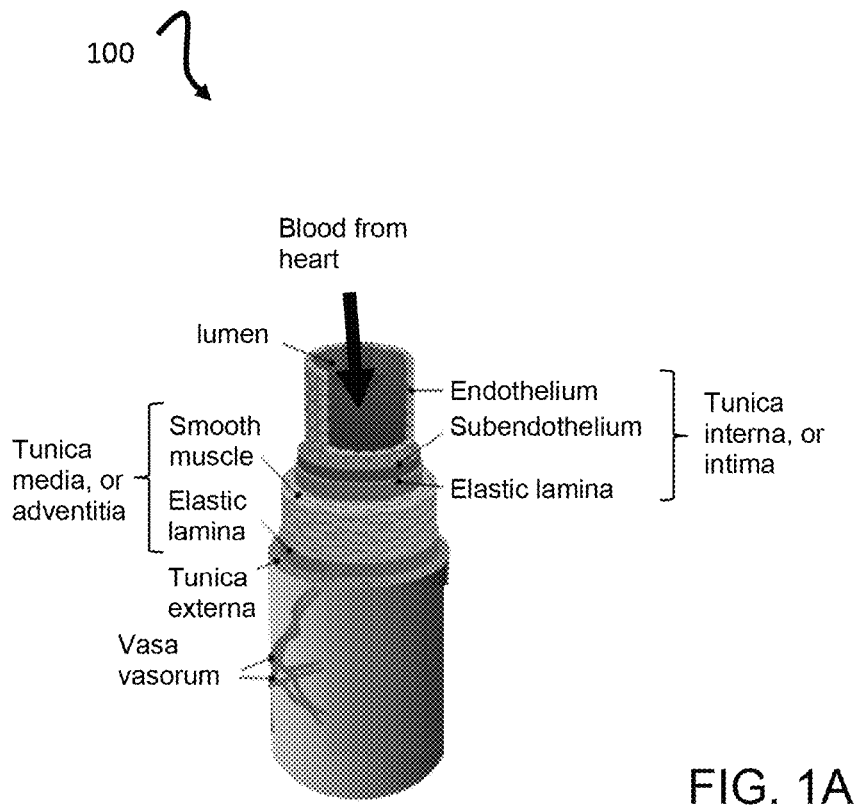
FIGS. 1A-1C illustrate the anatomy of an artery, intimal plaque, and a method of plaque removal, according to some embodiments.
Figure 1B:
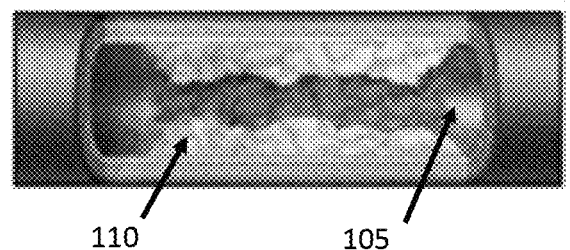
Figure 1C:
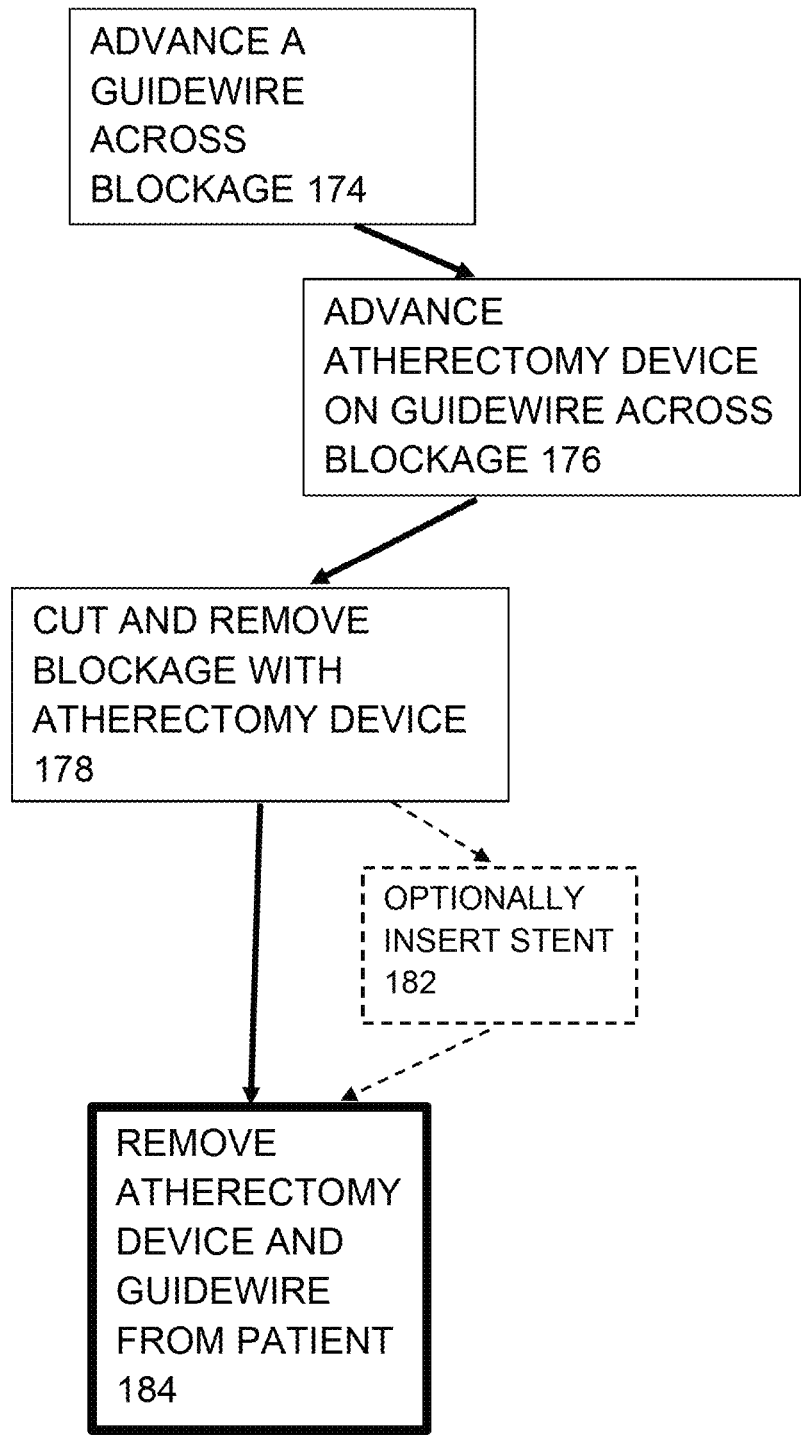

FIGS. 1A-1C illustrate the anatomy of an artery, intimal plaque, and a method of plaque removal, according to some embodiments. FIG. 1A illustrates the anatomy of an artery 100. The anatomy of arteries can vary by size of the artery, but arteries share common characteristics. They transport oxygenated blood from the heart and to smaller arterioles. The outermost layer is the tunica externa, or tunica adventitia, and is composed of collagen fibers. The largest arteries, like the aorta, also have vasa vasorum, or small blood vessels that supply oxygen to the large blood vessels. The next layer in is the tunica media, which is a combination of smooth muscle, collagen fiber, and is elastic. The next layer is the tunica interna or intima, which is also elastic with endothelial cells supported by a layer of collagen. These layers all surround the vascular lumen, which is the wall upon which the undesirable plaque forms and is removed with the atherectomy devices taught herein. FIG. 1B illustrates plaque 110 that has deposited on the wall of the arterial lumen 105.

Those of skill understand that guidewires can be used to locate a diseased region, or target region, in a blood vessel. Also, a guidewire can be used to direct the atherectomy devices taught herein, namely the cutter, over the target region. In some embodiments, the guidewire lumen can include the cutter lumen and the driveshaft lumen. In some embodiments, the guidewire lumen diameter can range in size from 0.01 to 0.20 inches, from 0.01 to 0.18 inches, from 0.01 to 0.15 inches, from 0.01 to 0.10 inches, or any range therein in some embodiments. In some embodiments, the guidewire lumen diameter can range from 0.01 to 0.14 inches. In some embodiments, the guidewire lumen diameter is 0.01 inches (0.254 mm), 0.02 inches (0.508 mm), 0.04 inches (1.016 mm), 0.06 inches (1.524 mm), 0.08 inches (2.032 mm), 0.10 inches (2.540 mm), 0.12 inches (3.048 mm), 0.14 inches (3.556 mm), 0.16 inches (4.064 mm), 0.18 inches (4.572 mm), 0.20 inches (5.080 mm), or any diameter therein in increments of 0.01 inches (0.254 mm).

FIG. 1C is a flowchart of an atherectomy method 150 that can be used with the atherectomy devices taught herein to remove plaque from an artery. A guidewire is advanced 174 through a guiding catheter and across a blockage in the blood vessel created by the arterial plaque in the target area. Once the guidewire is in place across the blockage, an atherectomy device is advanced 176 across the blockage on the guidewire. The atherectomy device is then in proper position to cut and remove 178 plaque in the target area to treat the artery and remove the blockage. At this time, a stent can optionally be inserted 180 in the target area to help maintain the newly created opening in the lumen. To complete the procedure, the atherectomy device and guidewire are removed 182 from the patient.

Generally speaking the atherectomy devices can include a cutter, or cutting head, that is attached to a drive shaft that rotates the cutter, and the drive shaft rotates within a sheath. The sheath can be interchangeably called a "flexible tube", in some embodiments; and, the drive shaft can be referred to as a "torque shaft", in some embodiments. In some embodiments, the cutter can be designed to telescope from the sheath and, in some embodiments, reversibly telescope from the sheath. In some embodiments, the cutter can extend out, or telescope, from the sheath as far as desired. For example, the cutter can telescope from, perhaps, 10 mm to 500 mm from the end of the sheath on the drive shaft in some embodiments. In some embodiments, the cutter can telescope from about 20 mm to about 200 mm, from about 30 mm to about 100 mm, from about 40 mm to about 80 mm, about 60 mm, or any range therein in increments of 1 mm. In some embodiments, the cutter can telescope about 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 300 mm, 400 mm, 500 mm, or any amount or range therein in increments of 1 mm. The telescoping allows the cutter and the distal portion of the drive shaft to advance ahead of the sheath during which an improved engagement between the cutter and the plaque tissue can be achieved. In addition, leaving the sheath static while moving the cutter in advance of the sheath allows the sheath to resist drill through. In some methods, the telescoping can be the sole step in the removal of plaque from a vessel. In some embodiments, the telescoping can provide an initial cutting path to facilitate a subsequent and more target-specific eccentric cutting.

PET, or a combination thereof. In some variations, the drive shaft can include a rigid material such as plastic, rendered flexible by incorporation of a spiral relief or groove. During a procedure, the motor drives the gear to rotate drive shaft and cutter to cut the tissue in a target lesion.

One of skill will appreciate that the "cleared diameter" of a vessel can be used to describe the diameter of the lumen of the blood vessel after passage of the cutter portion of the atherectomy device through the lumen of the vessel. Since the vessel is often elastic, the cleared diameter 260 of the lumen of a blood vessel may or may not be equal to the diameter of the cutter 230. The cleared diameter 260 of the cutter 230 can be greater than the outer diameter of the flexible drive shaft 250. In some embodiments, the cleared diameter of the cutter can be greater than the outer diameter of the flexible sheath. And, in some embodiments, the cleared diameter 260 of the lumen is less than the diameter of the body of the cutter 230.

Table 1 lists example arterial lumen diameters in mm, beginning at the aorta and descending down a human leg, for example. Peripheral vascular disease in the legs is an example of a condition that can be treated using the atherectomy devices taught herein.

TABLE 1

Examples of arterial lumen diameters in mm.

| Aorta (mm) | Superior femoral artery (mm) | Popliteal artery (mm) | Anterior tibial artery (mm) | Tibioperoneal trunk (mm) | Posterior tibial arteries (mm) | Peroneal arteries (mm) |
| --- | --- | --- | --- | --- | --- | --- |
| 17-35 | 5-7 | 3.5-4.5 | 3.0 | 2.5 | 2.0 | 2.0 |

Figure 2A:
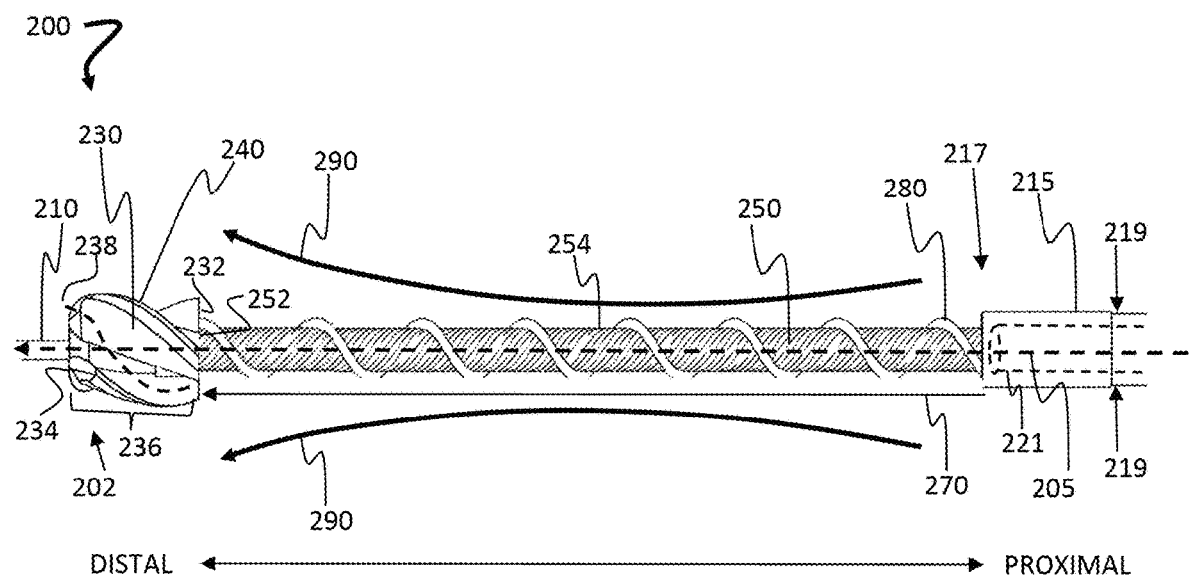
FIGS. 2A and 2B illustrate a telescoping atherectomy device, according to some embodiments.
Figure 2B:
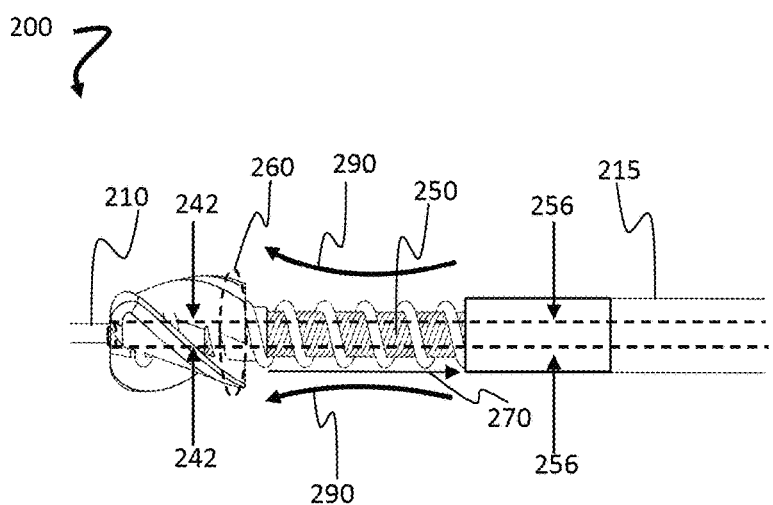

FIGS. 2A and 2B illustrate a telescoping atherectomy device, according to some embodiments. In these embodiments, the atherectomy device 200 can have a distal portion with a distal end 202, a proximal portion with a proximal end (not shown), a long axis having a central axis 205, and a guidewire lumen passing through the device in the direction of the central axis 205 for a guidewire 210. For perspective, the general direction of orientation from proximal to distal, and distal to proximal, are illustrated in FIG. 2A. The device can include a flexible sheath 215 having a proximal portion with a proximal end (not shown), a distal portion with a distal end 217, an outer diameter 219, and a sheath lumen 221; a drive shaft 250; a cutter 230 having a proximal portion with a proximal end 232, a distal portion with a distal end 234, and a body 236 with a plurality of helical flutes 238 between the cutter blades 240. The distal end 234 can have a plurality of cutting lips on the cutter blades 240, and, in some embodiments, the distal end 234 can have a point. The cutter can have a cutter lumen 242, and a cleared diameter 260.

The drive shaft can be made using any construct known to one of skill that meets the axial stiffness, flexural stiffness, torsional stiffness, and the like. In some embodiments, for example, the drive shaft includes a distal end and a proximal end, in which the distal end connects to or affixed to the cutter, and the proximal end connected to a rotatable element such as a gear attached to a motor or attached to motor itself. The drive shaft may be, in turn, driven by the motor in the handle. The drive shaft can be made using a metal braid and/or one or more metal coils, and one or more portions of the drive shaft embedded in a polymer. In some embodiments, the polymer can include PEBAX, polyurethane, polyethylene, fluoropolymers, parylene, polyimide, PEEK, the superior femoral artery, located about mid-femur, generally has a diameter of about 5 to 7 mm, or about 0.2 to 0.25 inch. As the artery descends below the knee, the popliteal artery generally has a diameter of about 4 to 4.5 mm (0.157 inch to 0.177 inch), and then reduces to about 3.5 mm (0.137 inch) as you move in the direct of the subject's foot. The popliteal artery branches again into the anterior tibial artery and the tibioperoneal trunk, reducing further in diameter to about 3.0 mm and then about 2.5 mm or about 0.118 inch to 0.098 inch. The tibioperoneal trunk further subdivides into the posterior tibial and peroneal arteries, further reducing in diameter to about 2.0 mm (0.078 inch). Generally speaking, the diameters of the peripheral arteries of the leg can vary, typically, from about 2 mm to about 7 mm. Any blood vessel can contain plaque and be a prospective target area for the atherectomy devices taught herein. For example, coronary arteries are about 3 mm in size, varies from 2.5-4.5 in diameter, and coronary arteries are prospective target areas for the atherectomy devices taught herein.

Although it seems reasonable to simply increase the diameter of the cutter for larger blood vessels, the skilled artisan will realize that the diameter of the cutter can also be limited by physical complications of the patient's anatomy. For example, there can be complications that occur during surgery due to bleeding at the arterial puncture access, tortuous vessels, vessel size variations, and the like. The diameter of the cutter can range from about 0.70 mm to about 2.20 mm in some embodiments, 1.00 mm to 2.20 mm in some embodiments, 1.20 mm to 2.20 mm in some embodiments, 1.40 mm to 2.20 mm in some embodiments, 1.50 to 2.20 mm in some embodiments, or any range therein in increments of 0.10 mm. In some embodiments, the diameter of the cutter can be about 0.90 mm, 1.00 mm, 1.10 mm, 1.20 mm, 1.30 mm, 1.40 mm, 1.50 mm, 1.60 mm, 1.70 mm 1.80 mm, 1.90 mm, 2.00 mm, 2.10 mm, 2.20 mm, 2.30 mm, or any diameter therein, or range therein, in increments of 0.05 mm. This is significant, as blood vessel lumen diameters can be very small or quite large, and vessels having diameters of 1.00 mm are quite tight for cutters, and vessels having diameters over about 2.30 mm are becoming larger than a cutter can be made, in some embodiments. The skilled artisan will recognize that eccentric cutting allows for cutting a larger region than the diameter of the cutter assembly without adding or exchanging the cutter for other larger tools for removal. The cutter can be biased off-center within the larger blood vessels to clear a lumen that is larger than the diameter of the cutter.

The skilled artisan will also realize that the length of the cutter has to be limited to have the maneuverability needed. One of skill will realize that the size of the cutter can be any size known to be suitable in the art for the particular treatment. In some embodiments, the length of the cutter can range from about 0.50 mm to about 3.00 mm, from about 0.60 mm to about 2.80 mm, from about 0.80 mm to about 2.60 mm, from about 1.00 mm to about 2.40 mm, from about 1.00 mm to about 2.20 mm, from about 1.00 mm to about 2.00 mm, from about 1.20 mm to about 1.80 mm, or any range therein in increments of 0.10 mm.

The atherectomy device 200 further includes a drive assembly to drive the cutter 230. The drive assembly can have a flexible driveshaft 250 including a long axis having a central axis that can be coincident with the central axis 205 of the atherectomy device 200. The flexible driveshaft 250 can further have a proximal portion with a proximal end (not shown), a distal portion with a distal end 252, an outer surface 254, and a driveshaft lumen 256, the distal end 252 of the flexible drive shaft 250 having a fixed connection with the cutter 230. The flexible drive shaft 250 can be rotatably translational with the lumen 221 of the flexible sheath 215. The drive shaft 250 can extend to reach a driving engine located outside the subject receiving the atherectomy, the driving engine powered by an electric engine, in some embodiments, or powered by an air compressor in some embodiments, and the drive shaft 250 can be operably connected to a handle (not shown) at the proximal end of the atherectomy device for control by a user. The drive assembly can also have a positive displacement pump that pumps from the distal portion of the drive shaft 250 and adjacent to the helical flutes 238 at the proximal end of the cutter 230. In some embodiments, the positive displacement pump extends from the distal portion of the drive shaft 250 to the proximal portion of the driveshaft 250 to pump cut pieces of arterial plaque from a blood vessel.

One of skill will appreciate that the subject is a patient that is receiving the atherectomy. The term "subject" and "patient" can be used interchangeably and refer to an animal such as a mammal including, but not limited to, non-primates such as, for example, a cow, pig, horse, cat, dog, rabbit, rat and mouse; and primates such as, for example, a monkey or a human. The subject can also be a cadaver, in some embodiments, or a portion of a cadaver.

The flexible drive shaft 250 can be longer than the flexible sheath 215 to enable a reversible telescoping 270 of the drive assembly from the lumen 221 of the flexible sheath 215 at the distal end 252 of the flexible sheath 215. The guidewire lumen can include the cutter lumen 242 and the driveshaft lumen 256. Although the flexural stiffness of the drive shaft 250 remains the same between the collapsed and expanded states of the device, the flexural movement 290 increases upon the telescoping 270 of the drive shaft from the flexible sheath 215. As such, the amount of flexural movement 290 available is greater in FIG. 2A than in FIG. 2B, and the ease of flexural movement 290 is greater in FIG. 2A than in FIG. 2B due to the length of the drive shaft that has been telescoped in FIG. 2A as opposed to the length of the drive shaft exposed in FIG. 2B. We found that, as the amount and ease of flexural movement 290 increases due to the telescoping 270, the ease at which the cutter 230 can move through an artery increases.

In some embodiments, the cutter can be operably attached to the drive shaft using a friction fitting, so that the drive shaft is allowed slip on the base of the cutter when engaged with plaque and meeting a maximum torque limit. And, in some embodiments, the positive displacement pump can be a screw pump 280, also referred to as an Archimedes screw in some embodiments. The positive displacement pump can be attached to the outer surface 254 of the drive shaft 250, the distal end of the screw pump being adjacent to the helical flutes 238 at the proximal end 232 of the cutter 230 to transport pieces of cut plaque from the cutter in a distal to proximal direction to the proximal end of the atherectomy device for removal of the cut plaque from the subject.

Figure 3:
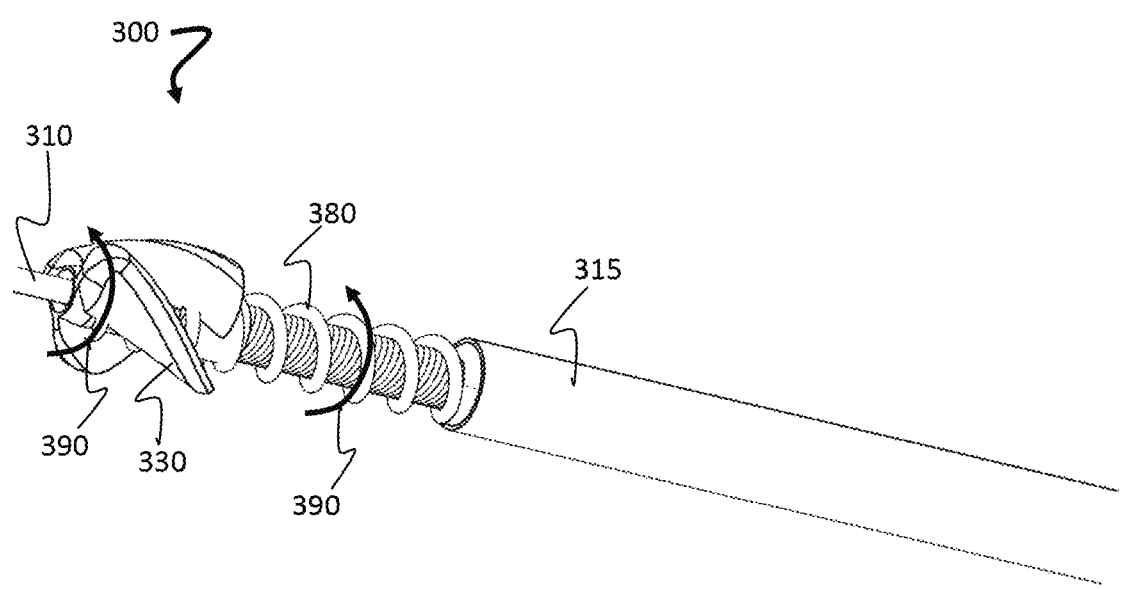
FIG. 3 illustrates a telescoping atherectomy device that can be self-driving, according to some embodiments.

FIG. 3 illustrates a telescoping atherectomy device that can be self-driving, according to some embodiments. The atherectomy device 300 can have a screw pump 380 in operable contact with a cutter 330, for example. The screw pump 380 can extend beyond the flexible sheath 315 and can be exposed for contact with a vascular lumen wall (not shown), often perhaps contact with remaining plaque on the lumen wall, during use of the atherectomy device within the vascular lumen. In some embodiments, the screw pump 380 can be a right hand screw (as shown) when the cutter 330 is rotated in the right-hand direction 390; and, in some embodiments, the screw pump 380 can be a left hand screw (opposite as shown) when the cutter 330 is rotated in the left-hand direction (opposite direction to 390). As such, a right-handed cutter can have a right-handed screw pump, and a left-handed cutter can have a left-handed screw pump, to enable the screw pump to assist in driving the atherectomy device 300 through the vascular lumen along the guidewire 310 during the cutting of the vascular plaque in the vascular lumen. One of skill will understand that a self-driving device can offer substantial value in that it can assist by reducing the forces needed from a surgeon, for example, during operation of the device. The self-driving can be all or partial, meaning that that the device can remove the need for the surgeon to push the device during the procedure, in some embodiments. And, in some embodiments, it eases the pressure required from the surgeon during the procedure. Those skilled in the art of atherectomy procedures will understand that pushing can cause the device to buckle, break, or jam; and/or, the patient can suffer complications through a perforation of a vessel receiving the treatment, as well as a perforation of a tissue surrounding the vessel receiving the treatment.

The self-driving feature of the atherectomy devices taught herein can reduce the pressure required from a surgeon performing the procedure. In some embodiments, the pressure required from the surgeon performing the atherectomy can be reduced by 100%, 95%, 90%, 85%, 80%, 75%, 70%, 65%, 60%, 55%, 50%, 45%, 40%, 35%, 30%, 25%, 20%, 15%, 10%, 5%, or any amount or range therein in increments of 1%. In some embodiments, the pressure required from the surgeon performing the atherectomy can be reduced in an amount ranging from about 25% to about 100%, from about 30% to about 100%, from about 35% to about 100%, from about 40% to about 100%, from about 45% to about 100%, from about 50% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%, or any range therein in increments of 1%. Likewise, in some embodiments, the pressure required from the surgeon performing the atherectomy can be reduced in an amount ranging from about 25% to about 95%, from about 30% to about 90%, from about 35% to about 85%, from about 40% to about 80%, from about 45% to about 75%, from about 50% to about 70%, from about 60% to about 100%, from about 65% to about 100%, from about 70% to about 100%, from about 75% to about 100%, from about 80% to about 100%, from about 85% to about 100%, from about 90% to about 100%, from about 95% to about 100%, or any range therein in increments of 1%. Likewise, in some embodiments, the pressure required from the surgeon performing the atherectomy can be reduced in an amount ranging from about 25% to about 50%, from about 50% to about 100%, or any range therein in increments of 1%. Likewise, in some embodiments, the pressure required from the surgeon performing the atherectomy can be reduced by at least 20%, at least 30%, at least 40%, at least 50%, at least 60%, at least 70%, at least 80%, at least 90%, or at least any range therein in increments of at 1%.

In some embodiments, a surgeon may need to apply a negative pressure, for example holding or pulling and not pushing, at times to aid control in the cutting of a lesion. It should be appreciated that the negative pressure can be a negative 1%, 5%, 10%, 15%, 20%, or 25%, or any amount therein in increments of 1%, in some embodiments. Such a negative pressure can result in slowing the forward movement of the cutting, stopping the cutting, or moving the cutting in a direction that opposes the self-driving direction of the cutter.

Those of skill in the art will appreciate that the atherectomy devices will offer a needed versatility and maneuverability in the art for tortuous blood vessels. When plaque is located in tortuous vessels or occluded eccentric to the passage of the vessel, eccentric cutting of the tissues can be useful to maneuver the cutting head to remove plaque. There have been atherectomy devices that offer a mechanism in the device that can create a curvature in the distal end of the device by pulling a "tendon" that pulls the end laterally. These devices suffer in that they create a "snapback" or "whip" motion of the device due to an imbalance of stresses being placed along the long axis of the atherectomy device. The devices provided herein provide eccentric cutting without the "snapback" or "whip" created by these earlier known mechanisms.

Figure 4A:
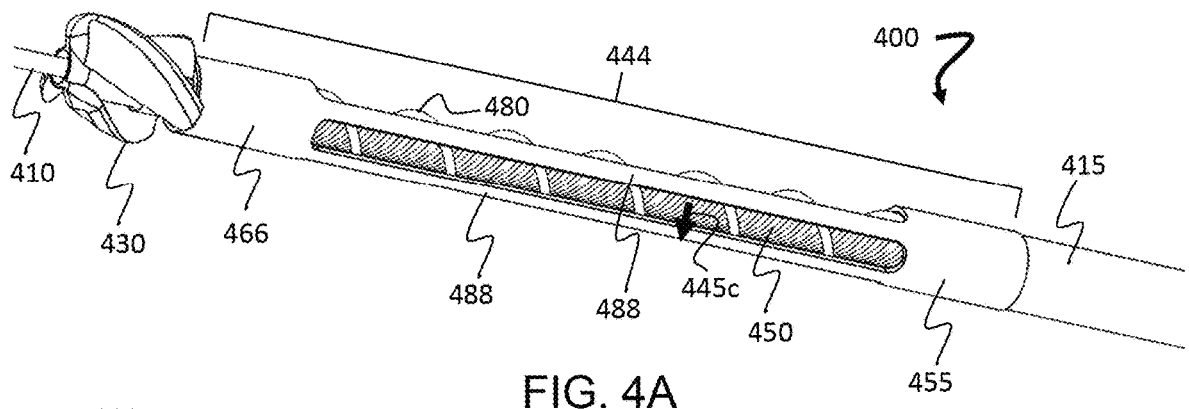
FIGS. 4A-4D illustrate a telescoping atherectomy device that can further comprise a reversibly-expandable, lateral pushing member at the distal end of the flexible sheath, wherein the expansion of the lateral pushing member induces a curve, according to some embodiments.
Figure 4B:
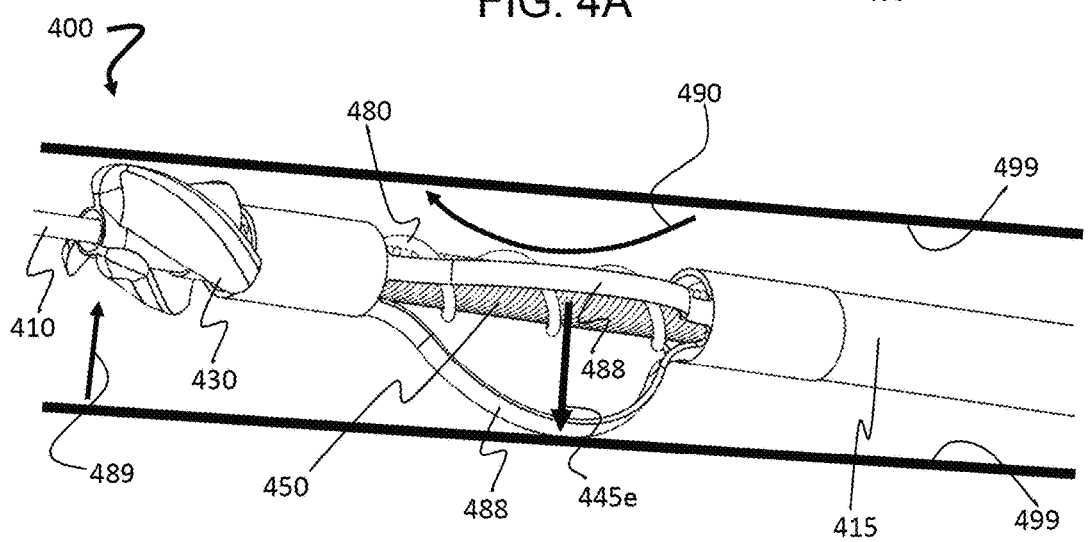
Figure 4C:
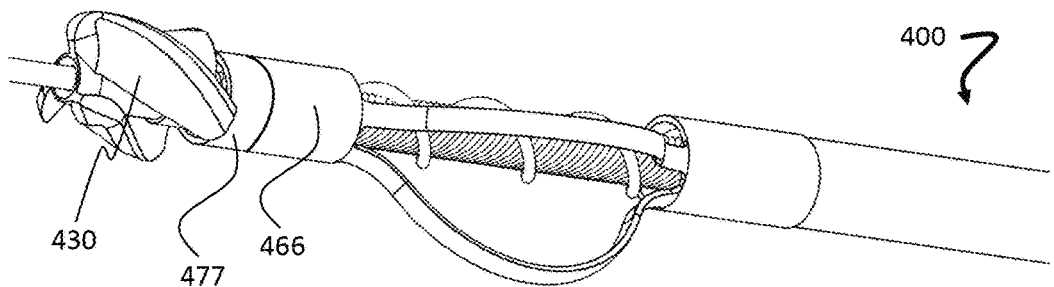

FIGS. 4A-4D illustrate a telescoping atherectomy device that can further comprise a reversibly-expandable, lateral pushing member at the distal end of the flexible sheath, wherein the expansion of the lateral pushing member induces a curve, according to some embodiments. As shown in FIG. 4A, the telescoping atherectomy device 400 can further comprise a reversibly-expandable, lateral pushing member 444 at the distal end of the flexible sheath 415, the pushing member 444 creating a lateral protrusion relative to the central axis of the atherectomy device. The lateral pushing member 444 can have a proximal portion with a proximal end, a distal portion with a distal end, and a reversibly-expandable portion having a collapsed state (as shown in FIG. 4A) and an expanded state (as shown in FIGS. 4B and 4C). The protrusion can be rotated relative to the lesion in any amount, from 1-360 degrees, or any range therein, for example, to reach any target area inside of a blood vessel.

The lateral pushing member can be made of any material known to be suitable by those of skill. For example, the lateral pushing member can be made of a flexible metal, a flexible metal that is biocompatible, such as titanium alloy such as Nickel Titanium. In some embodiments, the lateral pushing member can be made of a polymer such as PEEK, Polyimid or Nylon. The length of the trusses, or ribbon, can be designed to provide any desired protuberance. For example, the length of the trusses may vary from 1 mm-100 mm in some embodiments, 10 mm-30 mm in some embodiments, 10 mm to 40 mm in some embodiments, 10 mm to 50 mm in some embodiments, 20 mm to 60 mm in some embodiments, 20 mm to 80 mm in some embodiments, or any range therein. In some embodiments, the length of the trusses can be 1 mm, 2 mm, 4 mm, 6 mm, 8 mm, 10 mm, 12 mm, 14 mm, 16 mm, 18 mm, 20 mm, 30 mm, 40 mm, 50 mm, 60 mm, 70 mm, 80 mm, 100 mm, or any length therein in increments of 1 mm.

The reversibly-expandable portion has trusses 488 that expand and collapse the reversibly-expandable lateral pushing member 444 through the application of axial forces on the lateral pushing member 444. The trusses can be referred to as "ribbons", in some embodiments. The proximal end of the lateral pushing member 444 has an operable connection with the flexible sheath 415, and the distal end of the lateral pushing member 444 has an operable connection with the cutter 430. The operable connection with the flexible sheath 415 and the operable connection with the cutter 430 can each be configured to receive an axial force (i) applied along the axis of the flexible drive shaft 450 from the cutter 430 to the flexible sheath 415 and (ii) transferred through the lateral pushing member 444 to expand the lateral pushing member 444 when applying a distal to proximal axial force, and the collapse the lateral pushing member 444 when applying a proximal to distal axial force, the axial forces applied in the desired direction with the reversible telescoping action of the flexible drive shaft 450 within the flexible sheath 415. The lateral pushing member 444 has an effective radius upon collapse 445c and upon expansion 445e.

In some embodiments, proximal-to-distal and distal-to-proximal forces are received by the lateral pushing member 444 at a proximal collar 455 on the proximal portion of the lateral pushing member 444 and at a distal collar 466 on the distal portion of the lateral pushing member 444. Moreover, the operable connection between the lateral pushing member 444 and the cutter 430 can be configured as a rotatably translatable connection to facilitate a rotation of the cutter 430 and the flexible drive shaft 450 without rotating, or undesirably torquing, the distal end of the lateral pushing member 444 during operation of the atherectomy device 400.

The axial forces can be applied using any structure, a centralized member, for example a tendon, that applies the force along the central axis of the drive shaft to avoid inducing a load on the atherectomy device resulting in release of the snapback or whip forces along the long axis of the device. In some embodiments, the structure providing the axial force can be the drive shaft that is already located central to the device, for example, concentric within the sheath. As such, in some embodiments, the method of expanding the lateral pushing member includes applying a distal-to-proximal force to the distal portion of the lateral pushing member, the force applied along the central axis of the atherectomy device, the central axis of the drive shaft, or the central axis of the sheath.

The contact of the lateral pushing member 444 on the vessel wall laterally pushes the cutter 430 away from the central axis of the vessel lumen opposite direction of expansion of the trusses 488. The magnitude of the diversion of the cutter 430 is adjustable and controllable.

As shown in FIG. 4B, the expansion of the trusses 488 on the lateral pushing member 444 causes the cutter 430 of the atherectomy device 400 to deflect toward the vascular lumen wall 499 that is opposite the vascular lumen wall 499 receiving force from the expansion of the trusses 488.

One or more expandable trusses can be used. In some embodiments, there is a single truss. In some embodiments, there are 2 trusses. In some embodiments, there are 3 trusses. In some embodiments, there are 4 trusses. In some embodiments, there are at least 1, 2, 3, 4, 5, 6, 7, 8, 9, or 10 trusses. The trusses can be pre-shaped to create a biased curve or angle to protrude outwardly from the central axis of the device. That is, in some embodiments, the trusses have a shape memory that allows the trusses to remain in the collapsed state, and the expanded state is obtained by applying a force to the trusses, for example, by pulling on the central tendon, or drive shaft. In some embodiments, the trusses have a shape memory that allows the trusses to remain in the expanded state, and the collapsed state is maintained by holding the trusses in the collapsed state, and the expanded state is obtained by releasing that holding force and allowing the shape memory to return to the trusses. The trusses can be any shape and, in some embodiments, can be a single truss or a plurality of trusses. In some embodiments, the trusses can for a basket shape. In some embodiments, a balloon can be inflated to bias the cutter, rather than use a truss or trusses. For example, the trusses can be arched or angled ribbons, for example, that help to stabilize the flexible drive shaft.

The eccentric cutting of the devices provided herein can offer safe and clean cutting in tortuous and non-tortuous vessels, as well as eccentric lesions. The lateral pushing member 444 increases safety because, without such lateral protrusion, the cutter assembly is biased to move towards the outer side of the vessel curvature, which may accidently cut the vessel wall instead of the targeted plaque at the inner side of the vessel. The lateral pushing member 444 addresses that problem by correcting the bias by bulging the trusses 488 towards the outer side of the vessel curvature to laterally push the cutter to the opposite side of the blood vessel to achieve more controlled, effective, and safe cutting than conventional cutters. When debulking an eccentric lesion, for example, the adjustable lateral pushing enables the cutter assembly to target specifically towards the side of the vessel having the greater amount of the stenotic material to achieve eccentric cutting.

In some embodiments, the effective cutting diameter may be approximately half the diameter of the cutter plus the lateral extent of the protrusion from central axis of cutter. For example, if the cutter is 2.2 mm in diameter, and the protrusion is extended 3.0 mm from cutter axis, the effective cutting diameter is 4.1 mm. As can be seen, the eccentric cutting leads to a cutting area that is much larger than the diameter of the cutter.

The magnitude of the protrusion (from slightly protruded to maximally protruded) is adjustable, in some embodiments. For example, the distance between the two ends or collar of the lateral pushing member can be adjusted. That is, the distance between the two ends or collars of the lateral pushing member can be set as desired. In some embodiments, the distance between the collars is increased to reduce the expansion of the trusses and, thus, reduce the deflection of the cutter. Likewise, the distance between the collars can be decreased to increase the expansion of the trusses and, thus increase the deflection of the cutter. One of skill will appreciate that a dial, knob, button, or other actuator on the device can provide the user of the device with a measure of the distance between the collars of the lateral pushing member 444. In some embodiments, an increase in the distance that the drive shaft has moved relative to the sheath increases the expansion of the trusses 488. Likewise, in some embodiments, a decrease in the distance that the drive shaft has moved relative to the sheath decreases the expansion of the trusses 488.

In some embodiments, the proximal portion or proximal end of the lateral pushing member 444 will have a fixed contact with the distal portion or distal end of the sheath, and the distal portion or distal end of the drive shaft will have a rotatably translational connection with the cutter; with a component proximal to the cutter, the component including a race and a step to allow for rotation of the cutter despite the presence of the drive shaft. The race can be referred to as a "bearing surface" in some embodiments. The component can be, for example, a fixed race or bearing; and the like, such that the drive shaft freely rotates at the distal portion or distal end of the laterally pushing member while the laterally pushing member does not rotate.

Interestingly, it was discovered that the relative flexural stiffness of the drive shaft 450 as compared to the trusses 488 can also help control which portion of the cutter 430 makes contact with, and cuts, plaque on the vascular lumen wall 499. For example, if the flexural stiffness of the drive shaft 450 is greater than the flexural stiffness of the trusses 488, then the expansion of the trusses 488 will likely not cause a deformation 490 of the drive shaft 450, and the contact between the cutter 430 and the vascular lumen wall 499 will occur moreso on the side of the body of the cutter 430. However, if the flexural stiffness of the drive shaft 450 is less than the flexural stiffness of the trusses 488, the drive shaft 450 is expected to deform, and the contact between the cutter 430 and the vascular lumen wall 499 will begin to occur moreso toward the distal end of the cutter 430.

In some embodiments, the flexural stiffness of the distal portion of the flexible atherectomy device, $F_D$, is less than or equal to the flexural stiffness of the lateral pushing member, $F_{LPM}$. In some embodiments, the flexural stiffness of the distal portion of the flexible atherectomy device, $F_D$, is greater than or equal to the flexural stiffness of the lateral pushing member, $F_{LPM}$. In some embodiments, the flexural stiffness of the distal portion of the flexible atherectomy device, $F_D$, is greater than the flexural stiffness of the lateral pushing member, $F_{LPM}$.

$F_D$ can be reduced relative to $F_{LPM}$ by 75%, 70%, 65%, 60%, 55%, 50%, 45%, 40%, 35%, 30%, 25%, 20%, 15%, 10%, 5%, or any amount or range therein in increments of 1%. In some embodiments, $F_D$ can be reduced relative to $F_{LPM}$ in an amount ranging from about 25% to about 80%, from about 30% to about 75%, from about 35% to about 75%, from about 40% to about 75%, from about 45% to about 75%, from about 50% to about 75%, from about 60% to about 75%, from about 65% to about 75%, from about 70% to about 75%, or any range therein in increments of 1%. Likewise, in some embodiments, $F_D$ can be reduced relative to $F_{LPM}$ in an amount ranging from about 25% to about 50%, from about 30% to about 50%, from about 35% to about 50%, from about 40% to about 50%, from about 45% to about 50%, or any range therein in increments of 1%.

Likewise, in some embodiments, $F_D$ can be reduced relative to $F_{LPM}$ in an amount ranging from about can be reduced by at least 20%, at least 30%, at least 40%, at least 50%, at least 60%, at least 70%, at least 80%, at least 90%, or at least any range or amount therein in increments of at 1%.

Given this information, one of skill will appreciate that the amount of deformation can be selected by selecting the relative ratios of flexural stiffness of the drive shaft 450 and the trusses 488, which will allow additional control of the cutter to the user of the atherectomy device. As such, in some embodiments, the atherectomy device 400 can be designed such that the flexural stiffness of the trusses 488 is greater than the flexural stiffness of the drive shaft 450 to obtain a desired amount of deflection of the drive shaft to direct a desired surface of the cutter 430 to the vascular lumen wall 499. In some embodiments, the flexural stiffness of the drive shaft can be equal to or greater than the flexural stiffness of the trusses 488 to avoid a deflection of the drive shaft. One of skill will appreciate that there are methods to vary the flexural stiffness of the drive shaft. The stiffness or flexibility of the drive shaft may be adjusted, for example, by varying the orientation or association of the filaments that compose the drive shaft. In some embodiments, to increase flexural stiffness, the filaments on the shaft can be bound together with stiffer material, or the flexural stiffness can be increased (or reduced) by increasing (or decreasing) the filament size.

The lateral pushing member can be designed to expand to a curved protuberance. In some embodiments, the lateral pushing member can collapse to have an effective radius 445c that is less than or equal to the radius of the sheath. In some embodiments, the lateral pushing member can collapse to have an effective radius 445c that is less than or equal to the radius of the cutter. In some embodiments, the lateral pushing member collapses to have an effective radius 445c that is less than or equal to the radius of the cleared diameter of the cutter to help facilitate movement of the device in the blood vessel.

Torsional stress on the lateral pushing member 444 is a design consideration. In order to reduce the concerns about the torsional stress induced on the lateral pushing member 444, the torsional stress on the distal end of the lateral pushing member can be reduced, the torsional stiffness of the lateral pushing member can be increased, or both of these design modifications can be implemented.

FIG. 4C provides an alternate operable connection between the cutter and the lateral pushing member to address torsional stresses, according to some embodiments. In some embodiments, the distal race is fixed and serves as a bearing race against the rotating cutter 430. In some embodiments, however, the distal race 477 rotates in contact with a rotating cutter 430 and the distal collar 466 of the lateral pushing member 444. As such, the distal race 477 can be freely rotating, in which the distal race 477 freely rotates to further reduce the torsional stress on the lateral pushing member 444. In some embodiments, the distal race 477 can be made of a low friction material, such as TEFLON.

Figure 4D:
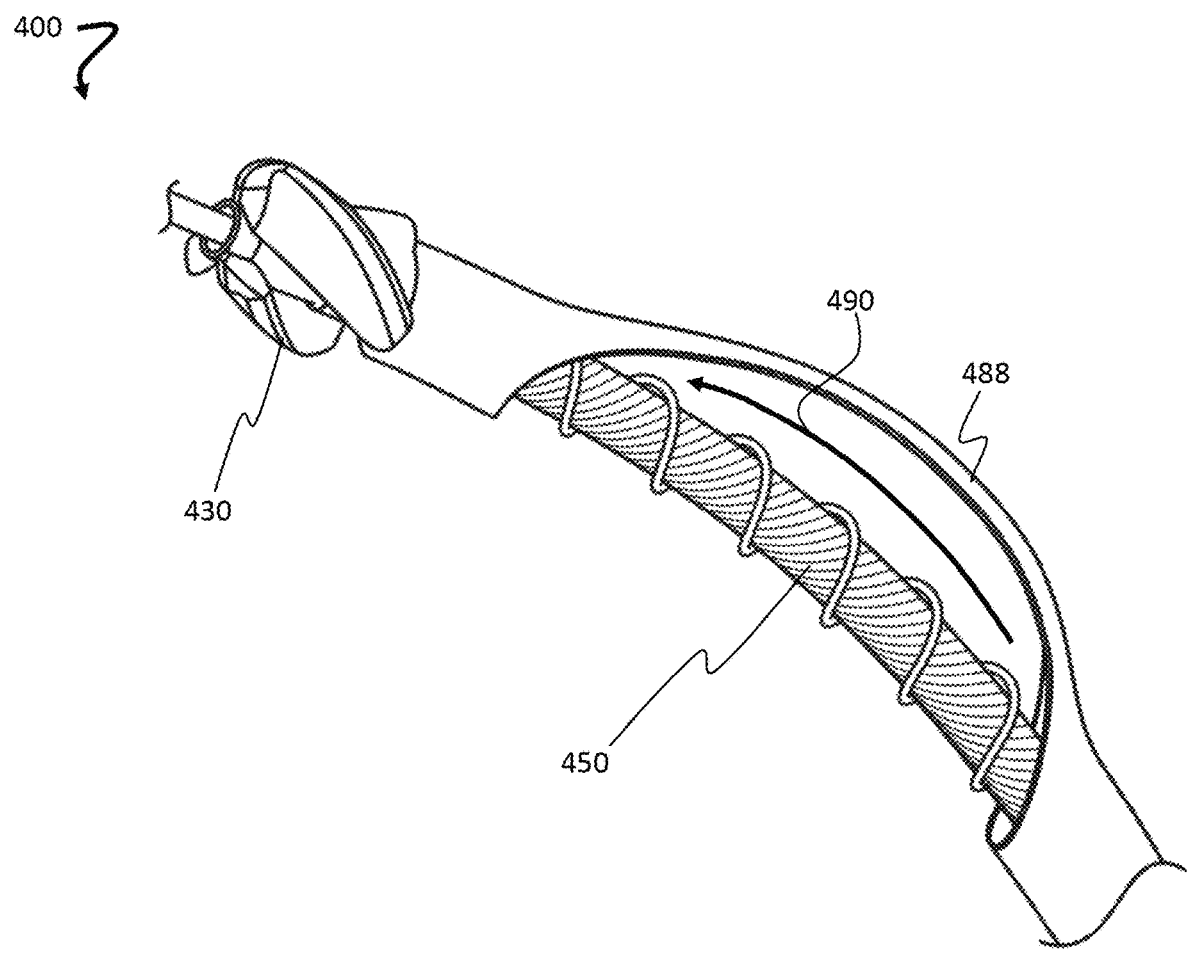

FIG. 4D illustrates how a curve can be induced in the distal portion of the atherectomy device as deformation 490. As discussed herein, the relative flexural stiffnesses of the distal portion of the drive shaft 450 and the lateral pushing member can induce the formation of the curve as force is applied to induce lateral expansion of trusses 488, as described above, also changing the orientation of the cutter 430 in the vessel lumen (not shown). The deformation 490 can be returned to a straight position as shown in FIB. 4B by telescoping the drive shaft 450 out from the sheath 415. This re-aligns the cutter 430 in the vessel lumen (not shown), from a position where the distal cutter is oriented to cut, to a position where the side of the cutter 430 is oriented to cut.

It should be appreciated that each of the telescoping feature, the self-driving feature, and the lateral pushing feature are distinct technical advantages. As such, the atherectomy device can be a self-driving atherectomy device only, meaning the device doesn't require telescoping or lateral pushing. In these embodiments, the components of which can be labeled the same or similar to the other embodiments taught herein, the device can have a distal portion with a distal end, a proximal portion with a proximal end, a long axis with a central axis, and a guidewire lumen passing through the device in the direction of the long axis. The device can include a flexible sheath having an outer diameter and a sheath lumen; a cutter having a proximal end, a distal end, and a body with a plurality of helical flutes. There can also be a point at the distal end of the cutter having a plurality of cutting lips, as well as a cutter lumen, and a cleared diameter. These devices also include a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a screw pump attached to the outer surface of the drive shaft and adjacent to the helical flutes at the proximal end of the cutter. The screw pump can include a drive screw portion. In some embodiments, the drive screw portion can be the distal portion of the screw pump.

To be self-driving, for example, the drive screw portion can extend beyond the flexible sheath and can be exposed for contact with a vascular lumen during use of the atherectomy device. To effectively assist in driving the device through the vascular lumen, the drive screw should turn in the same direction as the cutter. For example, if the flutes of the cutter spiral in the right hand direction the drive screw should spiral in the right hand direction. Likewise, if the flutes of the cutter spiral in the left hand direction the drive screw should spiral in the left hand direction. As such, in some embodiments, the drive screw portion can be a right hand screw when the cutter is rotated in the right-hand direction; and, in some embodiments, the drive screw portion can be a left hand screw when the cutter is rotated in the left-hand direction.

The relative size of the lumen, the cutter, and the drive screw can be designed to optimize the self-driving feature. In these embodiments, the cleared diameter of the cutter can be greater than the outer diameter of the flexible drive shaft; and, in some embodiments, the cleared diameter of the cutter can be greater than the outer diameter of the flexible sheath.

Of course, any of the self-driving devices can also include a telescoping feature, the components of which can be labeled the same or similar to the other embodiments taught herein. For example, the flexible drive shaft of the self-driving atherectomy device can be longer than the flexible sheath to enable a reversible telescoping of the drive assembly from the lumen of the flexible sheath at the distal end of the flexible sheath.

Moreover, any of the self-driving devices can also include a reversibly-expandable, lateral pushing member, the components of which can be labeled the same or similar to the other embodiments taught herein. In some embodiments, the lateral pushing member can have a proximal end, a distal end, a collapsed state, and an expanded state, the proximal end having an operable connection with the flexible sheath, and the distal end having an operable connection with the cutter. The operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. Moreover, in some embodiments, the operable connection with the cutter can be configured as a rotatably translatable connection to facilitate a rotation of the cutter and the flexible drive shaft without rotating the lateral pushing member, particularly the distal portion of the lateral pushing member, during operation of the atherectomy device.

Likewise, the atherectomy device can be a lateral pushing atherectomy device only, a device doesn't require self-driving, the components of which can be labeled the same or similar to the other embodiments taught herein. It does require telescoping, however, at least to the extent needed for an expanding and a collapsing of the lateral pushing member. In these embodiments, the device can have a distal end, a proximal end, a long axis, and a guidewire lumen passing through the device in the direction of the long axis. The device can include a flexible sheath having an outer diameter and a sheath lumen. The device can have a cutter having a proximal end, a distal end, and a body with a plurality of helical flutes, a point at the distal end having a plurality of cutting lips, a cutter lumen, and a cleared diameter; and, a drive assembly. The drive assembly can have a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath. The drive assembly can also have a positive displacement pump that begins pumping at the distal end of the drive shaft and adjacent to the helical flutes at the proximal end of the cutter. And, the lateral pushing atherectomy device can also have a reversibly-expandable, lateral pushing member at the distal end of the flexible sheath.

The relative size of the lumen and the cutter can be designed to optimize movement of the atherectomy device through the lumen. For example, the cleared diameter of the cutter can be greater than the outer diameter of the flexible drive shaft. In some embodiments, the cleared diameter of the cutter can be greater than the outer diameter of the flexible sheath. The size of the cutter lumen and the drive shaft lumen can be configured for passage of a guidewire of a desired gauge and, accordingly, the guidewire lumen can include the cutter lumen and the driveshaft lumen.

In some embodiments, the lateral pushing member can have a proximal portion with a proximal end, a distal portion with a distal end, a collapsed state, and an expanded state, the proximal end having an operable connection with the flexible sheath, and the distal end having an operable connection with the cutter. In some embodiments, the operable connection with the flexible sheath and the operable connection with the cutter can each be configured to receive an axial force (i) applied along the axis of the flexible drive shaft from the cutter to the flexible sheath and (ii) transferred through the lateral pushing member during the collapse and the expansion of the lateral pushing member with the reversible telescoping of the flexible drive shaft from the flexible sheath. And, in some embodiments, the operable connection with the cutter can be configured as a rotatably translatable connection to facilitate a rotation of the cutter and the flexible drive shaft without rotating the lateral pushing member during operation of the atherectomy device.

In some embodiments, atherectomy device can also be telescoping, the components of which can be labeled the same or similar to the other embodiments taught herein. That is, the flexible drive shaft of the laterally pushing atherectomy device can be longer than necessary for the expansion of the lateral pushing member. The flexible drive shaft of the laterally pushing atherectomy device can be longer than flexible sheath to enable a reversible telescoping of the drive assembly from the lumen of the flexible sheath at the distal end of the flexible sheath.

And, in some embodiments, the lateral pushing atherectomy device can also be self-driving, the components of which can be labeled the same or similar to the other embodiments taught herein. That is, the lateral pushing atherectomy device can comprise a drive screw attached to the outer surface of the distal end of the drive shaft and adjacent to the screw pump at the distal end of the screw pump. The drive screw can be a part of the screw pump, and it can extend beyond the flexible sheath and be exposed for contact with a vascular lumen during use. In some embodiments, the drive screw can be a right hand screw when the cutter is rotated in the right-hand direction; and, in some embodiments, the drive screw can be a left hand screw when the cutter is rotated in the left-hand direction.

We found that the ratios of (i) dimensions and (ii) stiffness of an atherectomy device taught herein each contribute to the performance and behavior of the device, the ease of advancement of the cutter, the ability to rotate the atherectomy device, the ability to steer the device, the relative amount of plaque removed, and the like. Table 2 provides example dimensions of the components of the atherectomy device, and Table 3 provides example ratios of the dimensions of the components of the atherectomy device.

TABLE 2

Examples of component dimension in mm.

| Cutter OD (mm) | Screw Pump OD (mm) | Drive Shaft OD (mm) | Sheath OD (mm) | Sheath ID (mm) | Minimum Front Cutting Diameter (mm) | Guidewire Lumen ID (mm) | Lateral Pushing Member OD (mm) |
|---|---|---|---|---|---|---|---|
| DESIGNED FOR LARGER ARTERIAL DIAMETERS | | | | | | | |
| 1.09-3.28 | 0.64-1.91 | 0.43-1.30 | 0.84-2.51 | 0.82-2.45 | 0.32-0.95 | 0.20-0.61 | 0.89-2.67 |
| or | or | or | or | or | or | or | or |
| 1.64-2.73 | 0.95-1.59 | 0.65-1.08 | 1.26-2.10 | 1.22-2.04 | 0.48-0.79 | 0.30-0.51 | 1.34-2.23 |

TABLE 2-continued

Examples of component dimension in mm.

| Cutter OD (mm) | Screw Pump OD (mm) | Drive Shaft OD (mm) | Sheath OD (mm) | Sheath ID (mm) | Minimum Front Cutting Diameter (mm) | Guidewire Lumen ID (mm) | Lateral Pushing Member OD (mm) |
|---|---|---|---|---|---|---|---|
| DESIGNED FOR SMALLER ARTERIAL DIAMETERS | | | | | | | |
| 0.70-2.10 or 1.05-1.75 | 0.51-1.52 or 0.76-1.27 | 0.43-1.30 or 0.65-1.08 | 0.69-2.06 or 1.03-1.71 | 0.65-1.95 or 0.98-1.63 | 0.32-0.95 or 0.48-0.79 | 0.20-0.61 or 0.30-0.51 | N/A |

TABLE 3

Examples of ratios of component dimensions

| Cutter OD:Screw Pump OD | Cutter OD:Sheath OD | Minimum Front Cutting Diameter:Cutter OD | Minimum Front Cutting OD:Guidewire Lumen ID | Screw Pump OD:Sheath ID | Screw OD:Drive Shaft OD | Cutter OD:Lateral Pushing Member OD |
|---|---|---|---|---|---|---|
| DESIGNED FOR LARGER ARTERIAL DIAMETERS | | | | | | |
| 1.26-3.79 or 1.90-3.163 | 1.00-1.95 or 0.98-1.63 | 0.15-0.44 or 0.22-0.36 | 1.00-2.35 or 1.17-1.96 | 0.39-1.17 or 0.58-0.97 | 1.00-2.21 or 1.10-1.84 | 1.00-1.84 or 0.92-1.53 |
| DESIGNED FOR SMALLER ARTERIAL DIAMETERS | | | | | | |
| 1.00-2.07 or 1.03-1.72 | 1.00-1.53 or 1.00-1.28 | 0.23-0.68 or 0.34-0.57 | 1.00-2.35 or 1.17-1.96 | 0.39-1.17 or 0.59-0.98 | 1.00-1.76 or 1.00-1.47 | N/A |

The "Cutter OD" is the largest outer diameter of the cutter.
The "Screw Pump OD" is the outer diameter of the drive shaft plus the two diameters of the screw pump wires surrounding the drive shaft.
The "Drive Shaft OD" is the outer diameter of the drive shaft and does not include the two diameters of the screw pump wires.
The "Sheath ID or OD" is the inner diameter or outer diameter of the flexible tube, or "sheath".
The "minimum front cutting OD" is the outer diameter of the most distal end of the cutter having cutting edges.
The "guidewire lumen ID" is the inner diameter of the guidewire lumen.
The "lateral pushing member OD" is the outer diameter of the lateral pushing member and can be taken in the collapsed state or the expanded state.

It was found that the relative sizes of the device component had a significant impact on the movement of the device within a vessel lumen. In some embodiments, the cutter diameter should be at least 30% greater than the drive shaft diameter. The ratio of cutter diameter to drive shaft diameter can range from 1.3 to 2.0 in some embodiments, 1.3 to 1.8 in some embodiments, 1.3 to 1.7 in some embodiments, 1.3 to 1.6 in some embodiments, 1.3 to 1.5 in some embodiments, 1.3 to 1.4 in some embodiments, or any range therein. In some embodiments, the ratio of cutter diameter to drive shaft diameter can be 1.3, 1.4, 1.5, 1.6, 1.7, 1.8, 1.9, 2.0, 2.1, 2.2, 2.3, 2.4, or 2.5, or any ratio therein in increments of 0.05, in some embodiments. In some embodiments, however, the cutter diameter is 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any percent therein in increments of 0.5%, greater than the drive shaft diameter.

In some embodiments, the cutter diameter should be at least 20% greater than the sheath. The ratio of cutter diameter to sheath diameter can range from 1.2 to 2.0 in some embodiments, 1.2 to 1.8 in some embodiments, 1.2 to 1.7 in some embodiments, 1.2 to 1.6 in some embodiments, 1.2 to 1.5 in some embodiments, 1.2 to 1.4 in some embodiments, 1.2 to 2.0 in some embodiments, or any range therein. In some embodiments, the ratio of cutter diameter to drive shaft diameter can be 1.2, 1.3, 1.4, 1.5, 1.6, 1.7, 1.8, 1.9, 2.0, 2.1, 2.2, 2.3, 2.4, or 2.5, or any ratio therein in increments of 0.05, in some embodiments. In some embodiments, however, the cutter diameter is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any percent therein in increments of 0.5%, greater than the sheath diameter.

The skilled artisan will appreciate that, given the teachings herein, the drive shaft, sheath and, in some embodiments, the lateral pushing member can be designed to have mechanical and physical properties that are desirable for the atherectomy procedure. In some embodiments, the mechanical and physical properties of the device provide adequate strength to push the cutter forward during the procedure yet flexible enough to maneuver and align the cutter with the guidewire in tortuous vessels.

One of skill will appreciate that the technology provided herein can include flexural stiffness design selections for components to facilitate enhanced performance, maneuverability, and reliability of the atherectomy devices. Flexural stiffness is a measure of deformability expressed in units of N/mm. For example, flexural stiffness may be described as the ability of the component to bend in response to an applied bending force without breaking or deforming the component. For example, one of skill may choose a flexural stiffness of the drive shaft, sheath, or both, in some embodiments, for maneuverability of the atherectomy device to follow a guide wire around tortuous vessels.

One of skill will also appreciate that the technology provided herein can include torsional stiffness design selections for components to facilitate enhanced performance through torsional strength. Torsional stiffness is resistance to twist from torsional loading, allowing the component to transmit a rotational load (torque) without untwisting, overtwisting, and/or deforming, and is in units of N*mm/rad. For example, one of skill may choose a torsional stiffness of the drive shaft, lateral pushing member or both, in some embodiments, to help ensure that the cutter can cut against resistance from the plaque without failure of the drive shaft, and the lateral pushing member doesn't rotate, or at least rotates only a limited amount, to avoid failure of the lateral pushing member device during the atherectomy procedure.

One of skill will also appreciate that the technology provided herein can include axial tensile stiffness design selections for components to facilitate enhanced performance through better response of the atherectomy devices to push and pull. Axial tensile stiffness is the resistance to stretch or contraction of along the length of the component under axial loading and is in units of N/mm. Key components that should include an axial tensile stiffness design selection include the drive shaft, the sheath, and the lateral pushing member.

Tables 4 and 5 provide examples of flexural stiffness, torsional stiffness, and axial stiffness of components of the atherectomy devices taught herein, as well as ratios of the relative stiffnesses of the components.

0.33, 0.34, 0.35, 0.36, 0.37, 0.38, 0.39, 0.40 or any ratio or range therein in increments of 0.005, in some embodiments. In some embodiments, however, the flexural stiffness of the sheath is 3×, 4×, 5×, 6×, 7×, 8×, 9×, 10×, or any range therein, greater than the flexural stiffness of the drive shaft.

Figure 5A:
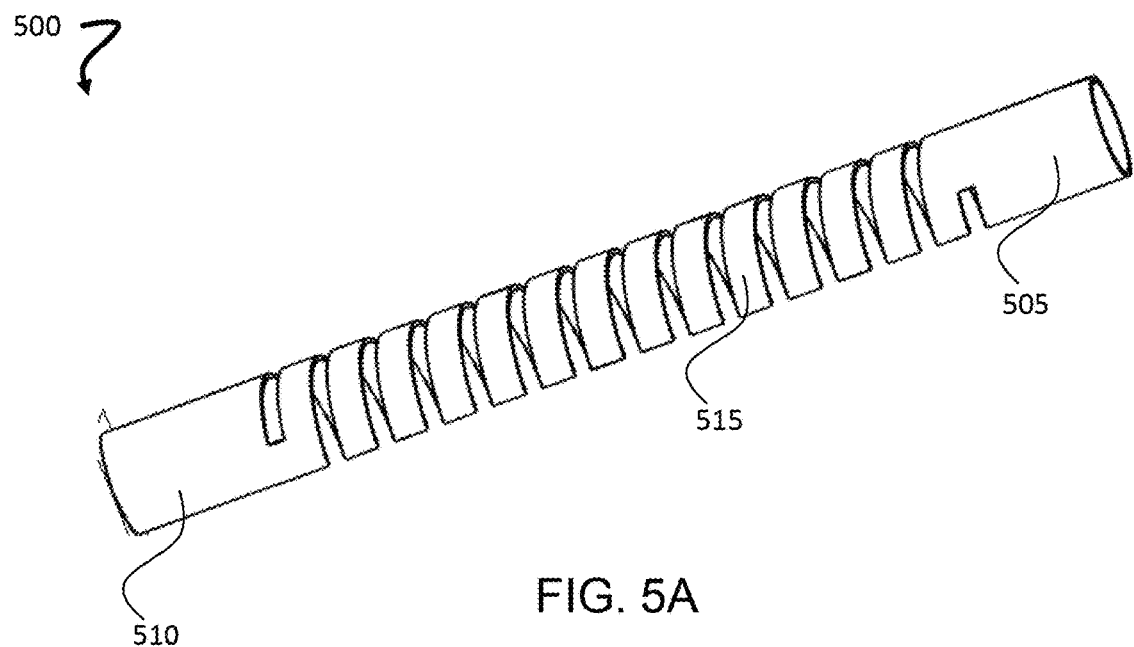
FIGS. 5A-5D illustrate a compressible sleeve that can be used to increase the torsional stiffness of the lateral pushing member, wherein the expansion of the lateral pushing member induces a curve, according to some embodiments.
Figure 5B:
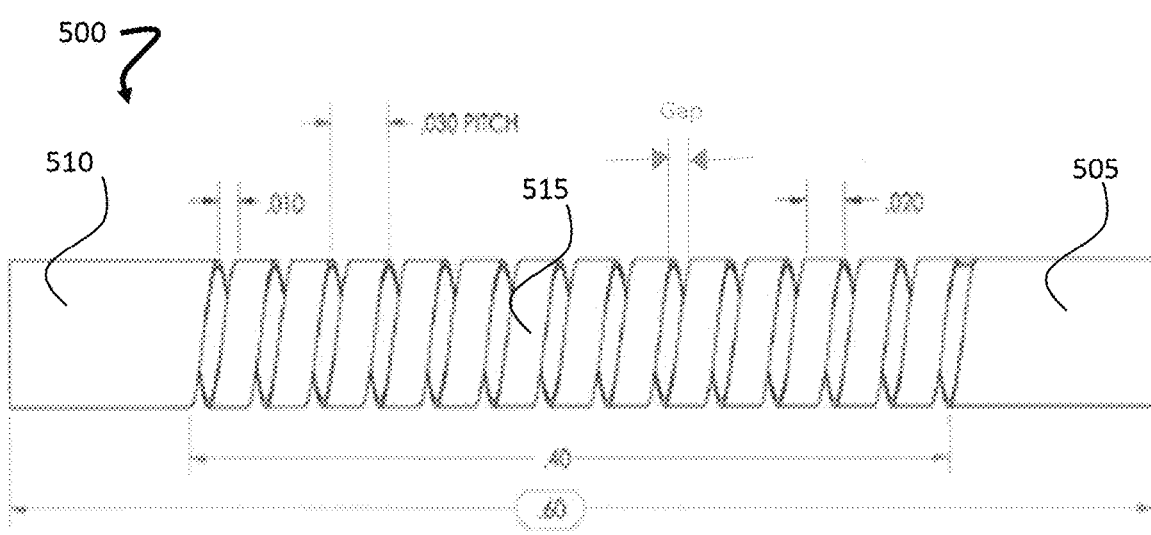
Figure 5C:
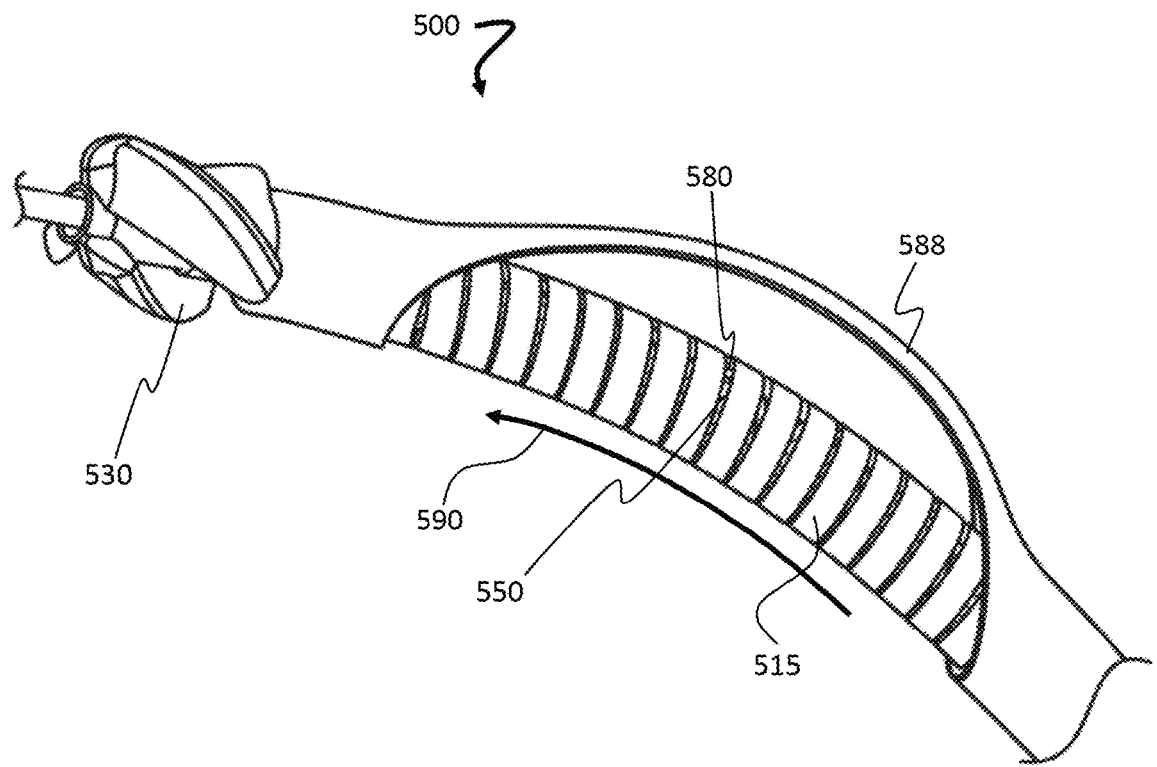

FIGS. 5A-5C illustrate a compressible sleeve that can be used to increase the torsional stiffness of the lateral pushing member, create a shield for the positive displacement pump, and increased the pumping efficiency to improve movement of cut particles out of the vessel, according to some embodiments. FIGS. 5A and 5B show that the compressible sleeve 500 has a proximal portion 505, a distal portion 510, and a compressible portion 515 having a spiral wound band that includes a gap between each of the spirals, a pitch between each of the spirals and a width and thickness of the spiral wound band. In some embodiments, the spiral wound band of the compressible portion 515 is integral with the proximal portion 505 and the distal portion 505.

FIG. 5C illustrates a deformation 590 of the distal portion of the atherectomy device. As discussed herein, the relative flexural stiffnesses of the distal portion of the drive shaft 550 and the trusses 588 in the lateral pushing member can induce the formation of the curve 590 as force is applied to induce lateral expansion of trusses 588, as described above, also changing the orientation of the cutter 630 in the vessel lumen (not shown). The compressible sleeve 500 compresses the spiral wound band of the compressible portion 515 during the lateral expansion of the trusses 588 and the creation of

TABLE 4

Example component stiffnesses for the atherectomy devices.

| Drive Shaft Flexural Stiffness (N/mm) | Drive Shaft Torsional Stiffness (N*mm/rad) | Drive Shaft Axial Stiffness (N/mm) | Sheath Flexural Stiffness (N/mm) | Lateral Pushing Member Torsional Stiffness (N*mm/rad) | Lateral Pushing Member Axial Stiffness (N/mm) | Lateral Pushing Member Flexural Stiffness (N/mm) |
|---|---|---|---|---|---|---|
| 0.09-0.26 or 0.13-0.22 | 12.73-38.20 or 19.10-31.83 | 2.59-7.76 or 3.88-6.46- | 0.72-2.15 or 1.07-1.79 | 0.75-2.24 or 1.12-1.86 | 0.82-2.45 or 1.23-2.04 | 0.40-1.20 or 0.60-1.00 |

TABLE 5

Examples of ratios of the relative component stiffnesses for the atherectomy devices.

| Drive Shaft Flexural Stiffness:Sheath Flexural Stiffness | Drive Shaft Flexural Stiffness:Drive Shaft Torsional Stiffness | Drive Shaft Flexural Stiffness:Drive Shaft Axial Stiffness | Drive Shaft Torsional Stiffness:Drive Shaft Axial Stiffness | Lateral Pushing Member Torsional Stiffness:Lateral Pushing Member Axial Stiffness | Drive Shaft Axial Stiffness:Lateral Pushing Member Axial Stiffness | Drive Shaft Flexural Stiffness:Lateral Pushing Member Flexural Stiffness | Sheath Flexural Stiffness:Lateral Pushing Member Flexural Stiffness |
|---|---|---|---|---|---|---|---|
| 0.06-0.18 or 0.09-0.15 | 0.003-0.010 or 0.005-0.009 | 0.02-0.05 or 0.03-0.04 | 2.46-7.39 or 3.69-6.16 | 0.46-1.37 or 0.68-1.14 | 1.58-4.74 or 2.37-3.95 | 0.11-0.33 or 0.16-0.27 | 0.89-2.67 or 1.34-2.23 |

The flexural stiffness of the sheath should be at least 3× greater than the drive shaft, in some embodiments. The ratio of flexural stiffness of the drive shaft to the flexural stiffness of the sheath can range from 0.03 to 0.40 in some embodiments, 0.05 to 0.30 in some embodiments, 0.05 to 0.25 in some embodiments, 0.06 to 0.30 in some embodiments, or any range therein. In some embodiments, the ratio of flexural stiffness of the drive shaft to the flexural stiffness of the sheath can be 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, the deformation 590 of the drive shaft and compressible sleeve 500. As such, the expansion of the trusses 588 in the lateral pushing member can induce a curve 590 on the distal portion of the atherectomy device, according to some embodiments.

Figure 5D:
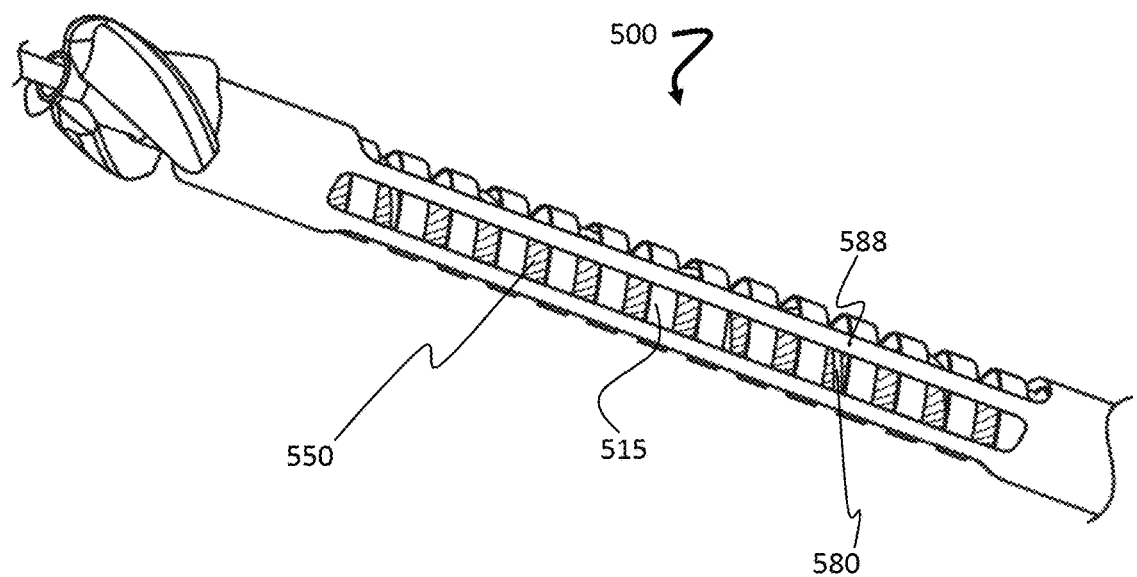

FIG. 5D illustrates a release of the deformation 590 of the distal portion of the atherectomy device to straighten the distal portion of the atherectomy device. The drive shaft 550 is telescoped out of the sheath (not shown) to relax the forces between the drive shaft 550 and trusses 588 and straighten the drive shaft 550 and trusses 588. This re-aligns the cutter 530 in the vessel lumen (not shown), from a position where the distal portion of the cutter 530 is oriented to cut, to a position where the side of the cutter 530 is oriented to cut. The compressible sleeve 500 relaxes and returns the spiral wound band of the compressible portion 515 from the deformation 590 caused by the lateral expansion of the trusses 588 to the original straight position as shown in FIG. 5D. As such, the expansion of the trusses 588 in the lateral pushing member can release deformation 590 on the distal portion of the atherectomy device and return to a straight position, according to some embodiments.

The compressible sleeve 500 can be placed outside of the flexible drive shaft and in-between the proximal and distal ends of the lateral pushing member, such that the flexible drive shaft 550 spins inside of the compressible sleeve. As shown herein, there can be a collar at each end of the laterally pushing member, a proximal collar and a distal collar, and the proximal portion 505 of the compressible sleeve 500 is operably attached to the proximal collar of the lateral pushing member, and the distal portion 510 of the compressible sleeve 500 is operably attached to the distal collar of the lateral pushing member. Due to the design of the compressible portion 515, the compressible sleeve 500 may be bent and compressed when the ribbons of the lateral pushing member protrude outwardly from a flat state while providing an added torsional stiffness between the proximal collar and the distal collar of the lateral pushing member to address torsion stresses on the lateral pushing member. In some embodiments, the distal and proximal collars of the lateral pushing member do not twist relative to each other, or any torsional movement is at least reduced. The compressible sleeve 500 also serves to cover the positive displacement pump, referred to as an Archimedes screw in some embodiments. As such, the compressible sleeve 500 can act as a safety shield during aspiration of the cut plaque particles with the Archimedes screw. And, it should be appreciated that having the cover over the positive displacement pump mechanism can assist the pump in the removal of particles by helping to retain the particles in a fixed space. For example, in the case of the screw pump, the compressible sleeve is in close proximity to the screw mechanism to retain plaque particles in the lumen of the compressible sleeve 500, helping the screw mechanism 580 move the particles out of the treated blood vessel with more efficiency. Moreover, the expanded trusses 588 of the lateral pushing member require the proximal and distal collars of the lateral pushing member to move closer together when compressing the compressible sleeve 500, the compressing occurring in the gaps between the spirals of the compressible sleeve 500 to allow the shortening to occur.

The compressible sleeve 500 can be made of any suitable material known to one of skill, the choice of material dictating the required band width and thickness, for example. In some embodiments, the compressible sleeve may be made of stainless steel, Nitinol, other metal alloys, or polymers, PEEK, polycarbonate, nylon, or polyimide.

Example dimensions for the compressible sleeve 500 are listed in Table 6, at least for lower extremity vasculature,

TABLE 6

Dimensions of the compressible sleeve designed for use in vasculature"

| Outer Diameter OD (mm) | Inner Diameter ID (mm) | Pitch (mm) | Gap (mm) |
| --- | --- | --- | --- |
| 0.76-2.29 | 0.70-2.10 | 0.38-1.14 | 0.13-0.38 |
| or | or | or | or |
| 1.14-1.91 | 1.05-1.7.5 | 0.57-0.95 | 0.19-0.32 |

TABLE 7

Flexural and torsional stiffness of the drive shaft and compressible sleeve.

| Drive Shaft | | | Compressible Sleeve | | |
| --- | --- | --- | --- | --- | --- |
| Flexural Stiffness (N/mm) | Torsional Stiffness (N-mm/rad) | Axial Stiffness (N/mm) | Flexural Stiffness (N/mm) | Torsional Stiffness (N-mm/rad) | Axial Stiffness (N/mm) |
| 0.09-0.26 | 12.73-38.20 | 2.59-7.76 | 0.03-0.08 | 0.02-0.05 | 0.04-0.12 |
| or | or | or | or | or | or |
| 0.13-0.22 | 19.10-31.83 | 3.88-6.46 | 0.04-0.06 | 0.03-0.04 | 0.06-0.10 |

The stiffness and ratio of the drive shaft and the compressible sleeve are listed below in Tables 8 and 9:

TABLE 9

Ratio of the stiffness of the drive shaft and the compressible sleeve for vasculature

| Drive Shaft Axial Stiffness:Compressible Sleeve Axial Stiffness | Drive Shaft Flexural Stiffness:Compressible Sleeve Flexural Stiffness |
| --- | --- |
| >32.97 | 1.71-5.13 |
| or | or |
| >49.46 | 2.56-4.27 |

The flexural stiffness of the drive shaft should be at least 50% greater than the drive compressible sleeve, in some embodiments. The ratio of flexural stiffness of the drive shaft to the flexural stiffness of the compressible sleeve can range from 1.5 to 6.0 in some embodiments, 1.5 to 5.0 in some embodiments, 1.6 to 5.0 in some embodiments, 1.7 to 5.0 in some embodiments, or any range therein. In some embodiments, the ratio of flexural stiffness of the drive shaft to the flexural stiffness of the compressible sleeve can be 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, or any ratio or range therein in increments of 0.1, in some embodiments. In some embodiments, however, the flexural stiffness of the drive shaft is 2×, 3×, 4×, 5×, 6×, or any amount in increments of 0.1×, or any range therein, greater than the flexural stiffness of the compressible sleeve.

Figure 6A:
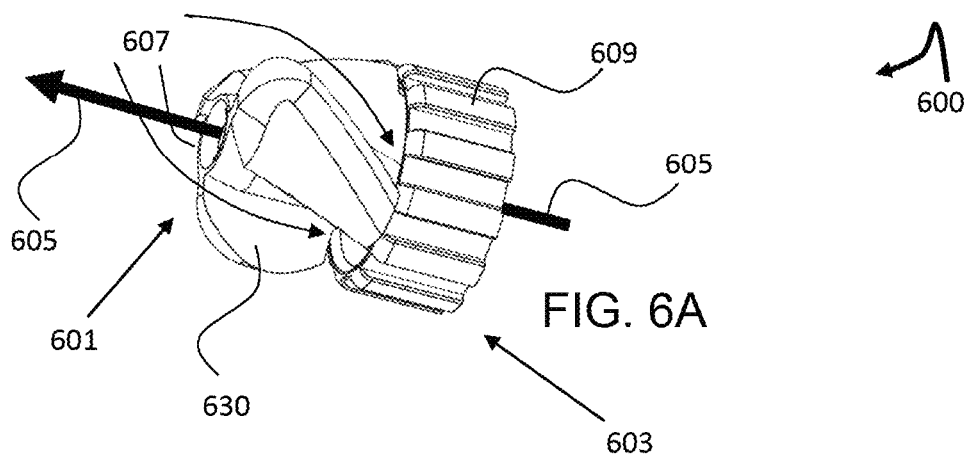
FIGS. 6A and 6B illustrate other cutters that may be used, according to some embodiments.
Figure 6B:
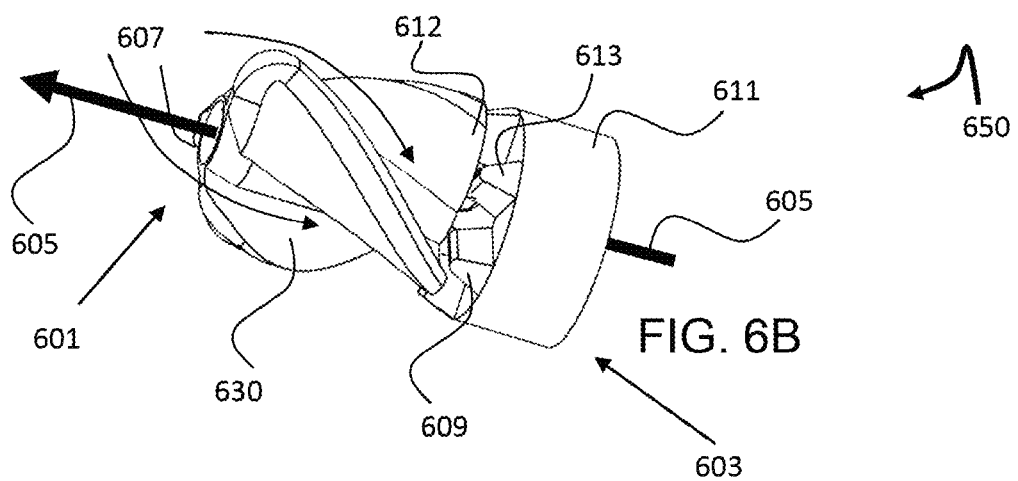

Although the performance of cutters can vary, depending on factors that include tissue type, for example, any cutter known to one of skill may be used with the atherectomy devices taught herein. FIGS. 6A and 6B illustrate other cutters that may be used, according to some embodiments. FIGS. 6A and 6B both show a cutter 600 having a distal end 601, proximal end 603, lumen 605, and flutes 607. The cutter 600 of FIG. 6A also has a burr portion 609, and the cutter 600 of FIG. 6B has a hammer portion 611.

The cutter in FIG. 6A has a burr portion 609 which can be fixed on the cutter, in some embodiments. In some embodiments, the burr portion 609 can be formed monolithically integral to the cutter. In some embodiments, however, the burr portion 609 can be operably attached to the cutter using a friction fitting, so that the burr is allowed slip on the base of the cutter when engaged with plaque and meeting a maximum torque limit.

The cutter in FIG. 6B has hammer portion 611 which can be fixed on the drive shaft, in some embodiments. In some embodiments, the hammer portion 611 can be operably attached to the cutter using a friction fitting, so that the hammer portion is allowed slip on the drive shaft when engaged with plaque and meeting a maximum torque limit. The hammer portion 611 has oscillating teeth 613 that contact the blade portion 612 to create an oscillating hammer effect on the plaque for cutting.

Atherectomy systems can also be assembled to include the atherectomy devices taught herein. In some embodiments, any of the atherectomy devices taught herein can be a system comprising the atherectomy device and a guidewire.

The atherectomy devices also lend to several methods of performing an atherectomy in a subject. In some embodiments, the methods can include creating a point of entry in a vascular lumen of the subject; inserting the atherectomy device into the vascular lumen; telescoping the flexible drive shaft; cutting a plaque from the vascular lumen with the cutter of the atherectomy device; discharging the cut plaque from the vascular lumen with the positive displacement pump; and, removing the atherectomy device from the vascular lumen of the subject.

In some embodiments, the methods can include creating a point of entry in a vascular lumen of the subject; inserting the atherectomy device into the vascular lumen; driving the atherectomy device through the vascular lumen with the exposed drive screw; cutting a plaque from the vascular lumen with the cutter of the atherectomy device; discharging the cut plaque from the vascular lumen with the positive displacement pump; and, removing the atherectomy device from the vascular lumen of the subject.

Likewise, in some embodiments, the methods can include creating a point of entry in a vascular lumen of the subject; inserting the atherectomy device into the vascular lumen; pushing the distal portion of the atherectomy device laterally in the vascular lumen, the pushing including expanding the lateral pushing member; cutting a plaque from the vascular lumen with the cutter of the atherectomy device; discharging the cut plaque from the vascular lumen with the positive displacement pump; and, removing the atherectomy device from the vascular lumen of the subject.

Likewise, in some embodiments, the methods can include grinding the plaque with a burr like, for example, the burr portion 609 of FIG. 6A. The burr can having ridges, like the burr portion 609, or it can be a grinding surface having a desired "grit".

Likewise, in some embodiments, the methods can include hammering the plaque with a hammering cutting blade configuration like, for example, the cutting portion 612 of the cutter of FIG. 6B.

One of skill will appreciate that the steps set-forth above represent only example of a series of steps that may be used in an atherectomy. In a simple embodiment, for example, the method includes inserting an atherectomy device taught herein into a vascular lumen of a subject, the atherectomy device having a distal end, a proximal end, a long axis, and a guidewire lumen passing through the device in the direction of the long axis;

a flexible sheath having an outer diameter and a sheath lumen; a cutter having a proximal end, a distal end, and a body with a plurality of helical flutes, a point at the distal end having a plurality of cutting lips, a cutter lumen, and a cleared diameter; and, a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath; and, a positive displacement pump that begins pumping at the distal end of the drive shaft and adjacent to the helical flutes at the proximal end of the cutter;

advancing the cutter to a target area in the vascular lumen of the subject, the advancing including telescoping the distal end of the flexible drive shaft away from the distal end of the flexible sheath to increase the flexibility of the atherectomy device in the vascular lumen;

self-driving the cutter into the target region, the self-driving including turning a screw at the distal end of the flexible drive shaft;

laterally pushing the distal end of the flexible sheath, distal end of the flexible drive shaft, and the cutter against the wall of the vascular lumen; or, a combination thereof;

cutting plaque away from the wall of the vascular lumen, the cutting including rotating the cutter; and, removing the plaque from the vascular lumen using the positive displacement pump; and, removing the atherectomy device from the subject.

It should be appreciated that the devices, systems and methods provided herein allow for enhanced functionality during an atherectomy procedure. In some embodiments, a method of steering a cutting head are provided, and these methods can include redirecting the distal end of the flexible atherectomy device. In some embodiments, the redirecting can include (i) expanding the pushing member, the expanding including pulling a centralized "member"

(ii) wherein the expanding expands the lateral pushing member to push and bend/curve the distal end of the flexible atherectomy device.

The centralized "member" can be, for example, either the flexible drive shaft, or perhaps a centralized tendon that is also freely translatable in the axial direction, meaning translatable in the longitudinal axis direction, and perhaps even forming the guidewire lumen in some embodiments. A truly surprising and unexpected benefit was provided by the centralized pull on or near the central axis of the atherectomy device, central axis of the sheath, and or central axis of the drive shaft. To reiterate this surprising result, prior art Telescoping, self-driving, and laterally-pushing atherectomy devices are provided, each having a flexible sheath, a cutter with helical flutes, and a drive assembly. The drive assembly can have a flexible driveshaft that is rotatably translational with the lumen of the flexible sheath, a positive displacement pump that begins pumping at the distal end of the drive shaft adjacent to the helical flutes at the proximal end of the cutter, and the flexible drive shaft can be longer than the flexible sheath to enable a reversible telescoping of the drive assembly from the lumen of the flexible sheath. The positive displacement pump can be a screw pump having a drive screw portion extending beyond the flexible sheath, exposed for contact with a vascular lumen for the self-driving. And, the devices can have a reversibly-expandable, lateral pushing member at the distal end of the flexible sheath for the lateral pushing.

Hybrid Cutters for Removing Hard Tissue, Soft Tissue, and a Combination of Hard and Soft Tissue.

The cutting efficiency of each of the atherectomy devices taught herein can be improved through the design of the cutter. It should be appreciated that the cutter can also be referred to as a "cutting head", a "bit", a "mill", or an "end mill", in some embodiments. As such, a hybrid atherectomy cutter for cutting a combination of soft and hard plaque is provided.

Figure 7A:
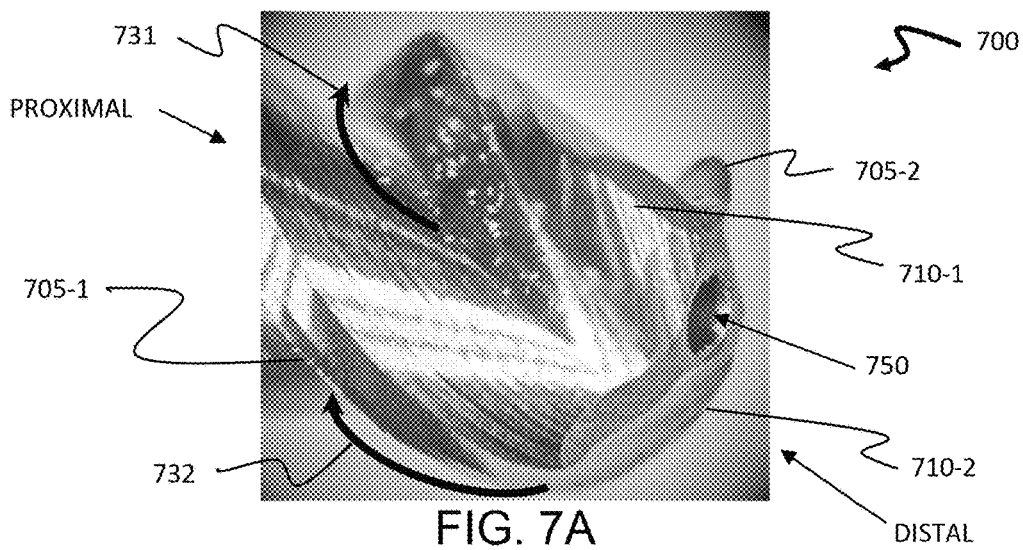
FIGS. 7A-7C illustrate features of the cutters, including the primary and secondary cutting edges, flutes, helix angle, and guidewire lumen, according to some embodiments.
Figure 7B:
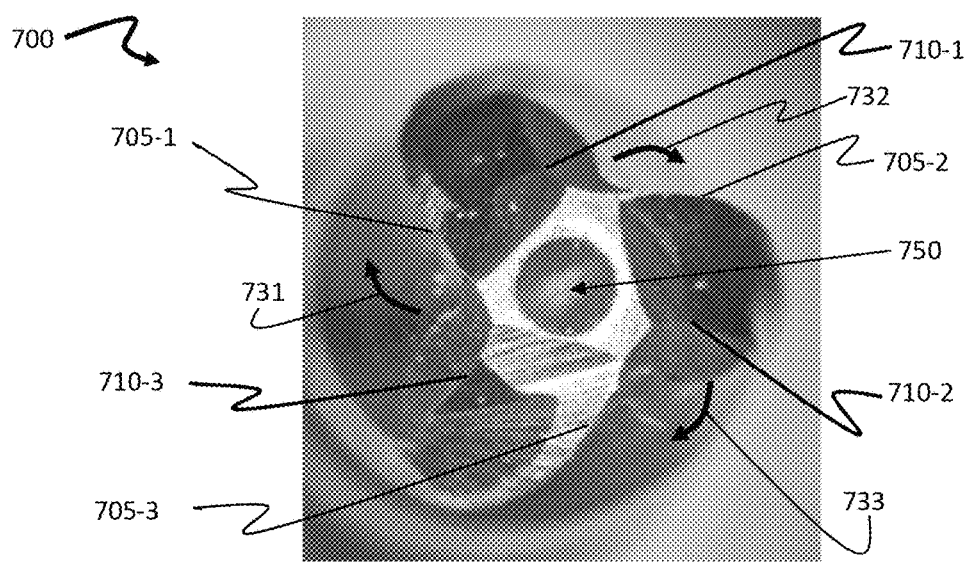
Figure 7C:
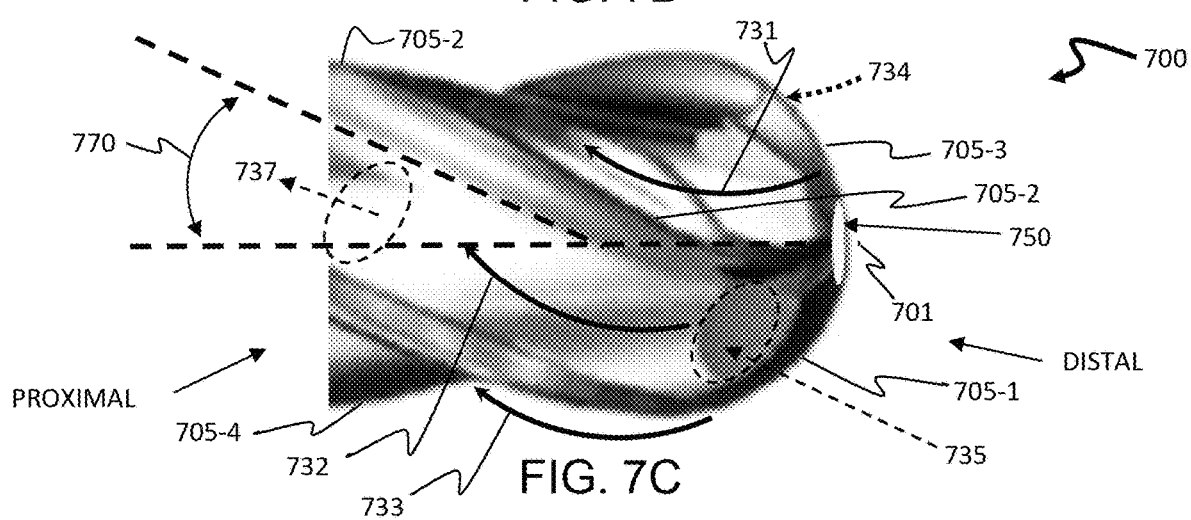

FIGS. 7A-7C illustrate features of the cutters, including the primary and secondary cutting edges, flutes, helix angle, and guidewire lumen, according to some embodiments. As shown in FIG. 7C, the cutter can include a proximal end, a distal end, and a longitudinal axis. FIG. 7A is a perspective view of both the proximal and distal ends of a cutter, FIG. 7B is a view of the distal end of a three-flute cutter, and FIG. 7C is a side view of a four-flute cutter. As shown in 7A, the cutter 700 can have a first primary cutting edge 705-1 and a second primary cutting edge 705-2, the first primary cutting edge 705-1 and the second primary cutting edge 705-2 extending helically from the distal end to the proximal end and along the radius. Likewise, there is a first secondary cutting edge 710-1 and a second secondary cutting edge 710-2. The cutter 700 can have a first helical flute 730 and a second helical flute 731, each of the first helical flute 731 and the second helical flute 732 having a helix angle 770 relative to the longitudinal axis 701 and forming a helical channel with a distal entry 735 and a proximal exit 737, such that the helical channel is open at the distal end and the proximal end to allow cut tissue to enter and exit from the helical channel, which is a function of all cutters taught herein. And, the cutter 700 can have a lumen 750 configured for passage of a guidewire (not shown). As shown in FIG. 7B, In some embodiments, the cutter 700 can have a third primary cutting edge 705-3 and a third secondary cutting edge 710-3, as well as a third helical flute 733. As shown in FIG. 7C, In some embodiments, the cutter 700 can have a fourth primary cutting edge 705-4 and a fourth secondary cutting edge 710-4 (not shown), as well as a fourth helical flute 734 (labeled but not visible in FIG. 7C).

The primary cutting edges can extend along the entire cutter, and may be divided into three different portions, in some embodiments: a proximal portion, a middle portion, and a distal portion. The proximal portion of each of the primary cutting edges can have a helical shape and, for example, may follow a path along a constant diameter in some embodiments. The middle portion of each of the primary cutting edges can have a spiral shape, and may also follow a constant diameter. The distal portion of each of the primary cutting edges can then taper down towards the distal end of the cutter in some embodiments.

The secondary cutting edges can be shorter than the primary cutting edges, in some embodiments. In some embodiments, the secondary cutting edges can be the same length as the primary cutting edges. In some embodiments, the secondary cutting edges are less than ½ the length of the primary cutting edges. In some embodiments, the secondary cutting edges are less than ¼ the length of the primary cutting edges. In some embodiments, the secondary cutting edges range from about 5% of the length of the primary cutting edges to about 45% of the length of the cutting edges. In some embodiments, the secondary cutting edges can be formed through the addition of facets, which may be in the form of two adjacent planes, plane 1 and plane 2 towards the distal end of the cutter.

In some embodiments, a secondary cutting edges can be located between each two primary cutting edges, one facet being a first plane having a first side coincident with the primary cutting edge, and a second facet being a second plane having a second side coincident with the first plane.

In some embodiments, the secondary cutting edges, like the distal portion of the primary cutting edges, can also taper down towards the distal end of the cutter. In some embodiments, the secondary cutting edges and the primary cutting edges can both decrease towards the distal end of the cutter.

In some embodiments, the distal-most portions of the secondary cutting edges and the distal-most portions of the primary cutting edges can function in front-cutting, creating a pathway for the atherectomy in a narrowed or fully blocked lesion. Moreover, the front-cutting that is achieved through the combination of the primary cutting edges and the secondary cutting edges can cut the plaque into smaller particles than can be achieved with a conventional, state-of-the-art atherectomy device. In some embodiments, the helical, spiral-shaped profile of the primary cutting edges provides a continuous removal of debulked material by continuously transferring tissue proximally during operation of the cutter.

Figure 8A:
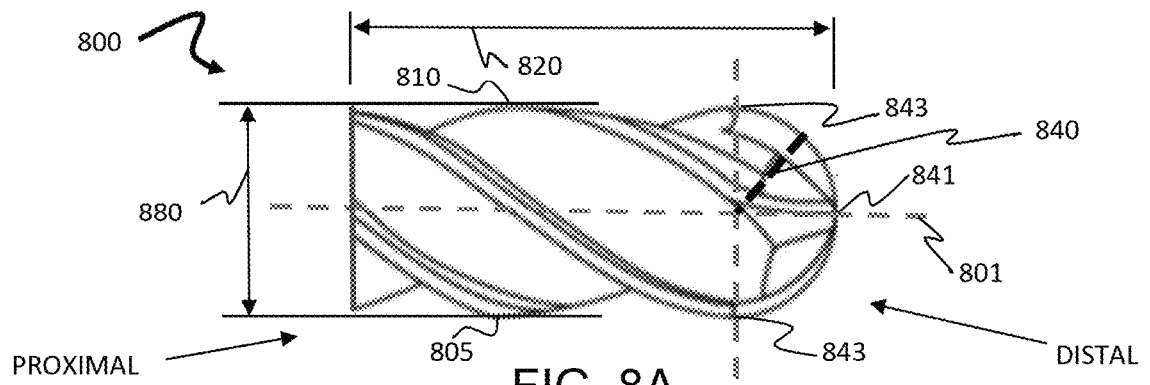
FIGS. 8A-8D illustrate features of cutters, including cutting length, radius, and cutting diameter, according to some embodiments.
Figure 8B:
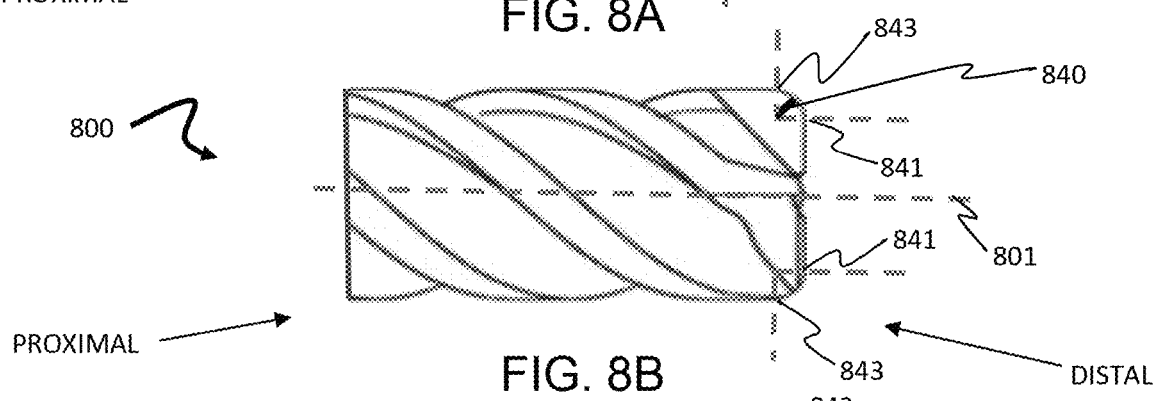
Figure 8C:
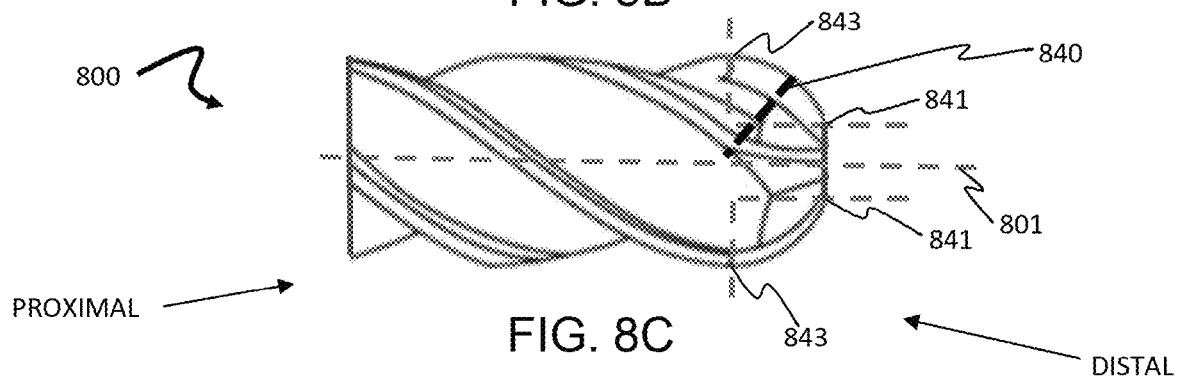
Figure 8D:
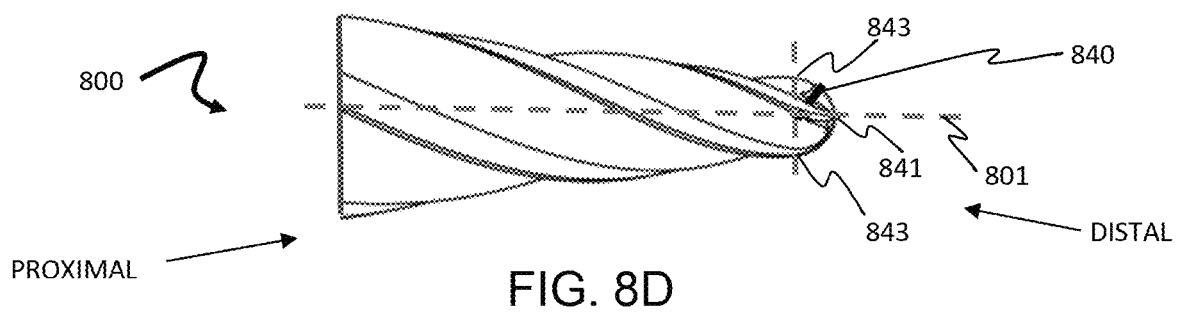

FIGS. 8A-8D illustrate features of the cutters taught herein, including cutting length, radius, and cutting diameter, according to some embodiments. As shown in FIG. 8A-8D, the cutting length 820 of the cutter 800 is defined by the distance from the proximal end to the distal end along the longitudinal axis 801. The configuration of a cutter 800 can have a radius 840 at the distal end, the radius 840 having an inner inflection point 841 and an outer inflection point 843. The cutter can also have a cutting diameter 880, the cutting diameter being the maximum distance between the first primary cutting edge 805 and the second primary cutting edge 810 measured normal to the longitudinal axis 801. FIG. 8A illustrates the radius 840 being a ball nose radius at the distal end of the cutter 800, where the radius can be half the cutting diameter in some embodiments. FIG. 8B illustrates a cutter 800 having a radius 840 that is a corner radius at the distal end of the cutter, where the distal end of the cutter is generally flat. FIG. 8C illustrates a cutter 800 having a radius that is generally a ball nose radius but the distal-most portion of the cutter 800 is flat, the radius being a mix of a ball nose radius and a corner radius. FIG. 8D illustrates a cutter 800 in which the cutting diameter 880 gradually reduces, tapers, from the proximal end to the distal end, in which the distal end can have a radius 840 that is a ball nose radius, as illustrated, a corner nose radius (reference FIG. 8B), or a combination of a ball nose radius and a corner nose radius (reference FIG. 8C). The distal end of such a tapered cutter can have a diameter measured at the outer inflection points 843 that is 10%, 20%, 30%, 40%, 50%, 60%, 70%, 80%, 90%, or any percentage therein in increments of 1%, of the cutting diameter 880 measured at the proximal end of the cutter.

One of skill will appreciate that, in many embodiments, the radius at the distal end of the cutter can have any desired shape. In some embodiments, the radius is a ball nose radius. In some embodiments, the radius is a corner radius. In some embodiments, the radius is a combination of a ball nose radius and a corner radius. And, in some embodiments, the radius equals half the diameter of the cutter.

Figure 9A:
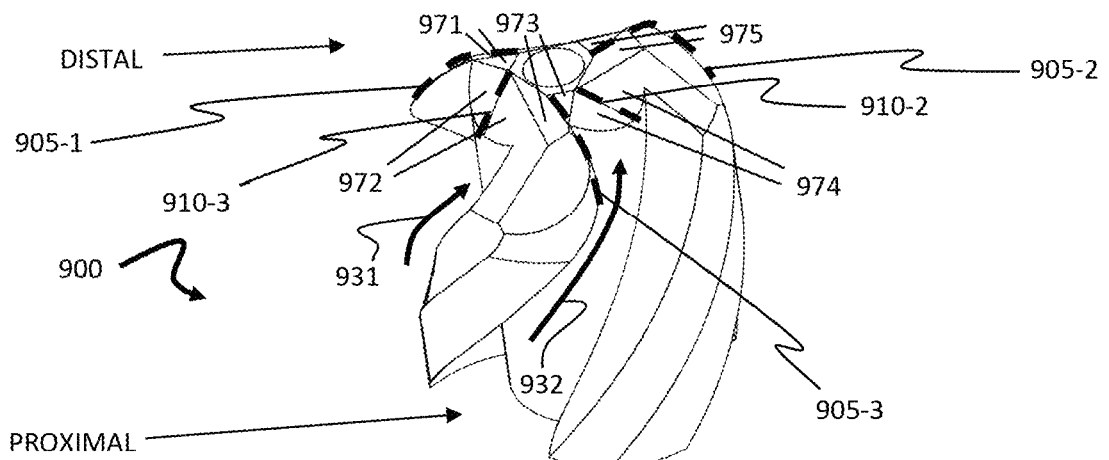
FIGS. 9A-9C illustrate perspective, proximal end, and distal end views of the primary and secondary cutting edges, as well as the primary facets and secondary facets that improve the cutting of tissue by the cutter, according to some embodiments.
Figure 9B:
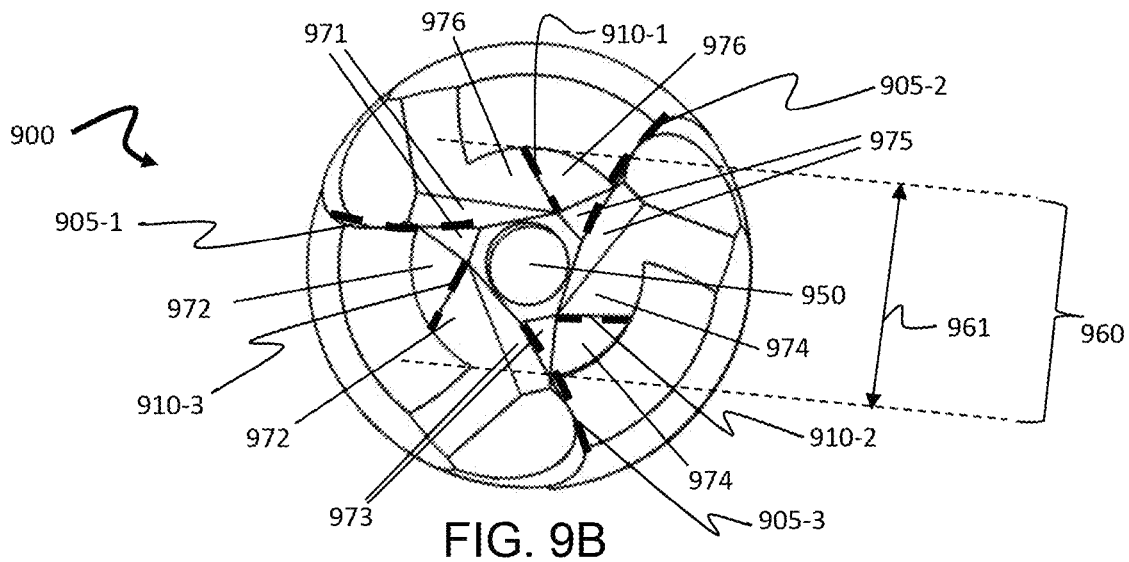
Figure 9C:
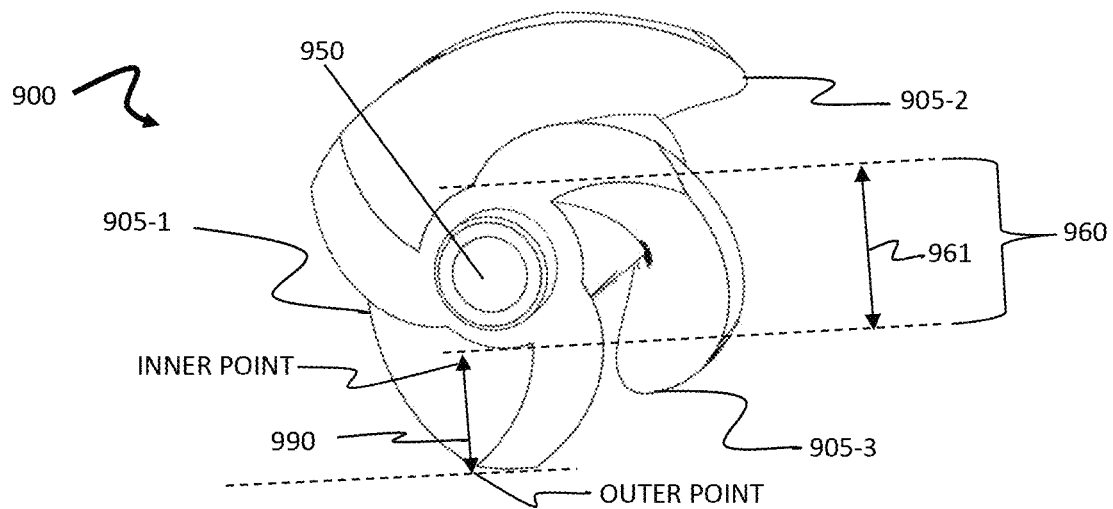

FIGS. 9A-9C illustrate perspective, proximal end, and distal end views of the primary and secondary cutting edges, as well as primary facets and secondary facets that shape the primary and secondary cutting edges and improve the cutting of tissue by the cutter, according to some embodiments. The dashed-lines highlight at least the distal-most portions of the primary cutting edges and secondary cutting edges. In FIGS. 9A and 9B, the cutter 900 illustrates the feature of a core 960 forming a central portion of the cutter 900 and containing the cutter lumen 950. FIGS. 9A and 9B illustrate features that can be a part of any cutter configuration including at least the core 960 with a core diameter 961, a distal end, and a proximal end; wherein, the distal end of the core 960 is configured with a first plurality of secondary facets 972 that form a first secondary cutting edge 910-1 at the distal end of the first helical flute 931 and following the first primary cutting edge 905-1; and, a second plurality of secondary facets 974 that form a second secondary cutting edge 910-2 at the distal end of the second helical flute 932 and following the secondary primary cutting edge 905-2. Moreover, the cutters can have a third plurality of secondary facets 976 at the distal end of a third helical flute (not shown) that form a third secondary cutting edge 910-3 and following the third primary cutting edge 905-3. One of skill should appreciate that the creation of the secondary cutting edges 910-1,910-2,910-3 with the introduction of the secondary facets 972,974,976 contribute to the cutters having the desired, "hybrid" function of effectively cutting both soft and hard tissue, namely plaque, in blood vessels.

One of skill should appreciate from the teachings provided herein that a "facet" is made at the "distal end portion" of the core of the cutter, as "core" is defined herein, and the distal end portion is less than the distal % of the length of the cutter. In some embodiments, the distal end portion is the distal 49% of the length of the cutter. In some embodiments, the distal end portion is the distal 40% of the length of the cutter. In some embodiments, the distal end portion is the distal 30% of the length of the cutter. In some embodiments, the distal end portion is the distal 20% of the length of the cutter. In some embodiments, the distal end portion is the distal 15% of the length of the cutter. In some embodiments, the distal end portion is the distal 10% of the length of the cutter. In some embodiments, the distal end portion is the distal 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, of the length of the cutter, or any % therein in amounts of 0.1%. In some embodiments, the distal end portion is greater than % the length of the cutter. In some embodiments, the distal end portion is the distal 95%, 90%, 85%, 80%, 75%, 70%, 65%, 60%, 55%, 50% of the length of the cutter, or any % therein in amounts of 0.1%.

The embodiments also include cutters having primary facets to improve cutting of tissue with the primary cutting edges. As shown in FIG. 9A, in some embodiments, the distal end of the core further comprises a plurality of first primary facets 971 at the distal end of the first primary cutting edge 905-1. FIG. 9A also illustrates that, in some embodiments, the distal end of the core further comprises a plurality of second primary facets 973 at the distal end of the second primary cutting edge 905-2. Moreover, as shown in FIG. 9A, the cutters can have a third plurality of primary facets 975 at the distal end of a third helical flute (not shown) that form a third primary cutting edge 905-3. In some embodiments, the plurality of the first primary facets 971 can be configured to extend the reach of the first primary cutting edge 905-1; the plurality of the second primary facets 973 can be configured to extend the distal reach of the second primary cutting edge 905-2; and, likewise, the plurality of the third primary facets 975 can be configured to extend the distal reach of the third primary cutting edge 905-3.

One of skill will appreciate that each of the cutters taught herein is designed to include flutes. In some embodiments, the cutter can have 2 flutes. In some embodiments, the cutter can have 3 flutes. In some embodiments, the cutter can have 4 flutes. In some embodiments, the cutter can have 5 flutes. In some embodiments, the cutter can have 6 flutes. Each of the flutes is helical in shape and can have a helix of any desired angle, such that a combination of flutes can have the same helix angle or have combination of helix angles on any single cutter.

As shown in FIG. 9C, the flutes can have a flute depth 990 that can be defined by the distance between the surface of the core 960 at an inner point of the flute depth 990 and the surface of the primary cutting edge 905-1 at an outer point of the flute depth 990. In some embodiments, the helix angle and/or flute depth can vary from the proximal end to the distal end of the flute. In some embodiments, the flute depth can range from 0.05 mm to 2.0 mm, from 0.1 mm to 1.5 mm, from 0.2 mm to 1.1 mm, from 0.4 mm to 1.1 mm, from 0.2 to 0.5 mm, from 0.3 mm to 0.4 mm, from 0.6 mm to 0.9 mm, or any range or amount therein in increments of 0.1 mm. In some embodiments, the flute depth can be 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, or any amount or range therein in increments of 0.05 mm.

It should be appreciated that, in some embodiments, a cutter will have 2 flutes, 3 flutes, or 4 flutes. One of skill will appreciate that the cutters can have any number of flutes desired, at least 2 flutes and up to a reasonable number of flutes, of course, and retain the ability to retain the configuration of primary cutting edges and secondary cutting edges. In some embodiments, the number of flutes matches the number of primary cutting edges, and the number of flutes can range from 2-8. In some embodiments, the number of flutes matches the number of primary cutting edges, and the number of flutes can be 2-4, 2-5, 2-6, 2-7, or 2-8 flutes. In some embodiments, cutters can have 3 or 4 flutes. In some embodiments, the cutters have 3 flutes, 3 primary cutting edges, and 3 secondary cutting edges.

In some embodiments, each of the flutes of a cutter can have the same angle or a different angle when compared to the other flute or flutes of the cutter where, for example, one of skill may choose a cutter with such a variable flute configuration for a smoother cut. As such, in some embodiments, the flute angle can be constant or variable where, for example, one of skill may choose the "variable helix", or variable flute angle between flutes, for materials that may be more resistant to cutting, and perhaps increase the efficiency of the cutting. A helix angle of greater than 45° is considered to be a "high angle" and will be more efficient at removing material from the cutting site and leave a smoother cut surface while reducing tissue packing and re-cutting of tissue; whereas, a helix angle of less than 40° is considered to be a "low angle" and may remove larger pieces of material for a given cutting time and leave a rougher cut surface while, perhaps, creating packing and recutting of tissue in some applications. In some embodiments, a flute can have a high helix angle; and, in some embodiments, a flute can have a low helix angle. In some embodiments, a flute can have a helix angle ranging from 5° to 70°, or any angle therein. In some embodiments, a flute can have a helix angle ranging from 10° to 65°, or any angle therein. In some embodiments, a flute can have a helix angle ranging from 15° to 60°, or any angle therein. In some embodiments, a flute can have a helix angle ranging from 20° to 60°, or any angle therein. In some embodiments, a flute can have a helix angle ranging from 25° to 60°, or any angle therein. And, in some embodiments, a flute can have a helix angle ranging from 30° to 60°, or any angle therein. In some embodiments, a flute can have a helix angle ranging from 35° to 40°, or any angle therein. In some embodiments, a flute can have a helix angle ranging from 37° to 45°, or any angle therein. In some embodiments, a flute can have a helix angle ranging from 30° to 45°, or any angle therein. And, in some embodiments, a flute can have a helix angle ranging from 45° to 60°, or any angle therein. As such, it should be appreciated that a flute can have a helix angle that is about 3°, 4°, 5°, 6°, 7°, 8°, 9°, 10°, 15°, 20°, 25°, 30°, 35°, 40°, 45°, 50°, 55°, 60°, 65°, 70°, 75°, or any angle therein in increments of 0.1°. One of skill will further appreciate that a cutter can have a combination of flutes having any combination of helix angles.

Figure 10A:
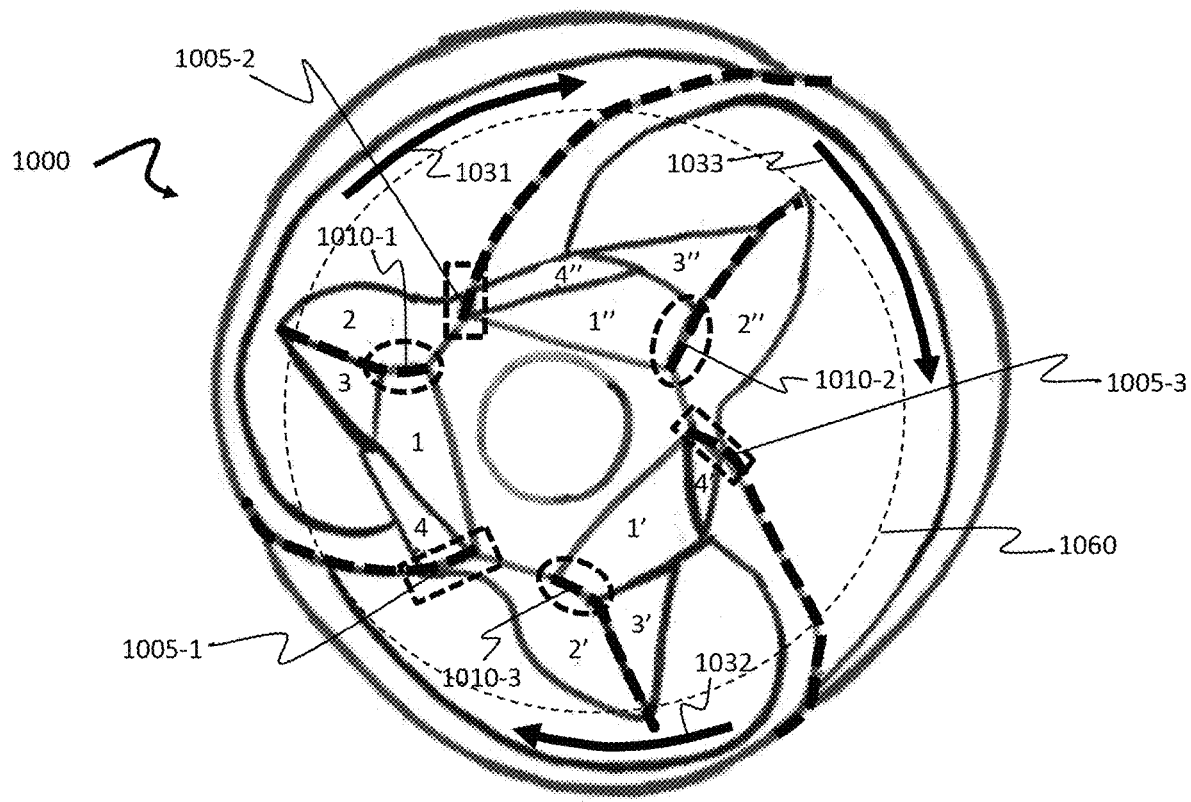
FIGS. 10A and 10B illustrate a mapping of primary and secondary facets and their relation to the primary cutting edges and secondary cutting edges, according to some embodiments.
Figure 10B:
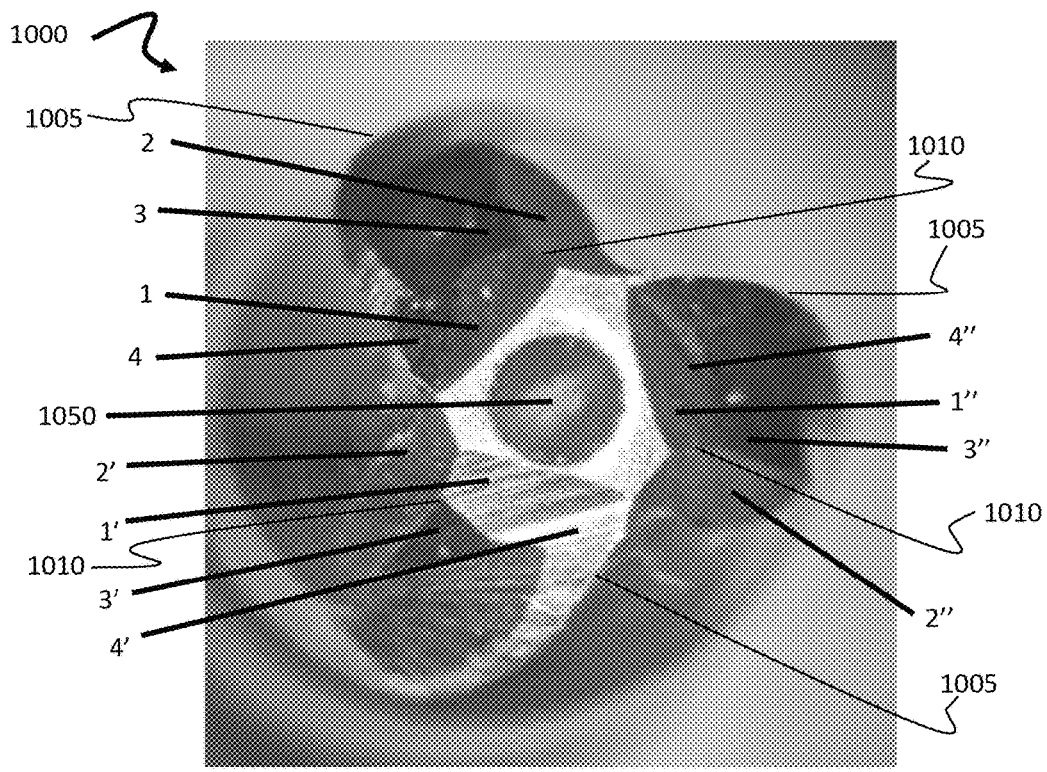

FIGS. 10A and 10B illustrate a mapping of primary and secondary facets and their relation to the primary cutting edges and secondary cutting edges, according to some embodiments. One of skill will recognize from the illustrations and teachings that the creation of the primary and the secondary facets at the distal end of the core contributes to the desired cutting efficiency of both hard and soft plaque. One of skill will also appreciate that any number of facets can be introduced, and a facet is a feature at the distal end or distal portion of the cutter that can be a plane, a concave surface, or a convex surface, in some embodiments. As shown in FIG. 10A, the cutters 1000 include secondary facets 1,2,3 that are introduced into the distal end or distal portion of the core to produce secondary cutting edges 1010-1, 1010-2, 1010-3. In some embodiments, the distal end of the core can be configured with a first plurality of secondary facets 1,2,3 that form a first secondary cutting edge 1010-1 at the distal end of the first helical flute 1031; in some embodiments, the distal end of the core can be configured with a second plurality of secondary facets 1',2',3' that form a second secondary cutting edge 1010-2 at the distal end of the second helical flute 1032; and, in some embodiments, the distal end of the core can be configured with a third plurality of secondary facets 1",2",3" that form a third secondary cutting edge 1010-3 at the distal end of the third helical flute 1033.

As further shown in FIG. 10A, the plurality of the first secondary facets 1,2 can be configured to extend the distal reach of the first secondary cutting edge 1010-1; in some embodiments, the plurality of the second secondary facets 1',2', can be configured to extend the distal reach of the second secondary cutting edge 1010-2; and, likewise, in some embodiments, the plurality of the third primary facets 1",2" can be configured to extend the distal reach of the third secondary cutting edge 1010-3. The extended distal reach is shown by the elliptical dashed outline around the distal secondary cutting edges 1010-1, 1010-2, 1010-3.

The embodiments also include cutters having primary facets to improve cutting of tissue with the primary cutting edges. As shown in FIG. 10A, the distal end of the core 1060 further comprises a plurality of first primary facets 2',4 at the distal end of the first primary cutting edge 1005-1; in some embodiments, the distal end of the core 1060 further comprises a plurality of second primary facets 2",4' at the distal end of the second primary cutting edge 1005-2. in some embodiments, the distal end of the core 1060 further comprises a plurality of third primary facets 2,4" at the distal end of the third primary cutting edge 1005-3.

As further shown in FIG. 10A, the plurality of the first primary facets 2',4 can be configured to extend the distal reach of the first primary cutting edge 1005-1; in some embodiments, the plurality of the second primary facets 2",4' can be configured to extend the distal reach of the second primary cutting edge 1005-2; and, likewise, in some embodiments, the plurality of the third primary facets 2,4" can be configured to extend the distal reach of the third primary cutting edge 1005-3. The extended distal reach is shown by the rectangular dashed outline around the distal secondary cutting edges 1010-1,1010-2,1010-3. FIG. 10B illustrates the distal end of an actual cutter showing these primary and secondary facets on a prototype cutter that produced the desired results of cutting both soft and hard tissue.

In some embodiments, a facet can be both a primary facet that serves to shape a primary cutting edge, and a secondary facet that serves to shape a secondary cutting edge 1010-1, 1010-2,1010-3. In FIGS. 10A and 10B, for example, facets 2, 2', and 2" serve as both primary and secondary facets. In fact, it can be seen also that facets 1, 1', and 1" serve mainly as secondary facets for the secondary cutting edges, but they also serve to shape a small portion of the primary cutting edges 1005-1,1005-2,1005-3, making them also primary facets. Facets 3, 3', and 3" serve as secondary facets only, and facets 4, 4', and 4" serve as primary facets only, at least in the illustrated embodiments.

Figure 11A:
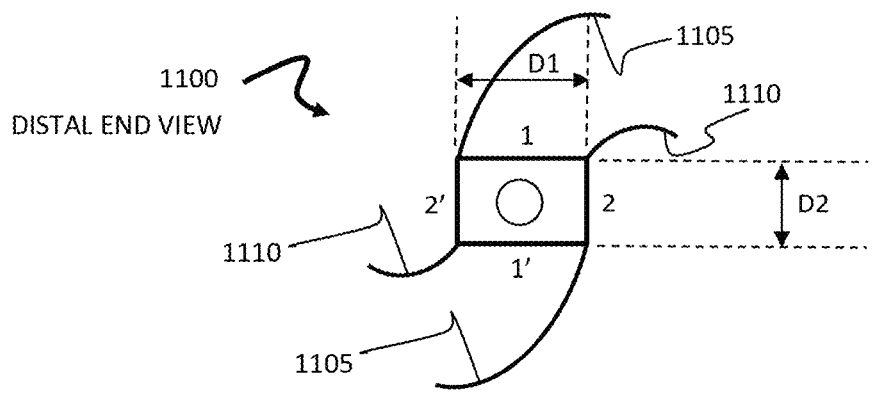
FIGS. 11A-11C illustrate simplified distal-to-proximal views of the distal end of 2-flute, 3-flute, and 4-flute cutters, according to some embodiments.
Figure 11B:
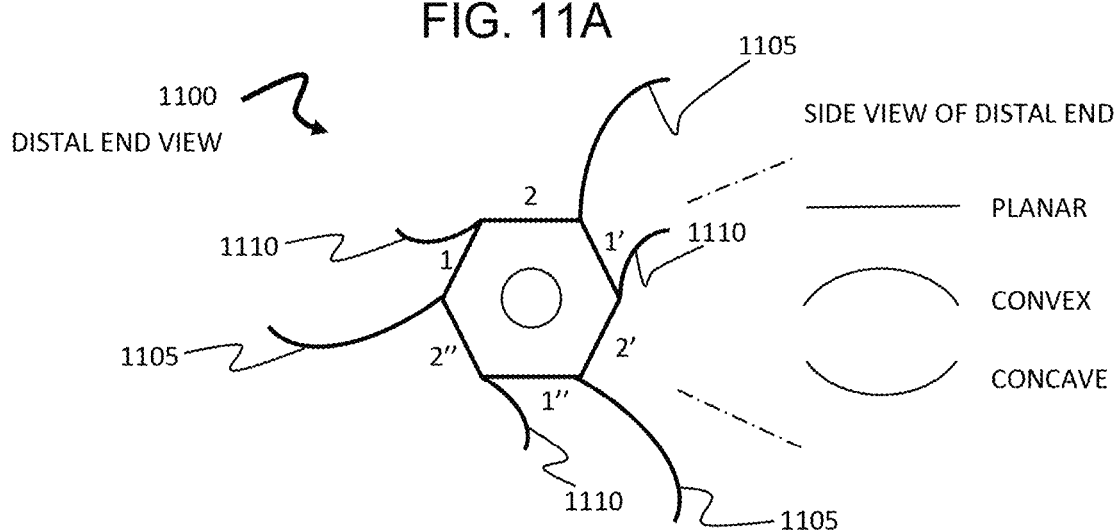
Figure 11C:
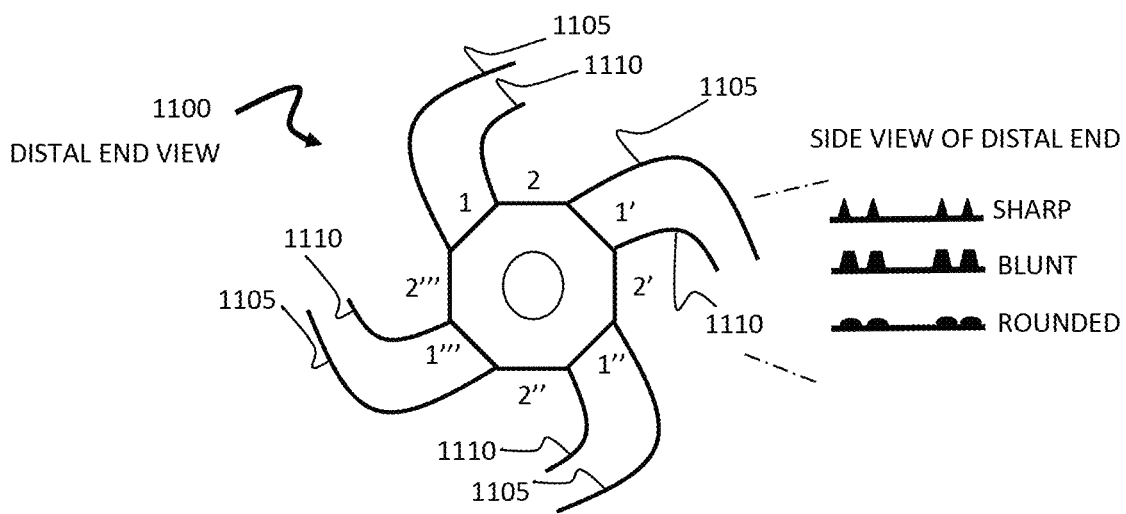

FIGS. 11A-11C illustrate simplified distal-to-proximal views of the distal end of 2-flute, 3-flute, and 4-flute cutters, according to some embodiments. In particular the drawings show the distal edges of the facets used to shape at least the distal ends of the secondary cutting edges. FIG. 11A shows the distal end of a 2-flute cutter having 2 primary cutting edges 1105 and 2 secondary cutting edges 1110. In this embodiment, the distal end of the cutter is a 4-sided polygon which can be square or rectangular and can have any cross-sectional area desired with a minimum cross-sectional area being greater than the cross sectional area of the cutter lumen and less than the cross sectional area defined by the cutter diameter. The sides of the 4-sided polygon are the distal edges of the facets that shape the secondary cutting edges. In FIG. 11A, facets 1, 2, 1', and 2' define at least the distal portions of the secondary cutting edges 1110. FIG. 11B shows the distal end of a 3-flute cutter having 3 primary cutting edges 1105 and 3 secondary cutting edges 1110. In this embodiment, the distal end of the cutter is a 6-sided polygon which can be hexagonal, or more triangular in shape as shown in FIG. 10B, and can have any cross-sectional area desired with a minimum cross-sectional area being greater than the cross sectional area of the cutter lumen and less than the cross sectional area defined by the cutter diameter. The sides of the 6-sided polygon are the distal edges of the facets that shape the secondary cutting edges. In FIG. 11B, facets 1, 2, 1',2',1", and 2" define at least the distal portions of the secondary cutting edges 1110. FIG. 11B also illustrates a side view of the distal end of the cutter, showing 3 optional shapes for the distal end: planar, convex, and concave. One of skill will appreciate that these are exemplary shapes and that any desired shape may be used to help facilitate the cutting and removal of tissue by the primary cutting edges, secondary cutting edges, and flutes. FIG. 11C shows the distal end of a 4-flute cutter having 4 primary cutting edges 1105 and 4 secondary cutting edges 1110. In this embodiment, the distal end of the cutter is an 8-sided polygon which can be octagonal, or perhaps more rectangular in shape, and can have any cross-sectional area desired with a minimum cross-sectional area being greater than the cross sectional area of the cutter lumen and less than the cross sectional area defined by the cutter diameter. The sides of the 8-sided polygon are the distal edges of the facets that shape the secondary cutting edges. In FIG. 11C, facets 1, 2, 1',2',1",2",1''' and 2''' define at least the distal portions of the secondary cutting edges 1110. FIG. 11C also illustrates a side view of the distal end of the cutter, showing 3 options for configuring the distal end with tissue-disrupting projections: sharp, blunt, and concave. One of skill will appreciate that these are exemplary projections and that any desired projections may be used to have the function of disrupting the tissue for to help facilitate the cutting and removal of the tissue by the primary cutting edges, secondary cutting edges, and flutes.

It should be appreciated that any of the features shown in FIGS. 11A-11C can be used in any cutter produced using the teachings provided herein, regardless of the combination of, and number of, primary cutting edges, secondary cutting edges, flutes, shape and cross-sectional area of the distal of the cutter, and the like. This teaching is not, however, suggesting that the exemplary facets shown will always be enough to obtain the shapes desired in a cutter. It should also be appreciated that the facets shown for shaping at least the distal end of the secondary cutting edges may help to shape at least the distal end of the primary cutting edges, but that additional facets may be needed, and often will be needed, to shape at least distal end of the primary cutting edges as desired.

One of skill will appreciate that the cutters can be configured with any number of primary and secondary cutting edges, and the number of the primary and secondary cutting edges can be the same or different. In some embodiments, a cutter can have 2 primary cutting edges and 0 secondary cutting edges. In some embodiments, a cutter can have 2 primary cutting edges and 1 secondary cutting edges. In some embodiments, a cutter can have 2 primary cutting edges and 2 secondary cutting edges. In some embodiments, a cutter can have 2 primary cutting edges and 3 secondary cutting edges. In some embodiments, a cutter can have 3 primary cutting edges and 0 secondary cutting edges. In some embodiments, a cutter can have 3 primary cutting edges and 1 secondary cutting edges. In some embodiments, a cutter can have 3 primary cutting edges and 2 secondary cutting edges. In some embodiments, a cutter can have 3 primary cutting edges and 3 secondary cutting edges. In some embodiments, a cutter can have 3 primary cutting edges and 4 secondary cutting edges. In some embodiments, a cutter can have 4 primary cutting edges and 0 secondary cutting edges. In some embodiments, a cutter can have 4 primary cutting edges and 1 secondary cutting edges. In some embodiments, a cutter can have 4 primary cutting edges and 2 secondary cutting edges. In some embodiments, a cutter can have 4 primary cutting edges and 3 secondary cutting edges. In some embodiments, a cutter can have 4 primary cutting edges and 4 secondary cutting edges. In some embodiments, a cutter can have 4 primary cutting edges and 5 secondary cutting edges.

In some embodiments, the cutters can have a third primary cutting edge extending helically from the distal end to the proximal end and along the radius at the distal end of the cutter; and, a third helical flute having a helix angle and forming a helical channel that is open at the distal end and the proximal end. In some embodiments, the core can be further configured with a third plurality of secondary facets that form a third secondary cutting edge at the distal end of the third helical flute. Likewise, the core can be further configured with a third plurality of primary facets at the distal end of the third primary cutting edge, the third plurality of primary facets configured to extend the distal reach of the third primary cutting edge.

In some embodiments, the cutters can have a third primary cutting edge extending helically from the distal end to the proximal end and along the radius at the distal end of the cutter; a fourth primary cutting edge extending helically from the distal end to the proximal end and along the radius; a third helical flute having a helix angle and forming a helical channel that is open at the distal end and the proximal end; and, a fourth helical flute having a helix angle and forming a helical channel that is open at the distal end and the proximal end. In some embodiments, the core can be further configured with a third plurality of secondary facets that form a third secondary cutting edge at the distal end of the third helical flute; and, a fourth plurality of secondary facets that form a fourth secondary cutting edge at the distal end of the third helical flute. Likewise, the core can be further configured with a third plurality of primary facets at the distal end of the third primary cutting edge, the third plurality of primary facets configured to extend the distal reach of the third primary cutting edge; and, a fourth plurality of primary facets at the distal end of the fourth primary cutting edge, the fourth plurality of primary facets configured to extend the distal reach of the fourth primary cutting edge.

One of skill will appreciate that the primary cutting edges and/or the secondary cutting edges may be fashioned to have a "relief angle" to reduce the drag of the cutting edge on the tissue and increase the cutting efficiency of the cutter. The relief angle, however, is not a "facet", as described in the technology provided herein. Although a facet may also provide a relief angle in some embodiments, the main objective of the facet is to remove core material to configure the presence of a secondary cutting edge at the distal portion of the cutter and, in some embodiments, to extend the distal reach of a primary cutting edge at the distal end of the cutter.

One of skill will appreciate that any of the atherectomy devices taught herein have several technical contributions of their own, outside of the cutter configurations, and that any of the atherectomy devices can include any of the cutters taught herein to further enhance performance of the atherectomy device. In some embodiments, the atherectomy devices includes a cutter taught herein, the cutter having a cleared diameter; a distal end, a proximal end, a long axis, and a guidewire lumen passing through the device in the direction of the long axis; a flexible sheath having an outer diameter and a sheath lumen; a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath, the drive assembly also having a positive displacement pump that begins pumping at the distal end of the drive shaft and adjacent to the helical flutes at the proximal end of the cutter. In these embodiments, the cleared diameter of the cutter can be greater than the outer diameter of the flexible sheath; the flexible drive shaft can be longer than the flexible sheath to enable a reversible telescoping of the drive assembly from the lumen of the flexible sheath at the distal end of the flexible sheath; and, the guidewire lumen can include the cutter lumen and the driveshaft lumen.

In some embodiments, the atherectomy devices includes a cutter taught herein, the cutter having a cleared diameter; a distal end, a proximal end, a long axis, and a guidewire lumen passing through the device in the direction of the long axis; a flexible sheath having an outer diameter and a sheath lumen; a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath, the drive assembly also having a screw pump attached to the outer surface of the drive shaft and adjacent to the helical flutes at the proximal end of the cutter, the screw pump including a drive screw portion; wherein, the drive screw portion extends beyond the flexible sheath and is exposed for contact with a vascular lumen during use of the atherectomy device within the vascular lumen; and, is either a right hand screw when the cutter is rotated in the right-hand direction; or, a left hand screw when the cutter is rotated in the left-hand direction. In these embodiments, the cleared diameter of the cutter can be greater than the outer diameter of the flexible drive shaft; and, the guidewire lumen can include the cutter lumen and the driveshaft lumen.

In some embodiments, the atherectomy devices includes a cutter taught herein, the cutter having a cleared diameter; a distal end, a proximal end, a long axis, and a guidewire lumen passing through the device in the direction of the long axis; a flexible sheath having an outer diameter and a sheath lumen; a drive assembly having a flexible driveshaft including an axis, a proximal end, a distal end, an outer surface, and a driveshaft lumen, the distal end of the flexible drive shaft having a fixed connection with the cutter, wherein the flexible drive shaft is rotatably translational with the lumen of the flexible sheath, the drive assembly also having a positive displacement pump that begins pumping at the distal end of the drive shaft and adjacent to the helical flutes at the proximal end of the cutter. And, the atherectomy device can also have a reversibly-expandable, lateral pushing member at the distal end of the flexible sheath, the lateral pushing member having a proximal end, a distal end, a collapsed state, and an expanded state, the proximal end having an operable connection with the flexible sheath, and the distal end having an operable connection with the cutter. In these embodiments, the cleared diameter of the cutter can be greater than the outer diameter of the flexible sheath; the guidewire lumen can include the cutter lumen and the driveshaft lumen. Moreover, the operable connection with the flexible sheath and the operable connection with the cutter can be each configured to receive an axial force (i) applied along the axis of the flexible drive shaft from the cutter to the flexible sheath and (ii) transferred through the lateral pushing member during the collapse and the expansion of the lateral pushing member with a reversible telescoping of the flexible drive shaft from the flexible sheath; and, the operable connection with the cutter can be configured as a rotatably translatable connection to facilitate a rotation of the cutter and the flexible drive shaft without rotating the lateral pushing member during operation of the atherectomy device.

Figure 12:
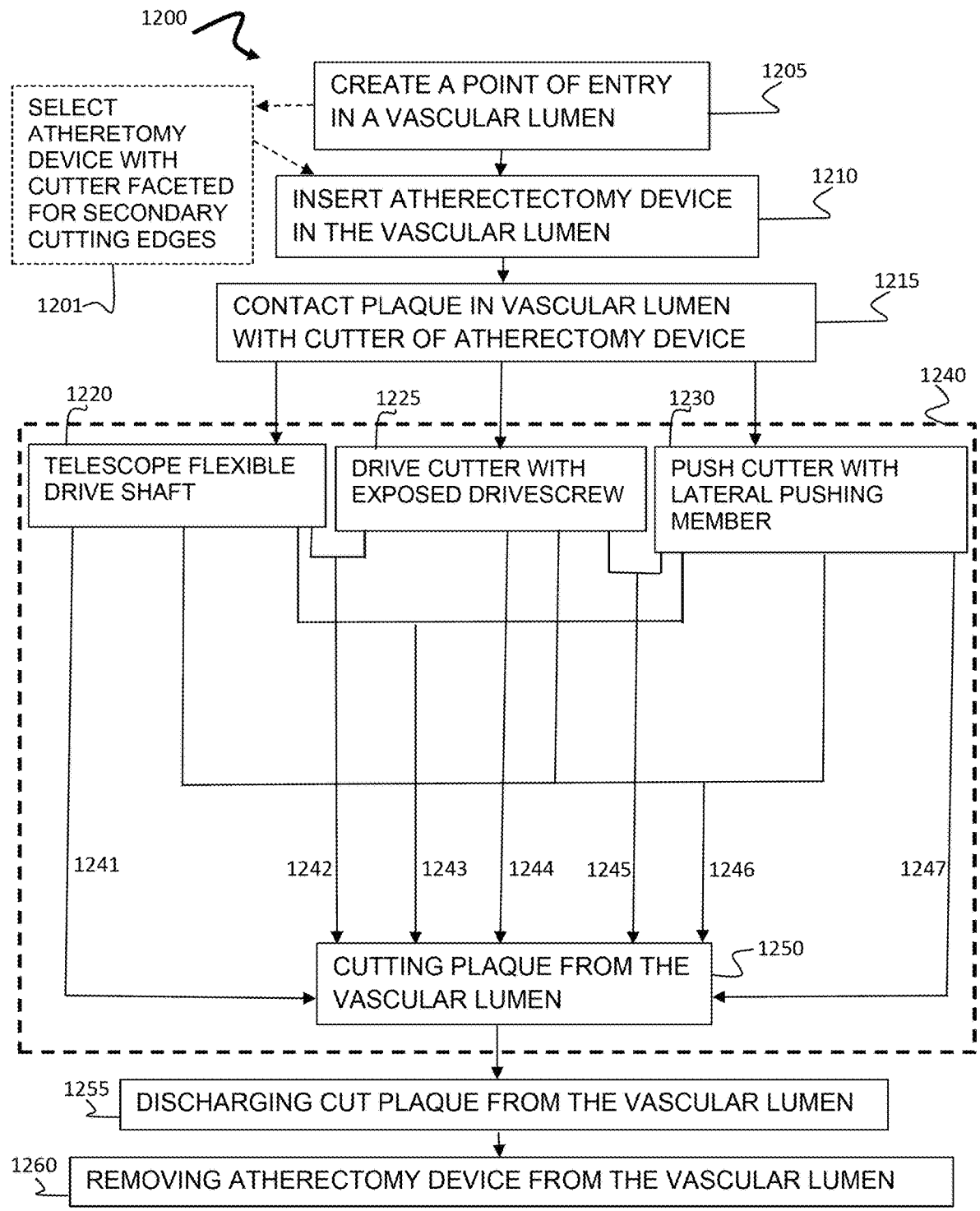
FIG. 12 charts methods of performing an atherectomy, according to some embodiments.

FIG. 12 charts methods of performing an atherectomy, according to some embodiments. One of skill will also appreciate that any of the methods of performing an atherectomy can include using any of the atherectomy devices taught herein with any of the cutters taught herein. Regardless of the atherectomy device used, the methods 1200 can include creating 1205 a point of entry in a vascular lumen of the subject; inserting 1210 the atherectomy device into the vascular lumen; cutting 1215 a plaque from the vascular lumen with the cutter of the atherectomy device; discharging 1255 the cut plaque from the vascular lumen with the positive displacement pump; and, removing 1260 the atherectomy device from the vascular lumen of the subject. The methods can also include advancing 1240 the cutter head to contact tissue for removal using the improved cutter control functionalities of the atherectomies devices provided herein, including telescoping 1220 a flexible drive shaft for contacting 1241 the target tissue for removal, driving 1225 the cutter with an exposed drive screw for contacting 1244 the target tissue for removal, pushing 1230 the cutter with a lateral pushing member for contacting 1247 the target tissue for removal, or any combination thereof. Such combinations can include, for example, telescoping/driving 1242, driving/pushing laterally 1245, telescoping/pushing laterally 1243, and telescoping/driving/pushing laterally 1246. As such, in addition to the optional step of selecting 1201 an atherectomy device having a cutter faceted for secondary cutting edges, which may also be faceted for extending the primary cutting edges further distally, the selecting limited to the variety of cutters taught herein, FIG. 12 illustrates at least 7 different methods of performing an atherectomy with the atherectomy devices taught herein.

We claim:

1. An atherectomy device, comprising:
   a cutter having a cleared diameter, the cutter including
      a proximal end, a distal end, and a longitudinal axis;
      a cutting length defined by the distance from the proximal end to the distal end along the longitudinal axis;
      a radius at the distal end, the radius having an inner inflection point and an outer inflection point;
      a first primary cutting edge and a second primary cutting edge, the first primary cutting edge and the second primary cutting edge extending helically from the distal end to the proximal end and along the radius;
      a first helical flute and a second helical flute, each of the first helical flute and the second helical flute having a helix angle and forming a helical channel that is open at the distal end and the proximal end;
      a cutting diameter, the cutting diameter being the maximum distance between the first primary cutting edge and the second primary cutting edge measured normal to the longitudinal axis;
      a core having a core diameter, a distal end, and a proximal end;
   wherein the distal end of the core is configured with a first plurality of secondary facets that form a first secondary cutting edge at the distal end of the first helical flute; and,
   a second plurality of secondary facets that form a second secondary cutting edge at the distal end of the second helical flute;

wherein, the cutter
has a lumen configured for passage of a guidewire;
effectively cuts both soft and hard plaque in blood vessels; and
has a cleared diameter;
a distal end, a proximal end, a long axis, and a guidewire lumen passing through the device in the direction of the long axis;
a flexible sheath having an outer diameter and a sheath lumen; and,
a drive assembly having
a flexible driveshaft including an axis, a proximal end, a distal end, an outer surface, an outer diameter and a driveshaft lumen, the distal end of the flexible drive shaft having a fixed connection with the cutter, wherein the flexible drive shaft is rotatably translational with the lumen of the flexible sheath; and,
a positive displacement pump that begins pumping at the distal end of the flexible drive shaft and adjacent to the first helical flute and the second helical flute at the proximal end of the cutter;
wherein,
the cleared diameter of the cutter is greater than the outer diameter of the flexible drive shaft;
the flexible drive shaft is longer than the flexible sheath to enable a reversible telescoping of the drive assembly from the lumen of the flexible sheath at the distal end of the flexible sheath; and,
the guidewire lumen includes the cutter lumen and the driveshaft lumen.

2. The atherectomy device of claim 1, wherein,
the cutter further includes;
a third primary cutting edge extending helically from the distal end to the proximal end and along the radius; and,
a third helical flute having a helix angle and forming a helical channel that is open at the distal end and the proximal end;
wherein, the core is further configured with
a third plurality of secondary facets that form a third secondary cutting edge at the distal end of the third helical flute; and,
a third plurality of primary facets at the distal end of the third primary cutting edge, the third plurality of primary facets configured to extend the distal reach of the third primary cutting edge.

3. The atherectomy device of claim 2, wherein:
the positive displacement pump is a screw pump attached to the outer surface of the flexible drive shaft and adjacent to the first helical flute and the second helical flute at the proximal end of the cutter, the screw pump including a drive screw portion; wherein, the drive screw portion
extends beyond the flexible sheath and is exposed for contact with a vascular lumen during use of the atherectomy device within the vascular lumen;
and, is either a right hand screw when the cutter is rotated in the right-hand direction; or,
a left hand screw when the cutter is rotated in the left-hand direction.

4. The atherectomy device of claim 2, further comprising
a reversibly-expandable, lateral pushing member at the distal end of the flexible sheath; the lateral pushing member having a proximal end, a distal end, a collapsed state, and an expanded state, the proximal end having an operable connection with the flexible sheath, and the distal end having an operable connection with the cutter;
wherein,
the operable connection with the flexible sheath and the operable connection with the cutter are each configured to receive an axial force (i) applied along the axis of the flexible drive shaft from the cutter to the flexible sheath and (ii) transferred through the lateral pushing member during the collapse and the expansion of the lateral pushing member with a reversible telescoping of the flexible drive shaft from the flexible sheath; and,
the operable connection with the cutter is configured as a rotatably translatable connection to facilitate a rotation of the cutter and the flexible drive shaft without rotating the lateral pushing member during operation of the atherectomy device.

5. The atherectomy device of claim 1, further comprising:
a reversibly-expandable, lateral pushing member at the distal end of the flexible sheath; the lateral pushing member having a proximal end, a distal end, a collapsed state, and an expanded state, the proximal end having an operable connection with the flexible sheath, and the distal end having an operable connection with the cutter;
wherein,
the operable connection with the flexible sheath and the operable connection with the cutter are each configured to receive an axial force (i) applied along the axis of the flexible drive shaft from the cutter to the flexible sheath and (ii) transferred through the lateral pushing member during the collapse and the expansion of the lateral pushing member with a reversible telescoping of the flexible drive shaft from the flexible sheath; and,
the operable connection with the cutter is configured as a rotatably translatable connection to facilitate a rotation of the cutter and the flexible drive shaft without rotating the lateral pushing member during operation of the atherectomy device.

6. A method of performing an atherectomy in a subject using the atherectomy device of claim 5, the method comprising
creating a point of entry in a vascular lumen of the subject;
inserting the atherectomy device into the vascular lumen;
telescoping the flexible drive shaft;
cutting a plaque from the vascular lumen with the cutter of the atherectomy device;
discharging the cut plaque from the vascular lumen with the positive displacement pump; and,
removing the atherectomy device from the vascular lumen of the subject.

7. The atherectomy device of claim 1, wherein:
the positive displacement pump is a screw pump attached to the outer surface of the flexible drive shaft and adjacent to the first helical flute and the second helical flute at the proximal end of the cutter, the screw pump including a drive screw portion; wherein, the drive screw portion
extends beyond the flexible sheath and is exposed for contact with a vascular lumen during use of the atherectomy device within the vascular lumen;
and, is either a right hand screw when the cutter is rotated in the right-hand direction; or, a left hand screw when the cutter is rotated in the left-hand direction.

8. A method of performing an atherectomy in a subject using the atherectomy device of claim 7, the method comprising
creating a point of entry in the vascular lumen of the subject;
inserting the atherectomy device into the vascular lumen;
driving the atherectomy device through the vascular lumen with the exposed drive screw portion;
cutting a plaque from the vascular lumen with the cutter of the atherectomy device;
discharging the cut plaque from the vascular lumen with the screw pump; and,
removing the atherectomy device from the vascular lumen of the subject.

\* \* \* \* \*